(12) United States Patent
Takemoto et al.

(10) Patent No.: US 8,592,435 B2
(45) Date of Patent: Nov. 26, 2013

(54) NITROGEN-CONTAINING SIX-MEMBERED AROMATIC RING DERIVATIVES AND PHARMACEUTICAL PRODUCTS CONTAINING THE SAME

(75) Inventors: Naohiro Takemoto, Osaka (JP); Kenji Murata, Osaka (JP); Norihito Murayama, Tokyo (JP); Chikaomi Yamada, Osaka (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 212 days.

(21) Appl. No.: 12/596,054

(22) PCT Filed: Apr. 25, 2008

(86) PCT No.: PCT/JP2008/058081
§ 371 (c)(1),
(2), (4) Date: Dec. 31, 2009

(87) PCT Pub. No.: WO2008/139894
PCT Pub. Date: Nov. 20, 2008

(65) Prior Publication Data
US 2010/0130739 A1    May 27, 2010

(30) Foreign Application Priority Data
Apr. 27, 2007   (JP) ................................. 2007-118768

(51) Int. Cl.
*A01N 43/54* (2006.01)
*A61K 31/505* (2006.01)
*C07D 239/02* (2006.01)

(52) U.S. Cl.
USPC ......................................... 514/269; 544/319

(58) Field of Classification Search
USPC .......................................... 544/319; 514/269
See application file for complete search history.

(56) References Cited

U.S. PATENT DOCUMENTS

| | | | |
|---|---|---|---|
| 4,968,340 A | 11/1990 | Kaku et al. | |
| 7,205,307 B2 | 4/2007 | McNaughton-Smith et al. | |
| 2003/0181465 A1 | 9/2003 | McNaughton-Smith et al. | |
| 2009/0187025 A1 | 7/2009 | Hashimoto et al. | |

FOREIGN PATENT DOCUMENTS

| | | |
|---|---|---|
| EP | 0184257 B1 | 6/1986 |
| EP | 0400741 | 12/1990 |
| EP | 0411706 B1 | 2/1991 |
| EP | 1389616 B1 | 2/2004 |
| JP | 2085262 A | 3/1990 |
| JP | 2002-527477 | 8/2002 |
| JP | 2004-501079 | 1/2004 |
| JP | 2005-239711 A | 9/2005 |
| RU | 2320646 | 3/2008 |
| RU | 2007140675 | 5/2009 |
| WO | WO-00/23076 | 4/2000 |
| WO | WO-01/14333 A1 | 3/2001 |
| WO | WO-01/79170 A2 | 10/2001 |
| WO | WO-2004000808 A3 | 12/2003 |
| WO | WO-2005090330 A1 | 9/2005 |
| WO | WO-2007/102768 A1 | 9/2007 |

OTHER PUBLICATIONS

International Preliminary Report on Patentability issued Nov. 24, 2009, in PCT/JP2008/058081.
Edited by C.G. Wermuth, "The Practice of Medicinal Chemistry," © 1996, Academic Press Limited, pp. 211-215.
Edited by C.G. Wermuth, translated under the supervision of Hiroshi Nagase, D. Kanjo Tokatai, Saishin Soyaku Kagaku Jokan, first edition, Technomics, Inc., Aug. 15, 1998, pp. 243-248.
International Search Report mailed Jul. 29, 2008, in International Application No. PCT/JP2008/058081.
Taguchi et al., "Administration of DC34+cells after stroke enhances neurogenesis via angiogenesis in a mouse model," The Journal of Clinical Investigation, vol. 114, No. 3, Aug. 2004, pp. 330-338.
Barinaga, "Finding New Drugs to Treat Stroke," Science, vol. 272, May 3, 1996, pp. 664-666.
RN-633321138, Jan. 2, 2004.
RN-633321149, Jan. 2, 2004.
Decision on grant of patent for invention issued Jul. 20, 2012, by the Russian Federation in Russian Application No. 2009143850.

*Primary Examiner* — Paul V. Ward
(74) *Attorney, Agent, or Firm* — Drinker Biddle & Reath LLP

(57) ABSTRACT

Provided is a compound that has the ability to promote axonal outgrowth in combination with the ability to promote angiogenesis and can therefore be used to reduce central nerve injuries such as head injury and spinal cord injury, cerebral infarction, ischemic heart diseases such as myocardial infarction and organic angina, peripheral arterial occlusive diseases such as critical limb ischemia, or after-effects of these diseases. Specifically, the compound is represented by the following formula (I):

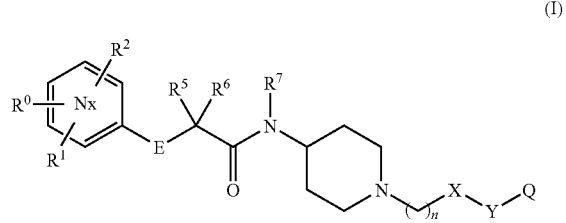

in which Nx group is preferably a 6-membered aromatic ring containing two nitrogen atoms; $R^0$, $R^1$ and $R^2$ are each independently a hydrogen atom, an alkyl group, an amino group or the like; E is an oxygen atom or an $-NR^8$ group (wherein $R^8$ is an alkyl group or the like); n is an integer of 0 to 5; X and Y are each a connecting bond, a cycloalkyl group, $-CO-$ or the like; and Q is a hydrogen atom or a phenyl group.

8 Claims, 8 Drawing Sheets

NITROGEN-CONTAINING SIX-MEMBERED AROMATIC RING DERIVATIVES AND PHARMACEUTICAL PRODUCTS CONTAINING THE SAME

CROSS REFERENCE TO RELATED APPLICATIONS

This application is a National Stage of International Application No. PCT/JP2008/058081 filed Apr. 25, 2008, and which claims benefit of Japanese Patent Application No. 2007-118768 filed Apr. 27, 2007, both of which are herein incorporated by reference in their entirety.

TECHNICAL FIELD

The present invention relates to a novel compound and a pharmaceutically acceptable salt thereof that have the ability to promote axonal outgrowth in combination with the ability to promote angiogenesis and are thus effective in reducing or treating central nerve injuries such as head injury and spinal cord injury, cerebral infarction, ischemic heart diseases such as myocardial infarction and organic angina, peripheral arterial occlusive diseases such as critical limb ischemia, or after-effects of these diseases, or other diseases against which the compounds of the present invention are considered effective.

BACKGROUND ART

Japanese Patent Application Laid-Open No. 2005-239711 (Patent Document 1) states as follows:
"The progress in the study of regulatory factors of angiogenesis has led to therapeutic applications of these factors. Among those factors known to promote angiogenesis are vascular endothelial growth factor (VEGF), basic fibroblast growth factor (bFGF) and hepatocyte growth factor (HGF). These growth factors and their genes are now being used to treat diseases that require improvement in the blood circulation (such as arteriosclerosis obliterance and ischemic heart diseases).

However, these growth factors are proteins and are therefore difficult to administer orally. They also pose other problems regarding anaphylactic responses caused by repeated administration, safety of viral vectors used in gene therapies, and side effects such as edema. Hence, there is a need for the development of new treatments."

Certain diseases are known to be caused by an organic disorder associated with neurite retraction and loss of synapses, though their etiology may vary from disease to disease. Such diseases include Alzheimer's disease, multi-infarct dementia, cerebrovascular dementia, senile dementia, Lewy body disease, Parkinson's disease and Huntington's disease.

Central nerve injuries such as cerebral hemorrhage, cerebral infarction, brain tumor, head injury and spinal cord injury can also be caused by an organic disorder associated with neurite retraction and loss of synapses.

Different medicines for these diseases have been developed that act to protect neurons by different mechanisms.

None of these medicines provide a fundamental treatment for these diseases and are less than satisfactory though they may delay the progress of the disease to some extent. In particular, there is no effective treatment for cerebral infarction that is currently used worldwide other than tissue plasminogen activator (tPA).

Although several medicines currently under development are designed to act to protect neurons, none of them are directed to actively promoting the recovery of nerve function after cerebral infarction.

Regeneration of neural stem cells has attracted much attention and many studies are being conducted in an effort to implant the cells. As far as the treatment of cerebral infarction is concerned; however, the implanted neural stem cells fail to serve as neurons to form neural networks since the neural stem cells have a small chance of survival after implantation or they may not differentiate into neurons.

Recent studies suggest that vascular remodeling such as angiogenesis is essential to the generation and regeneration, as well as to the following differentiation and maturation of neural stem cells and other cells following cerebral infarction (Non-Patent Document 1: J. Clin. Invest.,: 114, 2004). Thus, an effective treatment for cerebral infarction is required not only to provide direct protection of neurons to prevent the progress of neuronal damage, but also to promote axonal outgrowth required for regeneration/remodeling of vascular networks and reconstruction of new neural networks in the damaged ischemic penumbra (Non-Patent Document 2: Science, 3:272 (5262), p 664-666 (1996)).

Under such circumstances, a low-molecular-weight compound that can act to promote axonal outgrowth and promote angiogenesis and that can be orally administered is considered a potential drug effective in reducing or treating central nerve injuries such as head injury and spinal cord injury, cerebral infarction, ischemic heart diseases such as myocardial infarction and organic angina, peripheral arterial occlusive diseases such as critical limb ischemia, and after-effects of these diseases, as well as other diseases against which such a compound is considered effective. Such a compound is also considered a potential drug effective in reducing or treating symptoms resulting from a functional or organic disorder of the brain, including cerebral ischemic injuries, such as after-effects of cerebral infarction, cerebral hemorrhage and cerebral arteriosclerosis, as well as diseases associated with an organic disorder resulting from senile dementia, Alzheimer's disease, Parkinson's disease, and after-effects of brain injury, spinal cord injuries and brain surgery.

It is believed that the above-described compound that can promote angiogenesis would effectively act in occluded lesions found in peripheral arterial occlusive diseases, such as arteriosclerosis obliterance, Buerger's disease and Raynaud's disease. It is considered that the compound is particularly effective against critical limb ischemia and other severe symptoms against which conventional medications have no effect.

Patent Document 1: Japanese Patent Laid-Open Publication No. 2005-239711
Non-Patent Document 1: A. Taguchi, et al., J. Clin. Invest., 114:3, p 330-338 (2004)
Non-Patent Document 2: M. Barinaga, Science, 3:272 (5262), p 664-666 (1996)

DISCLOSURE OF THE INVENTION

Problems to be Solved by the Invention

Accordingly, it is an object of the present invention to provide an therapeutic agent for treating or reducing diseases including central nerve injuries such as head injury and spinal cord injury, cerebral infarction, ischemic heart diseases such as myocardial infarction and organic angina, peripheral arterial occlusive diseases such as critical limb ischemia, and after-effects of these diseases, the therapeutic agent being highly safe, having the ability to promote axonal outgrowth in combination with the ability to promote angiogenesis, and being suitable for being formed into an oral preparation such as tablets and powders, a parenteral preparation such as injections, and an external preparation such as ointments and cataplasms.

Means for Solving the Problems

To achieve the above-described object, the present invention provides a compound represented by the following formula (I):

(Chemical formula 1)

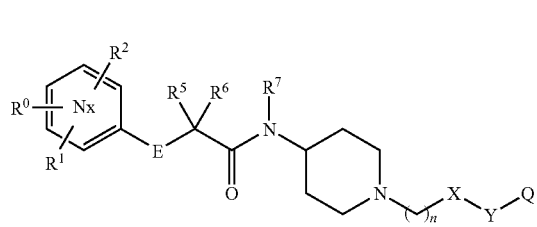

(I)

(wherein
an Nx group is a 6-membered aromatic ring containing 1 or 2 nitrogen atoms;

$R^0$, $R^1$ and $R^2$ are each independently a hydrogen atom, a halogen atom, a hydroxyl group, a straight-chain or branched alkoxy group having 1 to 5 carbon atoms, an acetyl group, a carbamoyl group, a carboxyl group, a straight-chain or branched ester group having 1 to 5 carbon atoms, an unsubstituted or halogen-substituted straight-chain, branched or cyclic alkyl group having 1 to 5 carbon atoms, or an —$NR^3R^4$ group (wherein $R^3$ and $R^4$ are each independently a hydrogen atom, an oxygen atom, an unsubstituted or halogen-substituted straight-chain, branched or cyclic alkyl group having 1 to 5 carbon atoms, or a straight-chain or branched alkyloxycarbonyl group having 2 to 10 carbon atoms);

$R^5$ and $R^6$ are each independently a hydrogen atom, or an unsubstituted or halogen-substituted straight-chain, branched or cyclic alkyl group having 1 to 5 carbon atoms;

$R^7$ is a straight-chain, branched or cyclic alkyl group having 1 to 5 carbon atoms;

E is an oxygen atom or an —$NR^8$ group (wherein $R^8$ is a hydrogen atom, or a straight-chain or branched alkyl group having 1 to 5 carbon atoms);

n is an integer of 0 to 5;

X and Y are each independently a connecting bond, a straight-chain or branched alkylene group having 1 to 5 carbon atoms, either unsubstituted or substituted with 1 to 4 hydroxyl or alkoxy groups; a cycloalkylene group having 3 to 6 carbon atoms, either unsubstituted or substituted with 1 to 4 hydroxyl groups, oxygen atoms or alkyl groups; a heterocycloalkylene group, either unsubstituted or substituted with 1 to 4 hydroxyl groups, oxygen atoms or alkyl groups; an alkenylene group having 2 to 4 carbon atoms, either unsubstituted or substituted with 1 to 4 alkyl groups having 1 to 5 carbon atoms; —NHCO—; —CONH—; —CO—; or —$SO_2$—; and Q is a hydrogen atom; a phenyl group, either unsubstituted or substituted with a halogen atom, a hydroxyl group, a straight-chain or branched alkoxy group having 1 to 5 carbon atoms, an unsubstituted or halogen-substituted straight-chain or branched alkyl group having 1 to 5 carbon atoms, a nitrile group, an amino group, a carboxyl group, a carbamoyl group, an acetyl group, a methylsulfonyl group, or a phenyl group; a thiophenyl group, either unsubstituted or substituted with a halogen atom, a hydroxyl group, a straight-chain or branched alkoxy group having 1 to 5 carbon atoms, an unsubstituted or halogen-substituted straight-chain or branched alkyl group having 1 to 5 carbon atoms, a nitrile group, an amino group, a carboxyl group, a carbamoyl group, an acetyl group, a methylsulfonyl group, or a phenyl group; a phenoxy group, either unsubstituted or substituted with a halogen atom, a hydroxyl group, a straight-chain or branched alkoxy group having 1 to 5 carbon atoms, an unsubstituted or halogen-substituted straight-chain or branched alkyl group having 1 to 5 carbon atoms, a nitrile group, an amino group, a carboxyl group, a carbamoyl group, an acetyl group, a methylsulfonyl group, or a phenyl group; a benzoyl group, either unsubstituted or substituted with a halogen atom, a hydroxyl group, a straight-chain or branched alkoxy group having 1 to 5 carbon atoms, an unsubstituted or halogen-substituted straight-chain or branched alkyl group having 1 to 5 carbon atoms, a nitrile group, an amino group, a carboxyl group, a carbamoyl group, an acetyl group, a methylsulfonyl group, or a phenyl group; a pyridyl group, either unsubstituted or substituted with a halogen atom, a hydroxyl group, a straight-chain or branched alkoxy group having 1 to 5 carbon atoms, an unsubstituted or halogen-substituted straight-chain or branched alkyl group having 1 to 5 carbon atoms, a nitrile group, an amino group, a carboxyl group, a carbamoyl group, an acetyl group, a methylsulfonyl group, or a phenyl group; a quinolyl group, either unsubstituted or substituted with a halogen atom, a hydroxyl group, a straight-chain or branched alkoxy group having 1 to 5 carbon atoms, an unsubstituted or halogen-substituted straight-chain or branched alkyl group having 1 to 5 carbon atoms, a nitrile group, an amino group, a carboxyl group, a carbamoyl group, an acetyl group, a methylsulfonyl group, or a phenyl group; an isoquinolyl group, either unsubstituted or substituted with a halogen atom, a hydroxyl group, a straight-chain or branched alkoxy group having 1 to 5 carbon atoms, an unsubstituted or halogen-substituted straight-chain or branched alkyl group having 1 to 5 carbon atoms, a nitrile group, an amino group, a carboxyl group, a carbamoyl group, an acetyl group, a methylsulfonyl group, or a phenyl group; or a benzimidazolyl group, either unsubstituted or substituted with a halogen atom, a hydroxyl group, a straight-chain or branched alkoxy group having 1 to 5 carbon atoms, an unsubstituted or halogen-substituted straight-chain or branched alkyl group having 1 to 5 carbon atoms, a nitrile group, an amino group, a carboxyl group, a carbamoyl group, an acetyl group, a methylsulfonyl group, or a phenyl group, with the proviso that when $R^7$ is a cyclopropyl group and E is an oxygen atom, Nx group is not a 3-pyridinyl group);

and a pharmaceutically acceptable salt thereof.

Effects of the Invention

The compound provided by the present invention being a nitrogen-containing 6-membered aromatic ring derivatives represented by the formula (I) are novel compounds that has the ability to promote axonal outgrowth in combination with the ability to promote angiogenesis. The compounds have proven to be highly effective and safe in various pharmacological tests and can therefore be used as a pharmaceutical product. It is also suitable for being formed into pharmaceutical preparations.

BEST MODE FOR CARRYING OUT THE INVENTION

The present invention will now be described in detail.

In compounds of the present invention represented by the formula (I), the nitrogen-containing 6-membered aromatic ring containing one nitrogen atom are serving as the Nx group may be a pyridinyl group. The nitrogen-containing 6-membered aromatic ring containing two nitrogen atoms are serving as the Nx group may be a pyrimidinyl group, a pyrazinyl group or a pyridazinyl group.

Specific examples of such nitrogen-containing 6-membered aromatic rings include 6-membered aromatic rings that may be either unsubstituted or substituted with $R^0$, $R^1$, $R^2$ and $R^{10}$ groups including the following substituents:

(Chemical formula 2)

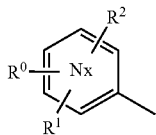

is represents following:

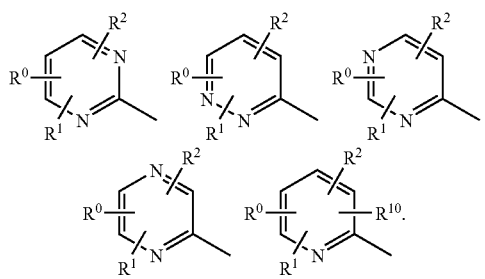

In this formula, $R^0$, $R^1$, $R^2$ and $R^{10}$ are each independently a hydrogen atom, a halogen atom, a hydroxyl group, an alkoxy group, an acetyl group, a carbamoyl group, a carboxyl group, an ester group, an unsubstituted or halogen-substituted straight-chain, branched or cyclic alkyl group having 1 to 5 carbon atoms, or an —$NR^3R^4$ group (wherein $R^3$ and $R^4$ are each independently a hydrogen atom, an oxygen atom, or an unsubstituted or halogen-substituted straight-chain, branched or cyclic alkyl or alkyloxycarbonyl group having 1 to 5 carbon atoms).

With respect to the definition of the substituents $R^0$ to $R^4$ and $R^{10}$ above, the "halogen atom" includes a fluorine atom, a chlorine atom and a bromine atom. The "alkoxy group" includes a straight-chain or branched alkoxy group having 1 to 5 carbon atoms, such as a methoxy group and an ethoxy group. The "alkyl group" includes a straight-chain or branched alkyl group having 1 to 5 carbon atoms, such as a methyl group, an ethyl group, a propyl group and a trifluoromethyl group, that may be either unsubstituted or substituted with 1 to 3 halogen atoms, such as a fluorine atom, a chlorine atom and a bromine atom.

The "ester group" includes a straight-chain or branched ester group having 1 to 5 carbon atoms, such as a methyl ester, an ethyl ester and an isopropyl ester.

The "alkyloxycarbonyl group" includes a straight-chain or branched alkyloxycarbonyl group having 2 to 10 carbon atoms, such as a methyloxycarbonyl group, an ethyloxycarbonyl group, a tert-butyloxycarbonyl group and a benzyloxycarbonyl group.

$R^5$ and $R^6$ are each independently a hydrogen atom or an unsubstituted or halogen-substituted straight-chain, branched or cyclic alkyl group having 1 to 5 carbon atoms. $R^7$ is an alkyl group.

With respect to the definition of the substituents $R^5$ and $R^6$ above, the "alkyl group" includes a straight-chain, branched or cyclic alkyl group having 1 to 5 carbon atoms, such as a methyl group, an ethyl group, a propyl group, a cyclopropyl group and a trifluoromethyl group that may be either unsubstituted or substituted with 1 to 3 halogen atoms, such as a fluorine atom, a chlorine atom and a bromine atom.

With respect to the definition of the substituent $R^7$ above, the "alkyl group" includes a straight-chain, branched or cyclic alkyl group having 1 to 5 carbon atoms, such as a methyl group, an ethyl group, a propyl group and a cyclopropyl group.

E represents an oxygen atom or an —$NR^8$ group (wherein $R^8$ is a hydrogen atom or an alkyl group).

With respect to the —$NR^8$ group, the "alkyl group" represented by $R^8$ is a straight-chain or branched alkyl group having 1 to 5 carbon atoms, such as a methyl group, an ethyl group, a propyl group and a trifluoromethyl group. The alkyl group may be substituted with 1 to 3 halogen atoms, such as a fluorine atom, a chlorine atom and a bromine atom.

X and Y are each independently a connecting bond; an alkylene group, either unsubstituted or substituted with 1 to 4 hydroxyl or alkoxy groups; a cycloalkylene group, either unsubstituted or substituted with 1 to 4 hydroxyl groups, oxygen atoms or alkyl groups; a heterocycloalkylene group, either unsubstituted or substituted with 1 to 4 hydroxyl groups, oxygen atoms or alkyl groups; an alkenylene group, either unsubstituted or substituted with 1 or 2 alkyl groups having 1 to 5 carbon atoms; —NHCO—; —CONH—; —CO—; or —$SO_2$—.

With respect to the definition of X and Y above, the alkylene group includes a straight-chain or branched alkylene group having 1 to 5 carbon atoms, such as a methylene group, a methylmethylene group, an ethylene group, a trimethylene group and a tetramethylene group.

The cycloalkylene group includes a cycloalkylene group having 3 to 6 carbon atoms, such as a 1,1-cyclopropylene group, a 1,2-cyclopropylene group, a 1,1-cyclobutylene group, a 1,2-cyclobutylene group, a 1,1-cyclopentylene group, a 1,2-cyclopentylene group, a 1,1-cyclohexylene group, a 1,2-cyclohexylene group, a 2-hydroxy-1,1-cyclopentylene group and a 3-hydroxy-1,2-cyclopentylene group.

The heterocycloalkylene group includes a heterocycloalkylene group that has 3 to 6 carbon atoms and may contain one or more oxygen or nitrogen atoms, such as a tetrahydro-2H-pyranyl group, a piperidinyl group, a piperazinyl group, a morpholinyl group, a 2-oxopyrrolidinyl group and an azetidinyl group.

The alkenylene group includes an alkenylene group having 2 to 4 carbon atoms, such as a vinylene group and a butadiene group. The alkyl group having 1 to 5 carbon atoms to serve as the substituent of the alkenylene group includes a straight-chain or branched alkyl group, such as a methyl group, an ethyl group, a propyl group and an isopropyl group.

The "connecting bond" as used herein means a direct bond. Specifically, given that "X" and "Y" are each a connecting bond, the two adjacent substituents of "X" and "Y" are directly bonded with each other: Neither "X" nor "Y" exists as a group.

The substituent "Q" is as defined above. Preferably, the substituents of the phenyl group, thiophenyl group, phenoxy group, benzoyl group, pyridyl group, quinolyl group, isoquinolyl group or benzimidazolyl group include a halogen atom, such as a fluorine atom, a chlorine atom and a bromine atom; a hydroxyl group; a straight-chain or branched alkoxy group having 1 to 5 carbon atoms, such as a methoxy group and an ethoxy group; a straight-chain or branched alkyl group having 1 to 5 carbon atoms substituted with 1 to 3 halogen atoms; a nitrile group; an amino group; a carboxyl group; a carbamoyl group; an acetyl group; and a methylsulfonyl group.

The halogen atom in the halogen-substituted straight-chain or branched-alkyl group having 1 to 5 carbon atoms includes a fluorine atom, a chlorine atom and a bromine atom.

Although the compounds of the present invention are novel compounds, compounds having a partly similar skeleton are described, for example, in Published Japanese Translation of PCT International Application No. 2003-507456, WO 01/79170 and WO 00/23076. As opposed to the compounds described in Published Japanese Translation of PCT International Application No. 2003-507456, which act as a modulator of chemokine receptor activity, the compounds described in Examples 65, 85, 91, 102, 109, 130 and 135 of the present invention exhibit an affinity to chemokine receptor CCR3 of 0.0, 2.4, 18, 0.0, 16, 3.5 and 22% at a concentration of 10 μM, respectively, showing no affinity to chemokine receptor CCR3. This suggests that the compounds of the present invention do not cause possible side effects that may be associated with chemokine receptor.

The compounds of the present invention represented by the general formula (I) may exist as isomers (such as tautomers, enantiomers, geometrical isomers or diastereomers). The present invention therefore encompasses any such isomers and mixtures containing these isomers in any proportions.

The compounds of the present invention represented by the general formula (I) can be obtained by using a known method or any suitable combination of known methods.

Specifically, the compounds can be obtained by the following reaction processes (a), (b), (c) or (d).

(a) The compounds can be produced by reacting a compound of the following general formula (IV-b):

(Chemical formula 3)

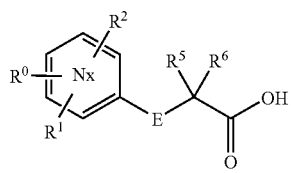

(IV-b)

with a compound of the following general formula (V)

(Chemical formula 4)

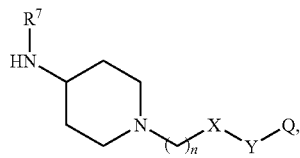

(V)

or a salt thereof.

(b) Or, the compounds can be obtained by reacting a compound of the following general formula (II-b):

(Chemical formula 5)

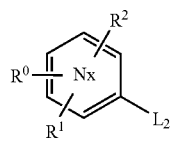

(II-b)

with a compound of the following general formula (VI):

(Chemical formula 6)

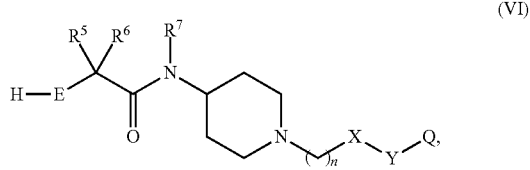

(VI)

or a salt thereof.

(c) Or, the compounds can be obtained by reacting a compound of the following general formula (VII):

(Chemical formula 7)

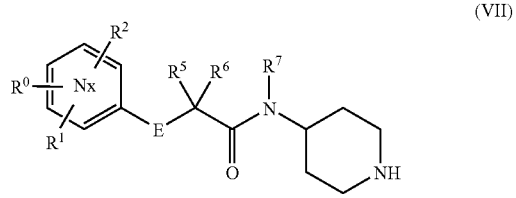

(VII)

with a compound of the following general formula (VIII):

(Chemical formula 8)

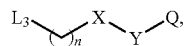

(VIII)

or a salt thereof.

(d) Or, the compounds can be obtained by reacting a compound of the following general formula (II-a):

(Chemical formula 9)

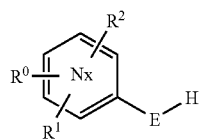

(II-a)

with a compound of the following general formula (IX):

(Chemical formula 10)

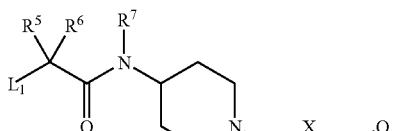

(IX)

Each of the compounds of the formulas (II-a) to (IX) shown above is commercially available or can be easily obtained by a known method.

It should be appreciated by those skilled in the art that the functional groups such as hydroxyl groups and amino groups of the starting reagents or intermediate compounds of the process of the present invention may be protected by a protective group and the production of the compounds of the formula (I) involves addition of one or more such protective groups at a suitable point and removal of the protective group at a suitable point of any subsequent processes.

Methods for the protection and deprotection of functional groups are described, for example, in *Protective Groups in Organic Chemistry*, J. W. F. McOmie ed., Plenum Press (1973), *Protective Groups in Organic Synthesis,* 2nd edition, T. W. Greene and P. G. M. Wuts, Wiley-Interscience (1991), and *Greene's Protective Groups in Organic Synthesis* 4th. Edition; T. W. Greene and P. G. M. Wuts, Wiley-Interscience (2006).

The protective group for a functional hydroxyl group may be any protective group commonly used to protect a hydroxyl group. Examples of the protective groups include an alkoxycarbonyl group, such as benzyloxycarbonyl, 4-nitrobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2-(trimethylsilyl)ethoxycarbonyl, vinyloxycarbonyl and allyloxycarbonyl; an acyl group, such as acetyl, formyl, chloroacetyl, dichloroacetyl, trichloroacetyl, trifluoroacetyl, methoxyacetyl, phenoxyacetyl, pivaloyl and benzoyl; a lower alkyl group, such as methyl, tert-butyl, 2,2,2-trichloroethyl and 2-trimethylsilylethyl; an aryl lower alkyl group, such as benzyl, 4-methoxybenzyl, 3,4-dimethoxybenzyl and trityl; a lower alkenyl group, such as allyl; a lower alkynyl group, such as propargyl; a nitrogen- or sulfur-containing heterocyclic ring group, such as tetrahydrofuryl, tetrahydropyranyl and tetrathiopyranyl; a lower alkoxy or alkylthioalkyl group, such as methoxymethyl, methylthiomethyl, benzyloxymethyl, 2-methoxyethoxymethyl, 1-ethoxyethyl and 1-methylmethoxyethyl; a lower alkyl or arylsulfonyl group, such as methanesulfonyl and p-toluenesulfonyl; and a substituted silyl group, such as trimethylsilyl, triethylsilyl, triisopropylsilyl, tert-butyldimethylsilyl and tert-butyldiphenylsilyl.

The protective group for an amino group may be any protective group commonly used to protect an amino group. Examples thereof include an alkoxycarbonyl group, such as benzyloxycarbonyl, 4-nitrobenzyloxycarbonyl, 4-methoxybenzyloxycarbonyl, 3,4-dimethoxybenzyloxycarbonyl, methoxycarbonyl, tert-butoxycarbonyl, 1,1-dimethylpropoxycarbonyl, 2,2,2-trichloroethoxycarbonyl, 2-(trimethylsilyl)ethoxycarbonyl, 9-fluorenylmethyloxycarbonyl, vinyloxycarbonyl and allyloxycarbonyl; an acyl group, such as acetyl, formyl, chloroacetyl, dichloroacetyl, trichloroacetyl, trifluoroacetyl, phenylacetyl, phthaloyl, succinyl, alanyl, leucyl and benzoyl; an aryl lower alkyl group, such as benzyl, 4-methoxybenzyl, 3,4-dimethoxybenzyl, diphenylmethyl and trityl; an arylthio group, such as 2-nitrophenylthio and 2,4-dinitrophenylthio; a lower alkyl or arylsulfonyl group, such as methanesulfonyl and p-toluenesulfonyl; a di-lower-alkylamino-lower alkylidene group, such as N,N-dimethylaminomethylene; an aryl-lower-alkylidene group, such as benzylidene, 2-hydroxybenzylidene and 2-hydroxy-5-chlorobenzylidene; a nitrogen-containing heterocyclic alkylidene group, such as 3-hydroxy-4-pyridylmethylene; a cycloalkylidene group, such as cyclohexylidene, 2-ethoxycarbonylcyclohexylidene and 2-ethoxycarbonylcyclopentylidene; a phosphoryl group, such as diphenylphosphoryl; and a substituted silyl group, such as trimethylsilyl.

The compounds and intermediates of the present invention can be isolated from the reaction mixture using standard methods and, if necessary, may further be purified.

Each of the reaction processes will now be described in detail.

[Reaction Process (a)]

This reaction process is specifically shown by the following reaction scheme:

(Chemical formula 11)

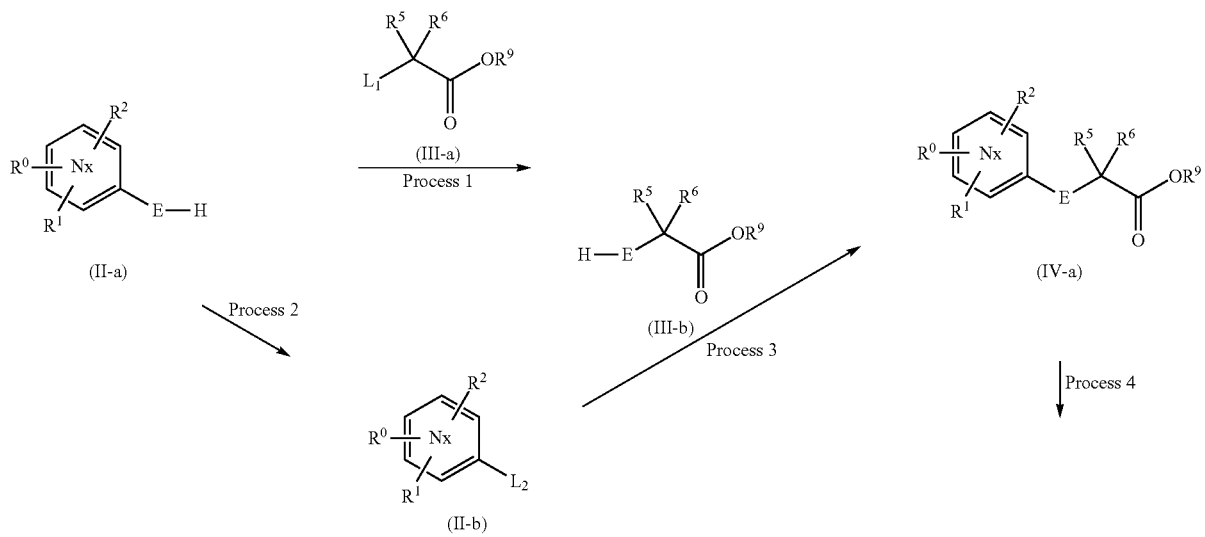

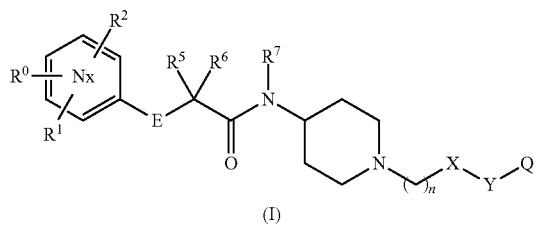 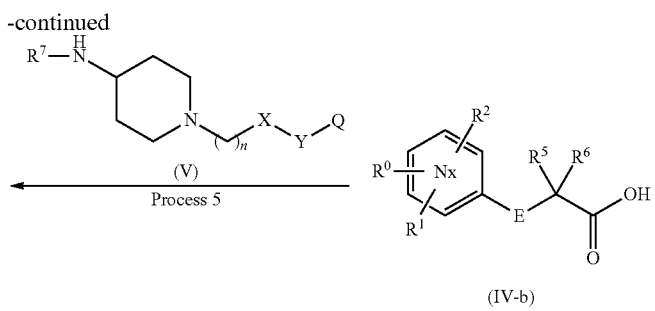

In the reaction scheme above, $R^0$ to $R^7$, E, Nx, n, X, Y and Q are as described above.

The substituent $R^9$ is an alkyl group, such as a methyl group, an ethyl group, a tert-butoxy group and a benzyl group. The substituents $L_1$ and $L_2$ are each a leaving group that can be easily replaced with an amino group or a hydroxyl group. Specific examples thereof include a halogen atom, such as a chlorine atom, a bromine atom and an iodine atom; an alkylsulfonyloxy group, such as a methanesulfonyloxy group and a trifluoromethanesulfonyloxy group; and an arylsulfonyloxy group, such as a p-toluenesulfonyloxy group and 3-nitrobenzenesulfonyloxy group.

The present process essentially involves the reaction of a compound (II-a) with an ester derivative (III-a) to give a compound (IV-a), which in turn is hydrolyzed to produce a carboxylic compound (IV-b). Subsequently, the resulting compound (IV-b) is subjected to a condensation reaction with an amine derivative (V) to give a desired compound (I), which forms one aspect of the present invention.

Alternatively, the compound (IV-a) may be obtained by converting the compound (II-a) into the compound (II-b) followed by reacting it with an ester derivative (III-b).

When it is necessary to protect functional groups, such as a hydroxyl group and an amino group, in this reaction process, the process may include a process for adding one or more such protective groups at a suitable step and a removal process of the protective group at a subsequent step.

For example, when $R^0$ in the compound (I) is an —$NR^3R^4$ with $R^3$ or $R^4$ being a methyloxycarbonyl group, an ethyloxycarbonyl group, a tert-butyloxycarbonyl group, a benzyloxycarbonyl group, a benzyl group or each an oxygen atom to serve as a protective group on the nitrogen atom, the protective group may be removed or converted into other functional groups to give the desired compound (I) that has $R^3$ and/or $R^4$ converted into a hydrogen atom. This reaction process can be involved in the present reaction processes.

The respective processes are described in further detail in the following.

Process 1:

The compounds of the formula (II-a) and the ester derivatives of the formula (III-a) to serve as the starting material of the present process are commercially available ones or they may be obtained by using known methods.

The compound (II-a) can be obtained according to a method or a suitable combination of methods or by applying methods described, for example, in *Heterocyclic Compound New Edition, Introduction*, Yamanaka Hiroshi, Sakamoto Norio et al., Kodansha Scientific (2004), and *Heterocyclic Compound New Edition, Application*, Yamanaka Hiroshi, Sakamoto Norio et al., Kodansha Scientific (2004).

Examples of the ester derivative (III-a) include ethyl bromoacetate, ethyl 2-bromopropionate and ethyl 2-bromo-2-methylpropionate.

In the present process, as a first step thereof the compound (II-a) is reacted with the ester derivative (III-a) to give the compound (IV-a).

The reaction can be carried out by mixing the compound (II-a) with 1.0 to 1.5 equivalents of the ester derivative (III-a) at −20° C. to 150° C., and preferably at 0° C. to 100° C., in an inert solvent, such as benzene, toluene, tetrahydrofuran, dioxane, dimethylformaldehyde, dimethyl sulfoxide, acetonitrile, acetone, methanol, ethanol, isopropyl alcohol, tert-butyl alcohol, diethyl ether, ethylene glycol, methylene chloride or chloroform, and if necessary, in the presence of an organic base, such as triethylamine, diisopropylethylamine or pyridine, or an inorganic base, such as sodium, sodium hydride, potassium, potassium hydride, sodium ethoxide, potassium tert-butoxide, sodium carbonate, potassium carbonate, cesium carbonate, cesium fluoride, sodium bicarbonate or potassium bicarbonate.

If necessary, the reaction may use a combination of organic bases and inorganic bases. Alternatively, sodium iodide, potassium iodide, tetrabutylammonium iodide or crown ether may be added.

Processes 2 and 3

These processes are used as an alternative process for synthesizing the compound (IV-a). Specifically, the compound (II-b) is first converted from the compound (II-a), and the resulting product is reacted with the ester derivative (III-b) to give the compound (IV-a).

The conversion of the compound (II-a) (Process 2) may be carried out by various methods depending on the type of the substituent $L_2$ of the compound (II-b). For example, when $L_2$ is a halogen atom, such as a chlorine atom and a bromine atom, the compound (II-a) is reacted in the presence of both phosphorous oxychloride ($POCl_3$) and phosphorus pentachloride ($PCl_5$) or in the presence of one of phosphorus oxychloride, phosphorus pentachloride, phosphorus oxybromide ($POBr_3$), phosphorus pentabromide ($PBr_5$), and the like. If necessary, the reaction may be carried out in an inert solvent, such as benzene, toluene, ethyl acetate, dioxane, chloroform or methylene chloride.

When the leaving group $L_2$ is an alkylsulfonyloxy group, such as a methanesulfoyloxy group or a trifluoromethanesulfonyloxy group; or an arylsulfonyloxy group, such as a p-toluenesulfonyloxy group or a 3-nitrobenzenesulfonyloxy group, the reaction is carried out by mixing the compound (II-a) with 1.0 to 1.5 equivalents of methanesulfonyl chloride (MsCl), p-toluenesulfonyl chloride (TsCl) or trifluoromethanesulfonic anhydride (Tf$_2$O) at −20° C. to 150° C., and preferably at 0° C. to 100° C., in an inert solvent, such as toluene, ethyl acetate, tetrahydrofuran, dioxane, chloroform or acetonitrile, and if necessary, in the presence of an organic base, such as triethylamine, diisopropylethylamine or pyridine, or an inorganic base, such as sodium, sodium hydride, potassium, potassium hydride, sodium ethoxide, potassium tert-butoxide, sodium carbonate, potassium carbonate, cesium carbonate, cesium fluoride, sodium bicarbonate or potassium bicarbonate.

While the resulting compound may be directly used in the subsequent process, it may be purified as desired by a known purification method, such as recrystallization and column chromatography, prior to the subsequent process.

The compound (II-b) produced as described above is then reacted with the ester derivative (III-b) to be derivatized into the compound (IV-a) (Process 3).

The reaction can be carried out by mixing the compound (II-b) with 1.0 to 1.5 equivalents of the ester derivative (III-b) at −20° C. to 150° C., and preferably at 0° C. to 100° C., in an inert solvent, such as benzene, toluene, tetrahydrofuran, dioxane, dimethylformaldehyde, dimethyl sulfoxide, acetonitrile, acetone, methanol, ethanol, isopropyl alcohol, tert-butyl alcohol, diethyl ether, ethylene glycol, methylene chloride or chloroform, and if necessary, in the presence of an organic base, such as triethylamine, diisopropylethylamine or pyridine, or an inorganic base, such as sodium, sodium hydride, potassium, potassium hydride, sodium ethoxide, potassium tert-butoxide, sodium carbonate, potassium carbonate, cesium carbonate, cesium fluoride, sodium bicarbonate or potassium bicarbonate.

If necessary, sodium iodide, potassium iodide, tetrabutylammonium iodide or crown ether may be added to the reaction.

The compound (III-b) for use in the reaction may be a commercial product or a known compound, or alternatively, can be easily synthesized by known methods.

Specific examples of such compounds (III-b) include glycolic acid, methyl glycolate, ethyl glycolate, tert-butyl glycolate, benzyl glycolate, lactic acid, methyl lactate, ethyl lactate, tert-butyl lactate, benzyl lactate, 2-hydroxyisobutyric acid, methyl 2-hydroxyisobutyrate, ethyl 2-hydroxyisobutyrate, tert-butyl 2-hydroxyisobutyrate, glycine, glycine methyl ester, glycine ethyl ester, glycine tert-butyl ester, glycine benzyl ester, sarcosine, sarcosine methyl ester, sarcosine ethyl ester, sarcosine methyl ester, alanine, alanine methyl ester, alanine ethyl ester, alanine tert-butyl ester, alanine benzyl ester, N-methylalanine, 2-aminoisobutyric acid, methyl 2-aminoisobutyrate, ethyl 2-aminoisobutyrate, tert-butyl 2-aminoisobutyrate, benzyl 2-aminoisobutyrate and 2-(methylamino)isobutyric acid.

Processes 4 and 5:

The compound (IV-a) produced as described above is hydrolyzed by a known method (Process 4) to be converted into the carboxylic acid (IV-b), which in turn is subjected to amide condensation with the amine derivative (V) to give the amide (I).

The compound (V) that can be used in the condensation reaction with the compound (IV-b) may be a known compound, or alternatively, can be easily synthesized by known methods.

The conditions for the amidation reaction may be based on the methods described in Compendium for Organic Synthesis (Wiley-Interscience: A Division of John Wiley & Sons).

For example, the carboxylic acid derivative (IV-b) is treated with diethyl phosphorocyanidate (DSPC), diphenyl phosphorazidate (DPPA), dicyclohexylcarbodiimide (DCC), 1-ethyl-3-(3-dimethylaminopropyl)carbodiimide hydrochloride, 2-iodo-1-methyl pyridinium, propanephosphonic acid anhydride, 2-chloro-1,3-dimethylimidazolinium chloride, 2-chloro-1,3-dimethylimidazolinium hexafluorophosphate or benzotriazole-1-yl-oxy-tris-(dimethylamino)phosphonium hexafluorophosphate (BOP reagent). When necessary, the reaction may be carried out in the presence of an organic or inorganic base. The amine derivative (V) is added either subsequently or prior to the reaction to give the amide (I). Alternatively, the carboxylic acid derivative (IV-b) may be converted into an active ester compound, such as an acid halide, a symmetric acid anhydride or a mixed acid anhydride, which in turn is reacted with the amine derivative (V) to give the amide derivative (I).

When $R^0$ in the resulting amide derivative (I) is an —$NR^3R^4$ and $R^3$ or $R^4$ is a methyloxycarbonyl group, an ethyloxycarbonyl group, a tert-butyloxycarbonyl group, a benzyloxycarbonyl group, a benzyl group or each an oxygen atom to serve as a protective group on the nitrogen atom, the protective group may be eliminated or converted into other functional groups to obtain the desired compound (I) that has $R^3$ and/or $R^4$ converted into a hydrogen atom. This may be an alternative reaction process.

The reaction may be carried out by different methods depending on the type of the protective groups on the nitrogen atom of the compound (I). For example, a compound (I) in which $R^0$ is an —$NR^3R^4$ group with $R^3$ or $R^4$ being a benzyl group, a 4-methoxybenzyl group or a benzyloxycarbonyl group or $R^3$ and $R^4$ each being an oxygen atom, together forming a nitro group, may be hydrogenated in the presence of a catalyst, such as palladium carbon, palladium hydroxide on carbon, platinum or platinum oxide, in an inert solvent, such as methanol, ethanol, isopropyl alcohol, toluene, ethyl acetate, tetrahydrofuran, dioxane, chloroform or acetic acid. Alternatively, the compound (I) may be reduced under an acidic condition using zinc or tin chloride.

A compound (I) in which the protective group $R^3$ or $R^4$ is a tert-butoxycarbonyl group, an ethoxycarbonyl group, a 4-methoxybenzyl group, a 3,4-dimethoxybenzyl group, an acetyl group or a formyl group may be subjected to deprotection by treating with an acid, such as trifluoroacetic acid, hydrochloric acid, hydrobromic acid or sulfuric acid, in an inert solvent, such as methanol, ethanol, isopropyl alcohol, toluene, ethyl acetate, tetrahydrofuran, dioxane, chloroform or acetonitrile.

When necessary, the resulting compound (I) may be purified by a known purification method, such as recrystallization or column chromatography.

[Reaction Process (b)]

The present process is specifically shown by the following chemical reaction scheme:

(Chemical formula 12)

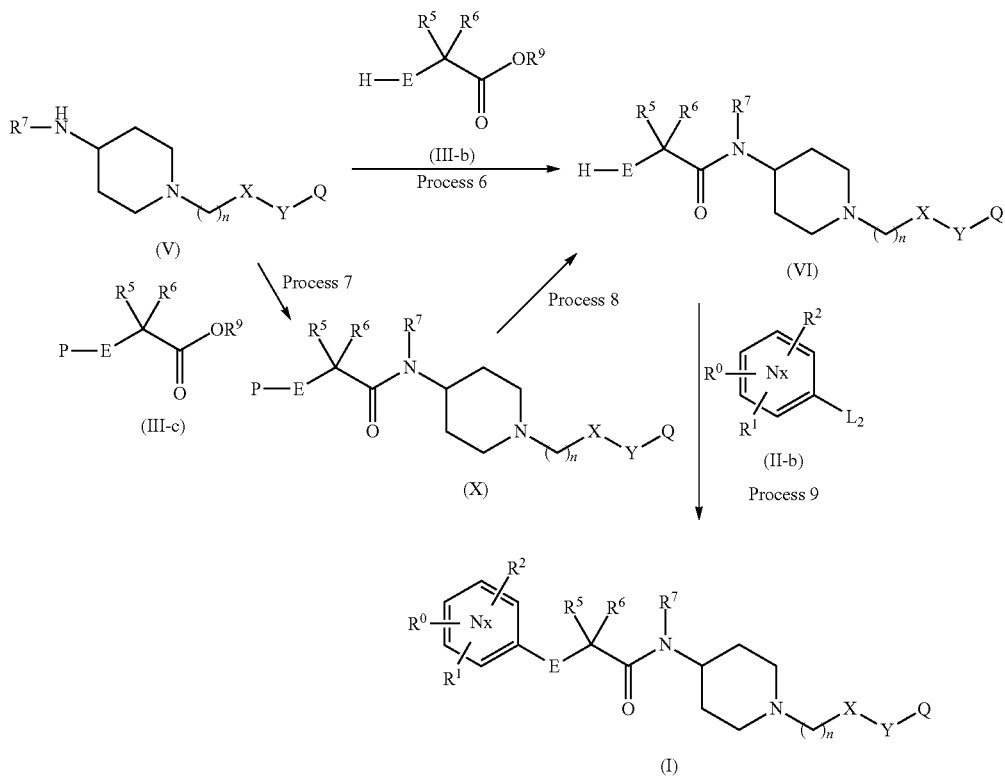

In the reaction scheme above, $R^0$ to $R^2$, $R^5$ to $R^7$, E, Nx, n, X, Y, $L_2$ and Q are as described above. The substituent $R^9$ is a hydrogen atom and P is a protective group.

Examples of the protective group include a benzyl group, a p-methoxybenzyl group, a tent-butoxycarbonyl group, an ethoxycarbonyl group, a benzyloxycarbonyl group and a p-methoxybenzyloxycarbonyl group.

Specifically, a compound (V) is reacted with an ester derivative (III-b) to produce a compound (VI).

In an alternative process for synthesizing the compound (VI), the compound (V) is reacted with an ester derivative (III-c) to give a compound (X), which in turn is converted into the compound (VI).

Subsequently, the resulting compound (VI) is reacted with a compound (II-b) to give a desired compound (I), which forms one aspect of the present invention.

When $R^0$ in the resulting amide derivative (I) is an —$NR^3R^4$ with $R^3$ or $R^4$ being a methyloxycarbonyl group, an ethyloxycarbonyl group, a tert-butyloxycarbonyl group, a benzyloxycarbonyl group or a benzyl group or each an oxygen atom to serve as a protective group on the nitrogen atom, the protective group may be eliminated or converted into other functional groups to give the desired compound (I) that has $R^3$ and/or $R^4$ converted into a hydrogen atom. This may be an alternative reaction process.

These respective processes are described in further detail in the following.

Processes 6 and 7:

The compound (III-b) or (III-c) to serve as the starting material of the present process are commercially available ones, or they may be obtained by using known methods.

In the present process, as a first step thereof, the carboxylic acid (III-b) or (III-c) is subjected to amide condensation with the amine derivative (V) to give the amide (VI) or (X), respectively.

The conditions for the amidation reaction may be based on the methods described in Compendium for Organic Synthesis (Wiley-Interscience: A Division of John Wiley & Sons).

For example, the carboxylic acid derivative (III-b) or (III-c) is treated with diethyl phosphorocyanidate (DEPC), diphenyl phosphorazidate (DPPA), dicyclohexylcarbodiimide (DCC), 1-ethyl-3-(3-dimethylaminopropyl)carbodiimide hydrochloride, 2-iodo-1-methyl pyridinium, propanephosphonic acid anhydride, 2-chloro-1,3-dimethylimidazolinium chloride, 2-chloro-1,3-dimethylimidazolinium hexafluorophosphate or benzotriazole-1-yl-oxy-tris-(dimethylamino)phosphonium hexafluorophosphate (BOP reagent). When necessary, the reaction may be carried out in the presence of an organic or inorganic base. The amine derivative (III) is added either subsequently or prior to the reaction to obtain the amide (VI) or (X).

Alternatively, the carboxylic acid derivative (III-b) or (III-c) may be converted into an active ester compound, such as an acid halide, a symmetric acid anhydride or a mixed acid anhydride, which in turn is reacted with the amine derivative (V) to give the amide (VI) or (X), respectively.

Process 8:

When the resulting product is the compound (X), it is subjected to deprotection and converted into the compound (VI).

The deprotection may be carried out by different methods depending on the type of the protective group P of the compound (X). For example, when P is a benzyl group, a 4-methoxybenzyl group or a benzyloxycarbonyl group, the compound (X) is hydrogenated in the presence of a catalyst, such as palladium carbon, palladium hydroxide on carbon, platinum or platinum oxide, in an inert solvent, such as methanol, ethanol, isopropyl alcohol, toluene, ethyl acetate, tetrahydrofuran, dioxane, chloroform or acetic acid. When the protective group P is a tert-butoxycarbonyl group, an ethoxycarbonyl group, a 4-methoxybenzyl group or a 3,4-dimethoxybenzyl group, the compound (X) is deprotected by treating with an acid, such as trifluoroacetic acid, hydrochloric acid, hydrobromic acid or sulfuric acid, in an inert solvent, such as methanol, ethanol, isopropyl alcohol, toluene, ethyl acetate, tetrahydrofuran, dioxane, chloroform or acetonitrile.

While the resulting compound may be directly used in the subsequent process, it may be purified as desired by a known converted into other functional groups so that the amide derivative (I) can be converted into the compound represented by the formula (I), which is the compound of the present invention.

In this reaction, the compound (I) can be synthesized in the same manner as in the reaction process (a).

When necessary, the compounds obtained in the above-described reactions may be purified by a known purification method, such as recrystallization and column chromatography.

[Reaction Process (c)]

The present process is specifically shown by the following chemical reaction scheme:

(Chemical formula 13)

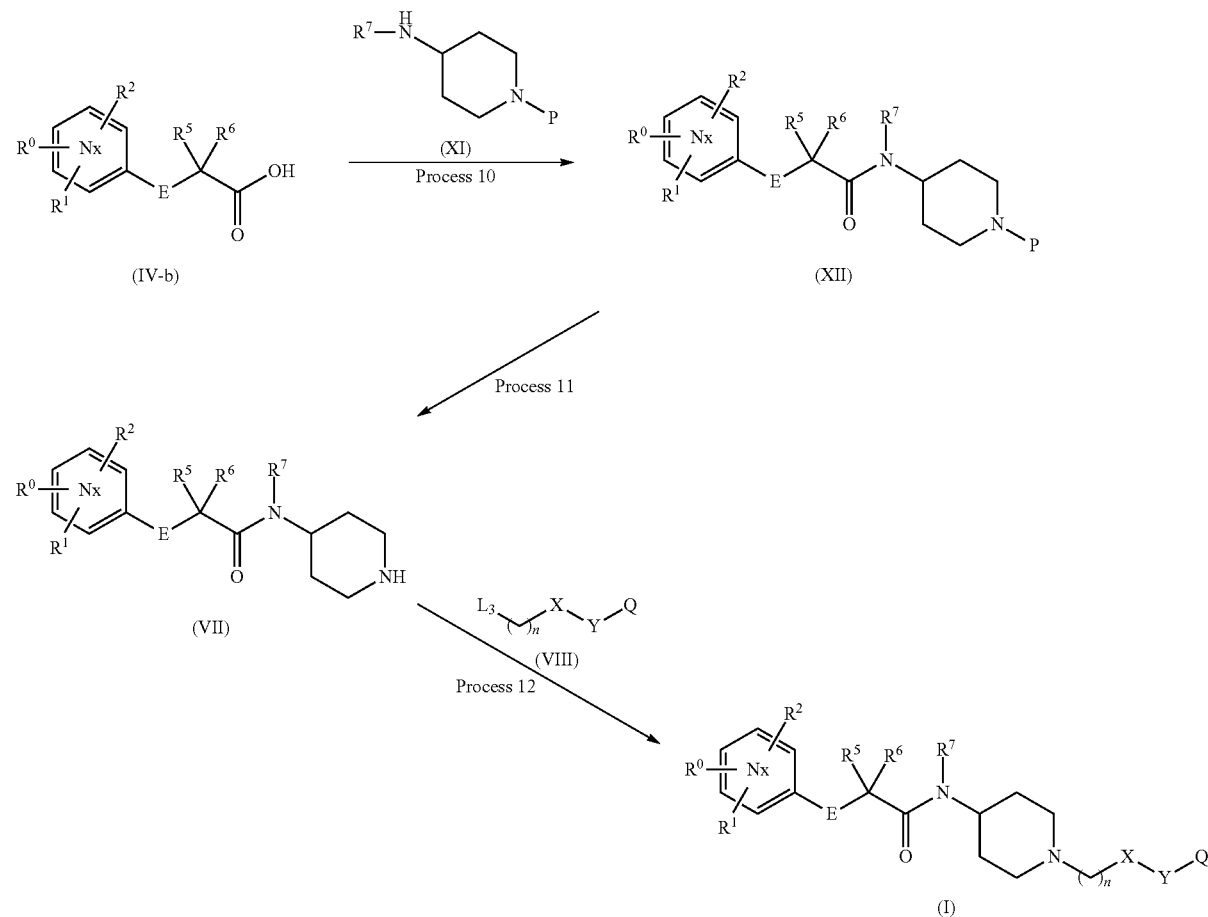

purification method, such as recrystallization and column chromatography, prior to the subsequent process.
Process 9:

The compound (VI) produced as described above is reacted with the compound (II-b) to give the compound represented by the formula (I), which is the compound of the present invention.

The compound (II-b) used in the present process is as described in the process 2. In this reaction, the compound (I) can be synthesized in the same manner as in the process 3.

When necessary, the protective group on the nitrogen atom of the resulting amide derivative (I) may be eliminated or In the reaction scheme above, $R^0$ to $R^2$, $R^5$ to $R^7$, E, Nx, n, X, Y and Q are as described above and P is a protective group.

Examples of the protective group include a benzyl group, a p-methoxybenzyl group, a tert-butoxycarbonyl group, an ethoxycarbonyl group, a benzyloxycarbonyl group and a p-methoxybenzyloxycarbonyl group.

The substituent $L_3$ is a leaving group that can be easily replaced by an amino group. Specific examples thereof include a halogen atom, such as a chlorine atom, a bromine atom and an iodine atom; an alkylsulfonyloxy group, such as a methanesulfonyloxy group and a trifluoromethanesulfonyloxy group; and an arylsulfonyloxy group, such as a p-toluenesulfonyloxy group and 3-nitro-benzenesulfonyloxy group.

The present process specifically involves condensation of the carboxylic acid derivative (IV-b) described in the above process 4 with a compound (XI) to give an amide compound (XII). The amide compound (XII) is then deprotected to produce a compound (VII). The resulting compound (VII) is subsequently reacted with a compound (VIII) to give the desired compound (I).

These processes are described in further detail in the following.

Process 10:

The compound (XI) to serve as the starting material of the present process may be a commercial product, may be known from literature (*J. Med. Chem.*, 36: 3707 (1993) [R. H. Mach et al.], EP 0184257-A1 [R. A. Stokbroekx et al.]), or may be produced by a known method.

The amidation to afford the compound (XII) can be carried out in the same conditions as in the process 5.

Process 11:

The compound (XII) produced above is subjected to a deprotection reaction to give the compound (VII).

This reaction can be carried out in the same manner as in the process 8 to synthesize the compound (VII).

ride, chloroform or carbon tetrachloride, in the presence of an organic base, such as triethylamine, diisopropylethylamine or pyridine, or an inorganic base, such as sodium, sodium hydride, potassium, potassium hydride, sodium ethoxide, sodium tert-butoxide, sodium carbonate, potassium carbonate, cesium carbonate, cesium fluoride, sodium bicarbonate or potassium bicarbonate.

If necessary, sodium iodide, potassium iodide, tetrabutylammonium iodide or crown ether may be added to the reaction.

When necessary, the protective group on the nitrogen atom of the resulting amide derivative (I) may be removed or converted into other functional groups so that the amide derivative (I) can give the compound represented by the formula (I), which is the compound of the present invention.

The reaction can be carried out in the same manner as described in the reaction process (a) to synthesize the compound (I).

When necessary, the compounds obtained in the above-described reactions may be purified by a known purification method, such as recrystallization and column chromatography.

[Reaction Process (d)]

The present process is specifically shown by the following chemical reaction scheme:

(Chemical formula 14)

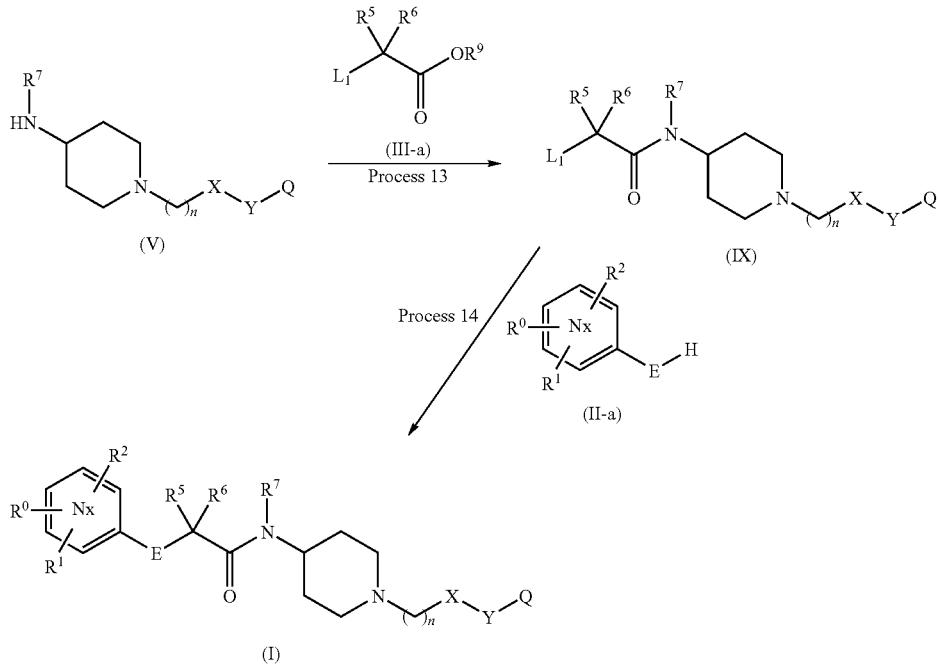

Process 12:

The compound (VII) produced in the above process 11 is reacted with the compound (VIII) to give the compound represented by the formula (I), which is the compound of the present invention.

Specifically, in the present process the compound (VII) is reacted with 1.0 to 1.5 equivalents of the compound (VIII) at about −50° C. to about 120° C., and preferably at about −20° C. to about 80° C., in an inert solvent, such as benzene, toluene, tetrahydrofuran, dioxane, dimethylformamide, dimethyl sulfoxide, acetonitrile, acetone, ether, methylene chlo- In the reaction scheme above, $R^0$ to $R^2$, $R^5$ to $R^7$, E, Nx, n, X, Y, $L_3$ and Q are as described above and the substituent $R^9$ is a hydrogen atom.

The present process specifically involves condensation of a compound (V) with a compound (III-a) to give an amide compound (IX). The obtained compound (IX) is then reacted with a compound (II-a) to give the desired compound (I).

These processes are described in further detail in the following.

Process 13:

In the present process, as a first step, the carboxylic acid (III-a) is subjected to amide condensation with the amine derivative (V) to give the amide (IX).

The amidation reaction can be carried out in the same manner as in the process 5 to synthesize the compound (IX).

Process 14:

In the present process 14, the compound (IX) produced in the above process 13 is reacted with the compound (II-a) to give the compound represented by the formula (I), the desired compound of the present invention.

The reaction can be carried out in the same manner as in the process 1 to synthesize the compound (I).

When necessary, the protective group on the nitrogen atom of the resulting amide derivative (I) may be removed or converted into other functional groups so that the amide derivative (I) can give the compound represented by the formula (I), which is the compound of the present invention.

The reaction can be carried out in the same manner as described in the reaction process (a) to synthesize the compound (I).

When necessary, the compounds obtained in the above-described reactions may be purified by a known purification method, such as recrystallization and column chromatography.

Isomers present in the compound of the present invention represented by the general formula (I) can be separated by using a known method, such as recrystallization, column chromatography, thin layer chromatography and high performance liquid chromatography, or a similar method using optically active reagents.

The compounds of the present invention represented by the general formula (I) may be formed into corresponding salts by dissolving them in a suitable organic solvent, such as water, methanol, ethanol, isopropanol, diethyl ether, diisopropyl ether, tetrahydrofuran, methylene chloride, chloroform, benzene or toluene, and treating with an inorganic or organic acid.

The inorganic acids used for this purpose include hydrochloric acid, hydrobromic acid, sulfuric acid, nitric acid, phosphoric acid and periodic acid. The organic acids include formic acid, acetic acid, butyric acid, oxalic acid, malonic acid, propionic acid, valeric acid, succinic acid, fumaric acid, maleic acid, tartaric acid, citric acid, malic acid, benzoic acid, benzenesulfonic acid, p-toluenesulfonic acid, methanesulfonic acid and ethanesulfonic acid.

The compounds of the present invention represented by the general formula (I) and salts thereof exhibit decreased toxicity. In an experiment in which a compound of Example 65 of the present invention was orally administered repeatedly to rats once a day for one week, the compound did not exhibit toxicity at a dose of 150 mg/kg/day.

While the compounds of the present invention represented by the general formula (I) and salts thereof may be used by themselves, they may be formulated as desired with other pharmaceutically acceptable, commonly used carriers into a pharmaceutical preparation that is intended to reduce or treat diseases including central nerve injuries such as head injury and spinal cord injury, cerebral infarction, ischemic heart diseases such as myocardial infarction and organic angina, peripheral arterial occlusive diseases such as critical limb ischemia, and after-effects of these diseases, by promoting axonal outgrowth and promoting angiogenesis. The preparation can be prepared by using a filler, an expander, a binder, a moisturizer, a disintegrating agent, a surfactant, a lubricant and other commonly used diluents and excipients. The pharmaceutical preparation may be provided in different forms depending on the purpose of treatment, including tablets, pills, powders, liquids, suspensions, emulsions, granules, capsules, suppositories, injections (such as liquids and suspensions), ointments, cataplasms, inhalants and other suitable forms.

Tablets can be formed by using an excipient, such as lactose, sucrose, sodium chloride, glucose, urea, starch, calcium carbonate, kaolin, crystalline cellulose and silicic acid; a binder, such as water, ethanol, propanol, simple syrup, a glucose solution, a starch solution, a gelatin solution, carboxymethyl cellulose, shellac, methyl cellulose, potassium phosphate and polyvinyl pyrrolidone; a disintegrating agent, such as dry starch, sodium alginate, agar powder, laminaran powder, sodium bicarbonate, calcium carbonate, polyoxyethylene sorbitan fatty acid esters, sodium lauryl sulfate, stearic acid monoglyceride, starch and lactose; an anti-disintegration agent, such as sucrose, stearin, cocoa butter and a hydrogenated oil; an absorption-promoting agent, such as a quaternary ammonium base and sodium lauryl sulfate; a humectant, such as glycerol and starch; a moisturizer, such as glycerin and starch; an adsorbent, such as starch, lactose, kaolin, bentonite and colloidal silicic acid; a lubricant, such as purified talc, a stearate, boric acid powder and polyethylene glycol; and other carriers.

When necessary, tablets may be formed by applying a known coating, such as sugar coating, gelatin coating, enteric coating, film coating, or alternatively, tablets may be formed into double-layered pills or multi-layered pills.

Pills can be formed by using an excipient, such as glucose, lactose, starch, cacao butter, hydrogenated vegetable oil, kaolin and talc; a binder, such as powdered gum Arabic, powdered tragacanth, gelatin and ethanol; a disintegrating agent, such as laminaran and agar; and other carriers.

Suppositories can be formed by using polyethylene glycol, cocoa butter, a higher alcohol, a higher alcohol ester, gelatin, semi-synthesized glyceride, and other carriers.

Capsules can be typically prepared by mixing the compound of the present invention with the various carriers described above, and encapsulating the mixture in a hard gelatin capsule, a soft gelatin capsule or other capsules using known techniques.

When the compound of the present invention is prepared as an injection, such as a solution, an emulsion or a suspension, the injection is preferably sterilized and is isotonic with blood. Injections can be formed by using a diluent, such as water, ethyl alcohol, macrogol, propylene glycol, ethoxylated isostearyl alcohol, polyoxy isostearyl alcohol and a polyoxyethylene sorbitan fatty acid ester.

The injection may contain salt, glucose or glycerol in sufficient amounts to form isotonic solutions, as well as a known solubilizing agent, a buffer or a soothing agent.

When necessary, the pharmaceutical preparation may contain a coloring agent, a preservative, a fragrant material, a flavor, a sweetener, or other suitable pharmaceutical products.

Pastes, creams and gels may be formed by using a diluent, such as white Vaseline, paraffin, glycerol, a cellulose derivative, polyethylene glycol, silicone and bentonite.

The above-described pharmaceutical preparation may be administered through any route determined by the form of preparation, age, sex and other conditions of patients, as well as the severity of the disease. For example, tablets, pills, solutions, suspensions, emulsions, granules and capsules are orally administered. Injections are intravenously administered either by themselves or as a mixture with a known fluid replacement such as glucose and amino acids. When necessary, injections are administered by themselves either intramuscularly, intracutaneously, subcutaneously or intraperitoneally. Suppositories are administered rectally. Ointments and cataplasms are administered transdermally. Inhalants are administered transmucosally through nasal cavity or lung.

Having the ability to promote axonal outgrowth and promote angiogenesis, and intended to reduce or treat diseases including central nerve injuries such as head injury and spinal cord injury, cerebral infarction, cerebral infarction, ischemic heart diseases such as myocardial infarction and organic angina, peripheral arterial occlusive diseases such as critical limb ischemia, and after-effects of these diseases, the compounds of the present invention are administered at a varying dose determined by the symptoms, severity of disease or age of patients to be treated and by whether the patient has complications. The dose may also vary depending on the route of administration, dosage form and dose frequency. For oral administration, the dose is typically from 0.1 to 1000 mg/day/patient, and preferably from 1 to 500 mg/day/patient as measured in the amount of the active ingredient. For parenteral administration, the dose may be from one-hundredth to one-half the dose for oral administration. However, the preferred dose may be varied as desired, depending on the age, symptoms and other conditions of patients.

EXAMPLES

The present invention will now be described with reference to Examples, which are not intended to limit the scope of the invention.

The numbers assigned to compounds in the following Examples correspond to the numbers of the compounds given in the tables described later.

Example 1

Production of 4,6-dimethyl-5-nitropyrimidine-2-ol (Compound 1)

4,6-Dimethylpyrimidine-2-ol hydrochloride (20.0 g) was added to concentrated sulfuric acid (94.2 g) while cooled with ice. To this mixture, fuming nitric acid (15.7 g: d=1.52) was added while being stirred and cooled with ice at 5° C. or below. The resulting mixture was allowed to be slowly warmed to room temperature (20 to 30° C.), and subsequently kept stirred at room temperature (20 to 30° C.) over night. The reaction mixture was poured into ice (340 g) and neutralized with a 10N aqueous sodium hydroxide solution to a pH of approx. 2.5 (at 20° C. or below). The mixture was then extracted twice with isopropanol (225 mL) and the organic layer was concentrated under reduced pressure to obtain 33.1 g of a residue. To the resulting residue, 660 mL of chloroform and 66 mL of methanol were added and the mixture was refluxed for 30 min, followed by stirring at 50° C. for 30 min. Subsequently, the insoluble material was removed off by filtration. The filtrate was concentrated under reduced pressure to 210 g, followed by addition of 100 mL of chloroform, and concentration to 133 g. The resulting residue was stirred at room temperature (20 to 30° C.) for 30 min and subsequently cooled with ice for 2 hours. The separated crystals were collected by filtration, washed with cold chloroform, and dried to give 13.1 g of the desired product.

When necessary, some of the product was purified by silica gel column chromatography (methylene chloride:methanol=50:1) and recrystallized from methylene chloride to give a purified product.

Example 2

Production of 2-chloro-4,6-dimethyl-5-nitropyrimidine (Compound 2)

A mixture of Compound 1 (500 mg) and phosphorus oxychloride (3.89 g) was stirred for 3 hours under reflux. After the reaction was completed, the mixture was concentrated under reduced pressure. To the resulting residue, chloroform and water were added and the mixture was cooled and neutralized with a 2N aqueous sodium hydroxide solution to a pH of 5 to 7. The mixture was then extracted with chloroform and the organic layer was concentrated under reduced pressure to obtain 411 mg of the desired product. When necessary, some of the product was purified by silica gel column chromatography (ethyl acetate:hexane=1:1) to give a purified product.

Example 3

Production of 5-amino-4,6-dimethylpyrimidine-2-ol (Compound 3)

Compound 1 (1.0 g), 5% Pd—C (131 mg) were suspended in methanol (60 mL). Evacuation and replacement with hydrogen were repeated three times. Subsequently, the suspension was vigorously stirred at room temperature (20 to 30° C.) for 8 hours under hydrogen atmosphere. After the reaction was completed, the mixture was filtered through Celite and the filtered product was washed with methanol. The filtrate was evaporated under reduced pressure to give 853 mg of a crude desired product of Compound 3 as a yellow solid.

Example 4

Production of 4,6-diisopropylpyrimidine-2-ol (Compound 4)

Tert-butyl 4,6-diisopropylpyrimidine-2-yl carbonate (42 mg) was dissolved in methylene chloride (4 mL). While the solution was cooled with ice, trifluoroacetic acid (1 mL) was added to the solution. The mixture was then stirred at room temperature (20 to 30° C.) for 1 hour. After the reaction was completed, the mixture was concentrated under reduced pressure and the residue was purified by silica gel column chromatography (methylene chloride:methanol=10:1) to give 8.5 mg (30% yield) of the desired product as a brown amorphous.

Example 5

Production of 4,6-diisopropyl-5-nitropyrimidine-2-ol (Compound 5)

Compound 4 (20 mg) was suspended in a mixture of concentrated sulfuric acid (1 mL) and chloroform (1 mL). To the resulting mixture, fuming nitric acid (166 µL: d=1.50) was added while being stirred and cooled with ice at 5° C. or below. The resulting mixture was allowed to slowly warm to room temperature (20-30° C.), and subsequently kept stirred at room temperature (20-30° C.) overnight. The reaction mixture was poured into ice and neutralized with a 10N aqueous sodium hydroxide solution to a pH of approx. 5 (at 20° C. or below). The mixture was extracted twice with chloroform and the organic layer was concentrated under reduced pressure. The resulting residue was purified by silica gel column chromatography (methylene chloride:methanol=50:1 to 10:1) to give 17.8 mg (49% yield) of the desired product as a brown amorphous.

Example 6

Production of ethyl 2-(4,6-dimethyl-5-nitropyrimidine-2-yloxy)acetate (Compound 6)

Compound 1 (111.86 g) and potassium carbonate (274.21 g: 3 eq.) were suspended in acetone (2 L) and ethyl bromoacetate (165.67 g: 1.5 eq.) was added at room temperature (20 to 30° C.). The equipment used to add ethyl bromoacetate was thoroughly washed with acetone (237 mL) and stirred at 50° C. for 8 hours. Subsequently, the mixture was cooled to 35° C. and was concentrated under reduced pressure. To the resulting residue, toluene (1120 mL) was added and the mixture was stirred at room temperature overnight. The mixture was then suction-filtered and the filtered product was washed with toluene (560 mL). The filtered product was crushed and washed again with toluene (450 mL). The filtrate was evaporated under reduced pressure and the resulting crude product was purified by silica gel column chromatography (hexane:ethyl acetate=1:0 to 4:1) to give 75.98 g (45% yield) of the desired product as a yellow solid.

Example 7

Production of ethyl 2-(5-amino-4,6-dimethylpyrimidine-2-yloxy)acetate (Compound 7)

Compound 6 (75.98 g) and 5% Pd—C (7.598 g, N. E. CHEMCAT, STD Type) were suspended in ethanol (760 mL). Evacuation and replacement with hydrogen were repeated three times. Subsequently, the suspension was vigorously stirred at room temperature (20 to 30° C.) for 4.5 hours under hydrogen atmosphere. After the reaction was completed, the mixture was subjected to high precision pressure filtration (0.2 μm, PTFE) and the filtered product was washed with ethanol (474 mL). The filtrate was evaporated under reduced pressure to give 66.99 g (99.9% yield) of the desired product as a pale yellow solid.

Example 8

Production of ethyl 2-(5-tert-butoxycarbonylamino)-4,6-dimethylpyrimidine-2-yloxy)acetate (Compound 8)

Compound 7 (calculated to be 75.98 g as Compound 6 obtained in the previous process) and di-tert-butyl-dicarbonate (77.97 g) were suspended in ethyl acetate (250 mL). The mixture was stirred at 70° C. overnight. To this reaction mixture, hexane (576 mL) was added portionwise, followed by addition of a small amount of Compound 8 for seeding, and hexane (288 mL) portionwise. The mixture was then allowed to cool and stirred overnight. Subsequently, the mixture was stirred and cooled with ice for 2 hours and was then suction-filtered. The resulting solid was washed with hexane (288 mL) and dried to give 92.41 g (95% yield in 2 steps) of the desired product as a white solid.

Example 9

Production of 2-(5-(tert-butoxycarbonylamino)-4,6-dimethylpyrimidine-2-yloxy)acetic acid (Compound 9)

Compound 8 (92.4 g) was suspended in ethanol (127 mL) and a 2N aqueous sodium hydroxide solution (284 ml) was added to the suspension at room temperature (20 to 30° C.). The mixture was stirred for 2 hours at room temperature (20 to 30° C.) and a 2N aqueous HCl solution (148 mL) was added to the reaction mixture portionwise while the mixture was cooled. A small amount of Compound 9 was added for seeding, followed by a 2N aqueous HCl solution (119 mL) portionwise (internal temperature=10° C. or below). The mixture was stirred at room temperature (20 to 30° C.) overnight. Subsequently, the mixture was stirred and cooled with ice for 3 hours and was then suction-filtered. The resulting solid was washed with cold water (193 ml) and dried to give 74.8 g (89% yield) of the desired product as a white solid.

Example 10

Production of ethyl 2-(4,6-dimethyl-5-nitropyrimidine-2-ylamino)acetate (Compound 10)

A solution of Compound 2 (69 mg), glycine ethyl ester hydrochloride (102 mg) and triethylamine (103 μL) in ethanol was stirred for 3 hours under reflux. After the reaction was completed, the mixture was concentrated under reduced pressure. The resulting residue was purified by silica gel column chromatography (ethyl acetate:hexane=1:3) to give 82 mg (86% yield) of the desired product as a pale yellow amorphous.

Example 11

Production of 2-(4,6-dimethyl-5-nitropyrimidine-2-ylamino)acetic acid (Compound 11)

Compound 10 (80 mg) was suspended in 1,4-dioxane (1.5 mL) and a 2N aqueous sodium hydroxide solution (1.5 mL) was added at room temperature (20 to 30° C.). The mixture was stirred at room temperature (20 to 30° C.) for 8 hours. Subsequently, the mixture was washed with diethyl ether. While the reaction mixture was cooled, a 2N aqueous HCl solution was added portionwise to neutralize the mixture to a pH of 3. The mixture was extracted twice with chloroform and the organic layer was concentrated under reduced pressure to give 52 mg (75% yield) of the desired product as a pale yellow amorphous.

Example 12

Production of 2-(5-(tert-butoxycarbonylamino)-4,6-dimethylpyrimidine-2-yloxy)propanoic acid (Compound 12)

A mixture of Compound 3 (653 mg) and di-tert-butyl-dicarbonate (1.02 g) in N,N-dimethylformamide (25 mL) was stirred at 50° C. overnight. Subsequently, the reaction mixture was allowed to cool to room temperature (20 to 30° C.). Potassium carbonate (972 mg) and ethyl 2-bromopropionate (609 μL) were sequentially added and the mixture was stirred at room temperature (20 to 30° C.) overnight. Subsequently, water was added to the reaction mixture and the mixture was extracted twice with ethyl ether. The organic layer was concentrated under reduced pressure. To the resulting residue, 1,4-dioxane (15 mL) was added and a 2N aqueous sodium solution (15 mL) was added at room temperature (20 to 30° C.). The mixture was stirred at room temperature (20 to 30° C.) for 2 hours. Subsequently, the reaction mixture was washed with diethyl ether. While the reaction mixture was cooled, a 2N aqueous HCl solution was added portionwise to neutralize the mixture to a pH of 3. The mixture was then extracted twice with chloroform and the organic layer was concentrated under reduced pressure to give 708 mg (48% yield, in 3 steps from Example 3) of the desired product as a pale yellow amorphous.

Example 13

Production of ethyl 2-(5-amino-4,6-diisopropylpyrimidine-2-yloxy)acetate (Compound 13)

Compound 5 (6.7 mg) and 5% Pd—C (1 mg, N. E. CHEMCAT, STD Type) were suspended in methanol (1 mL). Evacuation and replacement with hydrogen were repeated three times. Subsequently, the suspension was vigorously stirred at room temperature (20 to 30° C.) for 1 hour under hydrogen atmosphere. After the reaction was completed, the mixture was filtered through Celite and the filtered product was washed with methanol. The filtrate was concentrated under reduced pressure. To the resulting residue, potassium carbonate (6.2 mg) and dimethylformamide (1 mL) were added. Ethyl bromoacetate (3.3 µL) was added to the mixture at room temperature (20 to 30° C.). The mixture was then stirred at room temperature (20 to 30° C.) overnight. Subsequently, the reaction mixture was concentrated under reduced pressure and the resulting residue was purified by silica gel column chromatography (ethyl acetate:hexane=1:1) to give 0.7 mg (8% yield) of the desired product as a pale yellow amorphous.

Example 14

Production of ethyl 2-(2-chloro-5-methylpyrimidine-4-ylamino)acetate (Compound 14)

Glycine ethyl ester hydrochloride (157 mg) was added to a solution of 2,4-dichloro-5-methylpyrimidine (184 mg) and diisopropylethylamine (486 µL) in acetonitrile (3 mL) while the solution was cooled with ice. The mixture was stirred at 40° C. overnight. Subsequently, the reaction mixture was concentrated under reduced pressure and the resulting residue was purified by silica gel column chromatography (ethyl acetate:hexane=1:3 to 1:1) to give 205 mg (81% yield) of the desired product as a white amorphous.

Example 15

Production of ethyl 2-(2-chloro-5-methylpyrimidine-4-yloxy)-2-methylpropionate (Compound 15)

Sodium hydride (52 mg: 60%) was suspended in tetrahydrofuran (3 mL). While the suspension was cooled with ice, ethyl alpha-hydroxyisobutylate (145 µL) was added. The mixture was stirred at room temperature (20 to 30° C.) for 30 min. While this mixture was cooled with ice, 2,4-dichloro-5-methylpyrimidine (176 mg) was added portionwise and the mixture was stirred at room temperature (20 to 30° C.) for 4 days. Subsequently, the reaction mixture was concentrated under reduced pressure and the resulting residue was purified by silica gel column chromatography (ethyl acetate:hexane=1:49 to 1:4.5) to give 78 mg (30% yield) of the desired product as an oily material.

Example 16

Production of 2-(2-chloro-5-methylpyrimidine-4-yloxy)-2-methylpropanoic acid (Compound 16)

The title compound was synthesized from Compound 15 in the same manner as in Example 11.

Example 17

Production of ethyl 2-(2-amino-4,6-dimethylpyrimidine-5-yloxy)acetate (Compound 17)

The title compound was synthesized from 2-amino-4,6-dimethylpyrimidine-5-ol in the same manner as in Example 6.

Example 18

Production of ethyl 2-(4-amino-5-fluoro-2-oxopyrimidine-1(2H)-yl)acetate (Compound 18)

5-Fluorocytosine (500 mg) and potassium carbonate (803 mg) were suspended in N,N-dimethylfoiliamide (5 mL) and ethyl bromoacetate (430 µl) was added to the suspension. The mixture was stirred at 100° C. overnight. The resulting precipitate was removed by filtration and the filtrate was concentrated under reduced pressure. The resulting residue was purified by silica gel column chromatography (methylene chloride:methanol=99:1 to 92:9) to give 329 mg (39% yield) of the desired product as a white amorphous.

Example 19

Production of ethyl 2-(3-methyl-5-nitropyridine-2-yloxy)acetate (Compound 19)

Sodium hydride (116 mg: 60%) was suspended in tetrahydrofuran (4 mL). While the suspension was cooled on ice, ethyl glycolate (273 µL) was added. The mixture was stirred at room temperature (20 to 30° C.) for 30 min. Subsequently, 2-chloro-3-methyl-5-nitropyridine (200 mg) was added to the mixture portionwise at room temperature (20 to 30° C.) and the mixture was stirred at room temperature (20 to 30° C.) for 3 hours. Water was then added to the reaction mixture and the mixture was extracted twice with chloroform. The organic layer was concentrated under reduced pressure to afford 310 mg of the crude desired product of Compound 19 as a brown amorphous.

Example 20

Production of ethyl 2-(5-(tert-butoxycarbonylamino)-3-methylpyridine-2-yloxy)acetate (Compound 20)

Compound 19 (319 mg) and 5% Pd—C (5 mg, N. E. CHENCAT, STD Type) were suspended in methanol. Evacuation and replacement with hydrogen were repeated three times. Subsequently, the suspension was vigorously stirred at room temperature (20 to 30° C.) for 1 hour under hydrogen atmosphere. After the reaction was completed, the mixture was filtered through Celite and the filtered product was washed with methanol. The filtrate was concentrated under reduced pressure. To the resulting residue, dimethylformamide was added and di-tert-butyl-dicarbonate (253 mg) was added to the mixture at room temperature. The mixture was then stirred at 50° C. overnight. Subsequently, water was added to the reaction mixture and the mixture was extracted twice with ethyl acetate. The organic layer was concentrated under reduced pressure to give 368 mg of the crude desired product of Compound 20 as a yellow oily material.

Example 21

Production of 2-(5-(tert-butoxycarbonylamino)-3-methylpyridine-2-yloxy)acetic acid (Compound 21)

The title compound was synthesized from Compound 20 in the same manner as in Example 11 (70% yield, in 3 steps from Example 19).

Example 22

Production of ethyl 2-(3-chloropyrazine-2-ylamino)acetate (Compound 22)

To an ethanol solution (10 mL) of 2,3-dichloropyrazine (1.0 g), glycine ethyl ester hydrochloride (940 mg) and triethylamine (1.9 mL) were added and the mixture was irradiated with microwave (150° C., 10 min). The reaction mixture was concentrated under reduced pressure. To the resulting residue, a saturated aqueous sodium bicarbonate solution was added and the product was extracted with chloroform. The organic layer was dried over sodium sulfate and concentrated under reduced pressure. The resulting residue was purified by amino-coated silica gel (Fuji Sylysia Chemical Ltd.; NH-©M1020) column chromatography (hexane:ethyl acetate=10:1) to give 212 mg (15% yield) of the desired product.

Example 23

Production of 2-(3-chloropyrazine-2-ylamino)acetic acid (Compound 23)

A 2N aqueous sodium hydroxide solution (0.6 mL) was added to an ethanol solution (0.3 mL) of Compound 22 (194 mg) and the mixture was stirred at room temperature for 1 hour. 2N hydrochloric acid was then added to the reaction mixture while cooled with ice, and the mixture was neutralized. The product was extracted with chloroform (5 times). The organic layer was dried over sodium sulfate, filtered, and concentrated under reduced pressure to give 38 mg (23% yield) of the desired product.

Example 24

Production of ethyl 2-(3-chloropyrazine-2-yloxy)acetate (Compound 24)

The title compound was synthesized from 2,3-dichloropyrazine and ethyl 2-hydroxyacetate in the same manner as in Example 19.

Example 25

Production of ethyl 2-(6-chloropyrazine-2-yloxy)acetate (Compound 25)

The title compound was synthesized from 2,6-dichloropyrazine and glycine ethyl ester hydrochloride in the same manner as in Example 19.

Example 26

Production of 2-(3-chloropyrazine-2-yloxy)acetic acid (Compound 26)

The title compound was synthesized from Compound 24 in the same manner as in Example 23.

Example 27

Production of 2-(6-chloropyrazine-2-yloxy)acetic acid (Compound 27)

The title compound was synthesized from Compound 25 in the same manner as in Example 23.

Example 28

Production of ethyl 2-(5,6-dichloropyridazine-4-ylamino)acetate (Compound 28)

A solution of 3,4,5-trichloropyridazine (300 mg), glycine ethyl ester hydrochloride (228 mg) and diisopropylethyl amine (844 µl) in ethanol was stirred for 3 hours under reflux. After the reaction was completed, the mixture was concentrated under reduced pressure and the residue was purified by silica gel column chromatography (ethyl acetate:hexane=1:9 to 1:1) to give 126 mg (31% yield) of the title compound as a pale pink amorphous.

Example 29

Production of ethyl 2-(3,5-dichloropyridazine-4-ylamino)acetate (Compound 29)

78 mg (19% yield) of the title compound was also obtained in the production of Example 28 as a pale pink amorphous.

Example 30

Production of tert-butyl 2-(2-((1-benzylpiperidine-4-yl)(methyl)amino)-2-oxoethoxy)-4,6-dimethylpyrimidine-5-ylcarbamate (Compound 30)

Compound 9 (74.74 g), 1-benzyl-N-methylpiperidine-4-amine (66.78 g: 1.3 eq.) and triethylamine (127.20 g: 5 eq.) were suspended in acetonitrile (800 mL). While the suspension was cooled on ice, a 50% propanephosphonic acid anhydride ethyl acetate solution (191.99 g) was added portionwise. The equipment used to add 50% propanephosphonic acid anhydride ethyl acetate solution was thoroughly washed with acetonitrile (192 mL) and stirred at room temperature (20 to 30° C.) overnight. Subsequently, the mixture was concentrated under reduced pressure. To the resulting residue, chloroform (250 mL) and a saturated aqueous sodium bicarbonate solution (140 mL) were sequentially added and the mixture was transferred to a separation funnel. The reaction container was thoroughly washed with chloroform (175 mL) and separation was performed. Once the organic layer was separated, chloroform (175 mL) was added to the aqueous layer and separation was performed again. The collected organic layer was dried over magnesium sulfate and was suction-filtered. The filtrate was evaporated under reduced pressure to give 183.27 g of the crude desired product of Compound 30 as a yellow amorphous.

Example 31

Production of tert-butyl 4,6-dimethyl-2-(2-(methyl (piperidine-4-yl)amino)-2-oxoethoxy)pyrimidine-5-ylcarbamate (Compound 31)

Pd—C (371 mg) was added to a solution of Compound 30 (3.7 g) in methanol (111 ml) and then, hydrogenation was carried out by stirring the mixture at atmospheric pressure and room temperature overnight. Subsequently, the catalyst was removed by filtration and the filtrate was concentrated under reduced pressure to give 2.9 g (96% yield) of the title compound.

Example 32

Production of tert-butyl 2-(2-((1-(cyclohexylmethyl) piperidine-4-yl)(methyl)amino)-2-oxoethoxy)-4,6-dimethylpyrimidine-5-ylcarbamate (Compound 32)

Bromomethyl cyclohexane (25 μL) and diisopropylethylamine (63 μL) were added to a solution of Compound 31 (71 mg) in dimethylformamide (1 mL) and the mixture was stirred at 120° C. for 8 hours. Subsequently, a saturated aqueous sodium bicarbonate solution was added to the reaction mixture and the product was extracted with ethyl acetate. The organic layer was washed with brine, dried over sodium sulfate, filtered, and concentrated under reduced pressure. The resulting residue was purified by amino-coated silica gel (Fuji Sylysia Chemical Ltd.; NH-DM1020) column chromatography (hexane:ethyl acetate=1:1) to give 40 mg (46% yield) of the desired product.

Example 33

Production of tert-butyl 2-(2-((1-(4-chlorobenzyl)-piperidine-4-yl)(methyl)amino)-2-oxoethoxy)-4,6-dimethylpyrimidine-5-ylcarbamate (Compound 33)

The title compound was synthesized from Compound 31 and 4-chlorobenzyl bromide in the same manner as in Example 32.

Example 34

Production of tert-butyl 2-(2-((1-isobutylpiperidine-4-yl)(methyl)amino)-2-oxoethoxy)-4,6-dimethylpyrimidine-5-ylcarbamate (Compound 34)

The title compound was synthesized from Compound 31 and isobutyl bromide in the same manner as in Example 32.

Example 35

Production of tert-butyl 2-(2-((1-benzoylpiperidine-4-yl)(methyl)amino)-2-oxoethoxy)-4,6-dimethylpyrimidine-5-ylcarbamate (Compound 35)

The title compound was synthesized from Compound 31 and benzoyl chloride in the same manner as in Example 32.

Example 36

Production of tert-butyl 4,6-dimethyl-2-(2-(methyl (1-phenetylpiperidine-4-yl)amino)-2-oxoethoxy) pyrimidine-5-ylcarbamate (Compound 36)

The title compound was synthesized from Compound 31 and phenetyl bromide in the same manner as in Example 32.

Example 37

Production of tert-butyl 2-(2-((1-(cyclohexanecarbonyl)piperidine-4-yl)(methyl)amino)-2-oxoethoxy)-4, 6-dimethylpyrimidine-5-ylcarbamate (Compound 37)

The title compound was synthesized from Compound 31 and cyclohexanecarbonyl chloride in the same manner as in Example 32.

Example 38

Production of tert-butyl 2-(2-((1-acetylpiperidine-4-yl)(methyl)amino)-2-oxoethoxy)-4,6-dimethylpyrimidine-5-ylcarbamate (Compound 38)

The title compound was synthesized from Compound 31 and acetyl chloride in the same manner as in Example 32.

Example 39

Production of tert-butyl 4,6-dimethyl-2-(2-(methyl (1-(phenylsulfonyl)piperidine-4-yl)amino)-2-oxoethoxy)pyrimidine-5-ylcarbamate (Compound 39)

The title compound was synthesized from Compound 31 and benzenesulfonyl chloride in the same manner as in Example 32.

Example 40

Production of tert-butyl 2-(2-((1-cyclohexylpiperidine-4-yl)(methyl)amino)-2-oxoethoxy)-4,6-dimethylpyrimidine-5-ylcarbamate (Compound 40)

The title compound was synthesized from Compound 31, cyclohexanone and sodium triacetoxy-borohydride in the same manner as in Example 32.

Example 41

Production of tert-butyl 4,6-dimethyl-2-(2-(methyl (1-(piperidine-1-carbonyl)piperidine-4-yl)amino)-2-oxoethoxy)pyrimidine-5-ylcarbamate (Compound 41)

The title compound was synthesized from Compound 31 and 1-piperidinocarbonyl chloride in the same manner as in Example 32.

Example 42

Production of tert-butyl 4,6-dimethyl-2-(2-(methyl (1-(2-methylbenzyl)piperidine-4-yl)amino)-2-oxoethoxy)pyrimidine-5-ylcarbamate (Compound 42)

The title compound was synthesized from Compound 31 and 2-methylbenzyl bromide in the same manner as in Example 32.

Example 43

Production of tert-butyl 4,6-dimethyl-2-(2-(methyl (1-phenylpiperidine-4-yl)amino)-2-oxoethoxy)pyrimidine-5-ylcarbamate (Compound 43)

The title compound was synthesized from Compound 31, phenylboric acid, copper (II) acetate and pyridine in the same manner as in Example 32.

Example 44

Production of tert-butyl 2-(2-((1-(2-methoxyethyl) piperidine-4-yl)(methyl)amino)-2-oxoethoxy)-4,6-dimethylpyrimidine-5-ylcarbamate (Compound 44)

The title compound was synthesized from Compound 31 and bromoethyl methyl ether in the same manner as in Example 32.

Example 45

Production of tert-butyl 4,6-dimethyl-2-(2-(methyl (1-(pyridine-3-ylmethyl)piperidine-4-yl)amino)-2-oxoethoxy)pyrimidine-5-ylcarbamate (Compound 45)

The title compound was synthesized from Compound 31 and 3-(bromomethyl)pyridine hydrobromide in the same manner as in Example 32.

Example 46

Production of tert-butyl 2-(2-((1-(4-fluorobenzyl) piperidine-4-yl)(methyl)amino)-2-oxoethoxy)-4,6-dimethylpyrimidine-5-ylcarbamate (Compound 46)

The title compound was synthesized from Compound 31 and 4-fluorobenzyl bromide in the same manner as in Example 32.

Example 47

Production of tert-butyl 4,6-dimethyl-2-(2-(methyl (1-((tetrahydrofuran-2-yl)methyl)piperidine-4-yl) amino)-2-oxoethoxy)pyrimidine-5-ylcarbamate (Compound 47)

The title compound was synthesized from Compound 31 and tetrahydrofurfuryl bromide in the same manner as in Example 32.

Example 48

Production of tert-butyl 4,6-dimethyl-2-(2-(methyl (1-(pyridine-3-yl)piperidine-4-yl)amino)-2-oxoethoxy)pyrimidine-5-ylcarbamate (Compound 48)

The title compound was synthesized from Compound 31, 3-(4,4,5,5-tetramethyl-1,3,2-dioxaborolane-2-yl)pyridine, copper (II) acetate and pyridine in the same manner as in Example 32.

Example 49

Production of tert-butyl 2-(2-((1-(cyclopropylmethyl)-piperidine-4-yl)(methyl)amino)-2-oxoethoxy)-4,6-dimethylpyrimidine-5-ylcarbamate (Compound 49)

Compound 9 (100 mg), 1-(cyclopropylmethyl)-N-methylpiperidine-4-amine (56.6 mg) and triethylamine (234 µL) were suspended in acetonitrile (2 mL). While the suspension was cooled with ice, a 50% propane phosphonic acid anhydride ethyl acetate solution (273 mg) was added portionwise. The equipment used to add the 50% propane phosphonic acid anhydride ethyl acetate solution was thoroughly washed with acetonitrile (0.5 mL) and was stirred at room temperature (20 to 30° C.) overnight. Subsequently, the reaction mixture was concentrated under reduced pressure and the resulting residue was purified by amino-coated silica gel (Fuji Sylysia Chemical Ltd.; NH-DM1020) column chromatography (methylene chloride:methanol=30:1) to give 79 mg (52% yield) of the desired product as a pale yellow amorphous.

Example 50

Production of tert-butyl 2-(2-((1-(3-methoxybenzyl) piperidine-4-yl)(methyl)amino)-2-oxoethoxy)-4,6-dimethylpyrimidine-5-ylcarbamate (Compound 50)

The title compound was synthesized from Compound 31 and 1-(bromomethyl)-3-methoxybenzene in the same manner as in Example 32.

Example 51

Production of tert-butyl 2-(2-((1-(4-cyanobenzyl) piperidine-4-yl)(methyl)amino)-2-oxoethoxy)-4,6-dimethylpyrimidine-5-ylcarbamate (Compound 51)

The title compound was synthesized from Compound 31 and 4-(bromomethyl)benzonitrile in the same manner as in Example 32.

Example 52

Production of tert-butyl 4,6-dimethyl-2-(2-methyl(1-(3-(trifluoromethyl)benzyl)piperidine-4-yl)amino)-2-oxoethoxy)pyrimidine-5-ylcarbamate (Compound 52)

The title compound was synthesized from Compound 31 and 1-(bromomethyl)-3-(trifluoromethyl)-benzene in the same manner as in Example 32.

Example 53

Production of tert-butyl 4,6-dimethyl-2-(2-(methyl (1-(3,4,5-trifluorobenzyl)piperidine-4-yl)amino)-2-oxoethoxy)pyrimidine-5-ylcarbamate (Compound 53)

The title compound was synthesized from Compound 31 and 5-(bromomethyl)-1,2,3-trifluorobenzene in the same manner as in Example 32.

Example 54

Production of tert-butyl 2-(2-((1-(cyclopropanecarbonyl)piperidine-4-yl)(methyl)amino)-2-oxoethoxy)-4,6-dimethylpyrimidine-5-ylcarbamate (Compound 54)

The title compound was synthesized from Compound 31 and cyclopropanecarbonyl chloride in the same manner as in Example 32.

Example 55

Production of tert-butyl 2-(2-((1-(biphenyl-4-yl)(methyl)piperidine-4-yl)(methyl)amino)-2-oxoethoxy)-4, 6-dimethylpyrimidine-5-ylcarbamate (Compound 55)

The title compound was synthesized from Compound 31 and 4-(bromomethyl)biphenyl in the same manner as in Example 32.

Example 56

Production of tert-butyl 2-(1-((1-benzylpiperidine-4-yl)(methyl)amino)-1-oxopropane-2-yloxy)-4,6-dimethylpyrimidine-5-ylcarbamate (Compound 56)

The title compound was synthesized from Compound 12 and 1-benzyl-N-methylpiperidine-4-amine in the same manner as in Example 49.

Example 57

Production of tert-butyl 4,6-dimethyl-2-(2-oxo-2-(piperidine-4-ylamino)ethoxy)pyrimidine-5-ylcarbamate (Compound 57)

Tert-butyl 2-(2-(1-benzylpiperidine-4-ylamino)-2-oxoethoxy)-4,6-dimethyl-pyrimidine-5-ylcarbamate was synthesized from Compound 9 and 4-amino-1-benzylpiperidine in the same manner as in Example 49. The title compound was then synthesized from tert-butyl 2-(2-(1-benzylpiperidine-4-ylamino)-2-oxoethoxy)-4,6-dimethyl-pyrimidine-5-ylcarbamate in the same manner as in Example 31.

Example 58

Production of tert-butyl 2-(2-(1-(cyclopropylmethyl) piperidine-4-ylamino)-2-oxoethoxy)-4,6-dimethylpyrimidine-5-ylcarbamate (Compound 58)

The title compound was synthesized from Compound 57 and bromomethyl cyclopropane in the same manner as in Example 32.

Example 59

Production of tert-butyl 2-(2-(1-(4-fluorobenzoyl)-piperidine-4-ylamino)-2-oxoethoxy)-4,6-dimethylpyrimidine-5-ylcarbamate (Compound 59)

The title compound was synthesized from Compound 57 and 4-fluorobenzoyl chloride in the same manner as in Example 32.

Example 60

Production of tert-butyl 2-(2-((1-benzylpiperidine-4-yl)(cyclopropyl)amino)-2-oxoethoxy)-4,6-dimethylpyrimidine-5-ylcarbamate (Compound 60)

The title compound was synthesized from Compound 9 and 1-benzyl-N-cyclopropylpiperidine-4-amine in the same manner as in Example 49.

Example 61

Production of tert-butyl 6-(2-((1-benzylpiperidine-4-yl)(methyl)amino)-2-oxoethoxy)-5-methylpyridine-3-ylcarbamate (Compound 61)

The title compound was synthesized from Compound 21 and 1-benzyl-N-methylpiperidine-4-amine in the same manner as in Example 49.

Example 62

Production of N-(1-benzylpiperidine-4-yl)-2-(4,6-dimethyl-5-nitropyrimidine-2-ylamino)-N-methylacetamide (Compound 62)

The title compound was synthesized from Compound 11 and 1-benzyl-N-methylpiperidine-4-amine in the same manner as in Example 49.

Example 63

Production of 2-(5-amino-4,6-dimethylpyrimidine-2-ylamino)-N-(1-benzylpiperidine-4-yl)-N-methylacetamide (Compound 63)

Compound 62 (93 mg) and zinc (147 mg) were suspended in acetic acid (2 mL) and the suspension was stirred at room temperature (20 to 30° C.) for 3 hours. Subsequently, the reaction mixture was filtered and the filtrate was concentrated under reduced pressure. The resulting residue was purified by silica gel column chromatography (ethyl acetate:hexane=5:1 to 3:1) to give 25.4 mg (29% yield) of the desired product as a pale yellow amorphous.

Example 64

Production of 4-((4-(2-(5-amino-4,6-dimethylpyrimidine-2-yloxy)-N-methylacetamide)piperidine-1-yl)methyl)benzamide (Compound 64)

Tert-butyl 2-(2-((1-(4-carbamoylbenzyl)-piperidine-4-yl)(methyl)amino)-2-oxoethoxy)-4,6-dimethylpyrimidine-5-ylcarbamate was synthesized from Compound 9 and 4-((4-(methylamino)piperidine-1-yl)methyl)benzamide in the same manner as in Example 49. Then, tert-butyl 2-(2-((1-(4-carbamoylbenzyl)piperidine-4-yl)(methyl)amino)-2-oxoethoxy)-4,6-dimethylpyrimidine-5-ylcarbamate was dissolved in methylene chloride (4 mL). While the solution was cooled with ice, trifluoroacetic acid (1 mL) was added. The mixture was stirred at room temperature (20 to 30° C.) for 4 to 5 hours. After the reaction was completed, the reaction mixture was concentrated under reduced pressure. The resulting residue was purified by amino-coated silica gel (Fuji Sylysia Chemical Ltd.; NH-DM1020) column chromatography (methylene chloride:methanol=10:1) to give 28.1 mg (36% yield: in 2 steps) of the desired product as a white solid.

Example 65

Production of 2-(5-amino-4,6-dimethylpyrimidine-2-yloxy)-N-(1-benzylpiperidine-4-yl)-N-methylacetamide (Compound 65)

Compound 30 (calculated assuming that Compound 9 in the previous process was 74.74 g and the yield of amidation was 80%) was dissolved in chloroform (140 mL). The solution was added to a 6N aqueous HCl solution (530 mL) at room temperature (20 to 30° C.). The equipment used to add compound 30 was thoroughly washed with chloroform (240 mL) and was then stirred at room temperature (20 to 30° C.) for 2.5 hours. After the chloroform layer was separated, chloroform (300 mL) was added to the aqueous layer. While ice (740.7 g in total) was added as necessary, a 4N aqueous sodium hydroxide solution (805 mL) was added portionwise. An additional amount of 4N aqueous sodium hydroxide solution (25 mL to adjust the pH of the aqueous layer to 8.5) was added, followed by the addition of chloroform (80 mL), and separation was performed. After the chloroform layer was separated, chloroform (200 ml) was added to the aqueous layer and separation was performed again. The chloroform layer collected in the two extraction processes was dried over magnesium sulfate and suction-filtered. The filtrate was then evaporated under reduced pressure to give 100.15 g (103.9% yield, in 2 steps) of the crude desired product as a pale yellow solid.

Isopropanol (1020 mL) was added to the resulting solid and the mixture was heated to 85° C. to dissolve the solid. The mixture was stirred as it was allowed to cool. Once the temperature of heat bath reached 67° C., seeding was carried out and the mixture was kept stirred overnight. Subsequently, the mixture was stirred for 2 hours while it was cooled with ice, and was then suction-filtered. The resulting solid was washed with cold isopropanol (150 mL) and dried to give 89.60 g (92.9% yield, in 2 steps) of the desired compound (recrystallized from isopropanol) as colorless crystals.

To the product (50.00 g) recrystallized from isopropanol, ethanol (220 mL) was added and the mixture was heated to 85° C. to dissolve the product. The mixture was stirred as it was allowed to cool. Once the temperature of heat bath reached 65° C., seeding was carried out and the mixture was kept stirred overnight. Subsequently, the mixture was stirred for 2 hours while it was cooled with ice, and was then suction-filtered. The resulting solid was washed with cold isopropanol (100 mL) and dried to give 48.18 (96% yield) of the desired product as white crystals.

Example 66

Production of 2-(5-amino-4,6-dimethylpyrimidine-2-yloxy)-N-(1-(cyclopropylmethyl)piperidine-4-yl)-N-methylacetamide.2-hydrochloride (Compound 66)

To a chloroform (1 mL) solution of Compound 49 (78 mg), 6N HCl (1 mL) was added and the mixture was stirred at room temperature for 1 hour. While the reaction mixture was cooled with ice, a 4N aqueous sodium hydroxide solution was added to neutralize the mixture. The resulting product was extracted with chloroform and the organic layer was dried over sodium sulfate, filtered, and concentrated under reduced pressure. The resulting residue was purified by amino-coated silica gel (Fuji Sylysia Chemical Ltd.; NH-DM1020) column chromatography (ethyl acetate) to give 37.5 mg (62% yield) of 2-(5-amino-4,6-dimethylpyrimidine-2-yloxy)-N-(1-(cyclopropylmethyl)piperidine-4-yl)-N-methylacetamide. Then, to a methanol solution of 2-(5-amino-4,6-dimethylpyrimidine-2-yloxy)-N-(1-(cyclopropylmethyl)piperidine-4-yl)-N-methylacetamide, 2 equivalents of 4N HCl/1,4-dioxane solution was added and the mixture was concentrated under reduced pressure. The desired product was afforded by recrystallization from methanol/ethyl acetate as white crystals.

Example 67

Production of 2-(5-amino-4,6-dimethylpyrimidine-2-yloxy)-N-(1-(cyclopentyl)piperidine-4-yl)-N-methylacetamide (Compound 67)

The title compound was synthesized from Compound 9 and 1-cyclopentyl-N-methylpiperidine-4-amine in the same manner as in Example 64.

Example 68

Production of 2-(5-amino-4,6-dimethylpyrimidine-2-yloxy)-N-(1-(2-cyclohexylethyl)piperidine-4-yl)-N-methylacetamide.2-hydrochloride (Compound 68)

2-(5-Amino-4,6-dimethylpyrimidine-2-yloxy)-N-(1-(2-cyclohexylethyl)piperidine-4-yl)-N-methylacetamide was synthesized from Compound 9 and N-methyl-1-(2-cyclohexylethyl)piperidine-4-amine in the same manner as in Example 64. Then, to a methanol solution of 2-(5-amino-4,6-dimethylpyrimidine-2-yloxy)-N-(1-(2-cyclohexylethyl)-piperidine-4-yl)-N-methylacetamide, 2 equivalents of 4N HCl/1,4-dioxane solution was added and the mixture was concentrated under reduced pressure. The desired product was afforded by recrystallization from methanol/diethyl ether as white crystals.

Example 69

Production of 2-(5-amino-4,6-dimethylpyrimidine-2-yloxy)-N-methyl-N-(1-(4-(trifluoromethyl)benzyl)piperidine-4-yl)acetamide (Compound 69)

The title compound was synthesized from Compound 9 and N-methyl-1-(4-(trifluoromethyl)benzyl)-piperidine-4-amine in the same manner as in Example 64 and recrystallized from methylene chloride.

Example 70

Production of 2-(5-amino-4,6-dimethylpyrimidine-2-yloxy)-N-(1-(cyclobutanecarbonyl)piperidine-4-yl)-N-methylacetamide (Compound 70)

The title compound was synthesized from Compound 9 and cyclobutyl (4-(methylamino)piperidine-1-yl)methanone in the same manner as in Example 64.

Example 71

Production of 2-(5-amino-4,6-dimethylpyrimidine-2-yloxy)-N-(1-(cyclohexylmethyl)piperidine-4-yl)-N-methylacetamide (Compound 71)

6N HCl (0.7 mL) was added to a chloroform (0.5 mL) solution of Compound 32 (39 mg) and the mixture was stirred at room temperature for 1 hour. While the reaction mixture was cooled with ice, a 4N aqueous sodium hydroxide solution was added to neutralize the mixture. The resulting product was extracted with chloroform and the organic layer was dried over sodium sulfate, filtered, and concentrated under reduced pressure. The resulting residue was purified by amino-coated silica gel (Fuji Sylysia Chemical Ltd., NH-DM1020) column chromatography (ethyl acetate) to give 23 mg (76% yield) of the title compound.

Example 72

Production of 2-(5-amino-4,6-dimethylpyrimidine-2-yloxy)-N-(1-(4-chlorobenzyl)piperidine-4-yl)-N-methylacetamide (Compound 72)

The title compound was synthesized from Compound 33 in the same manner as in Example 71.

Example 73

Production of 2-(5-amino-4,6-dimethylpyrimidine-2-yloxy)-N-(1-isobutylpiperidine-4-yl)-N-methylacetamide (Compound 73)

The title compound was synthesized from Compound 34 in the same manner as in Example 71.

Example 74

Production of 2-(5-amino-4,6-dimethylpyrimidine-2-yloxy)-N-(1-benzoylpiperidine-4-yl)-N-methylacetamide (Compound 74)

The title compound was synthesized from Compound 35 in the same manner as in Example 71.

Example 75

Production of 2-(5-amino-4,6-dimethylpyrimidine-2-yloxy)-N-methyl-N-(1-phenetylpiperidine-4-yl)acetamide (Compound 75)

The title compound was synthesized from Compound 36 in the same manner as in Example 71.

Example 76

Production of 2-(5-amino-4,6-dimethylpyrimidine-2-yloxy)-N-(1-(cyclohexanecarbonyl)piperidine-4-yl)-N-methylacetamide hydrochloride (Compound 76)

2-(5-Amino-4,6-dimethylpyrimidine-2-yloxy)-N-(1-cyclohexanecarbonyl)piperidine-4-yl)-N-methylacetamide was synthesized from compound 37 in the same manner as in Example 71. Then, to a methanol solution of 2-(5-amino-4,6-dimethylpyrimidine-2-yloxy)-N-(1-cyclohexanecarbonyl) piperidine-4-yl)-N-methylacetamide, 1 equivalent of 4N HCl/1,4-dioxane solution was added and the mixture was concentrated under reduced pressure. The desired product was afforded by recrystallization from methanol/diethyl ether as a pale yellow solid.

Example 77

Production of N-(1-acetylpiperidine-4-yl)-2-(5-amino-4,6-dimethylpyrimidine-2-yloxy)-N-methylacetamide hydrochloride (Compound 77)

The title compound was synthesized from Compound 38 in the same manner as in Example 76.

Example 78

Production of 2-(5-amino-4,6-dimethylpyrimidine-2-yloxy)-N-methyl-N-(1-(phenylsulfonyl)piperidine-4-yl)acetamide (Compound 78)

The title compound was synthesized from Compound 39 in the same manner as in Example 71.

Example 79

Production of 2-(5-amino-4,6-dimethylpyrimidine-2-yloxy)-N-(1-cyclohexylpiperidine-4-yl)-N-methylacetamide (Compound 79)

The title compound was synthesized from Compound 40 in the same manner as in Example 71.

Example 80

Production of 2-(5-amino-4,6-dimethylpyrimidine-2-yloxy)-N-methyl-N-(1-(piperidine-1-carbonyl)piperidine-4-yl)acetamide (Compound 80)

The title compound was synthesized from Compound 41 in the same manner as in Example 71.

Example 81

Production of 2-(5-amino-4,6-dimethylpyrimidine-2-yloxy)-N-methyl-N-(1-(2-methylbenzyl)piperidine-4-yl)acetamide (Compound 81)

The title compound was synthesized from Compound 42 in the same manner as in Example 71.

Example 82

Production of 2-(5-amino-4,6-dimethylpyrimidine-2-yloxy)-N-methyl-N-(1-phenylpiperidine-4-yl)acetamide (Compound 82)

The title compound was synthesized from Compound 43 in the same manner as in Example 71.

Example 83

Production of 2-(5-amino-4,6-dimethylpyrimidine-2-yloxy)-N-(1-(2-methoxy ethyl)piperidine-4-yl)-N-methylacetamide hydrochloride (Compound 83)

The title compound was synthesized from Compound 44 in the same manner as in Example 76.

Example 84

Production of 2-(5-amino-4,6-dimethylpyrimidine-2-yloxy)-N-methyl-N-(1-(pyridine-3-ylmethyl)piperidine-4-yl)acetamide hydrochloride (Compound 84)

The title compound was synthesized from Compound 45 in the same manner as in Example 76.

Example 85

Production of 2-(5-amino-4,6-dimethylpyrimidine-2-yloxy)-N-(1-(4-fluorobenzyl)piperidine-4-yl)-N-methylacetamide (Compound 85)

The title compound was synthesized from Compound 46 in the same manner as in Example 71.

Example 86

Production of 2-(5-amino-4,6-dimethylpyrimidine-2-yloxy)-N-methyl-N-(1-((tetrahydrofuran-2-yl)methyl)piperidine-4-yl)acetamide (Compound 86)

The title compound was synthesized from Compound 47 in the same manner as in Example 71.

Example 87

Production of 2-(5-amino-4,6-dimethylpyrimidine-2-yloxy)-N-methyl-N-(1-(pyridine-3-yl)piperidine-4-yl)acetamide hydrochloride (Compound 87)

The title compound was synthesized from Compound 48 in the same manner as in Example 76.

Example 88

Production of 2-(5-amino-4,6-dimethylpyrimidine-2-yloxy)-N-(1-(3-methoxybenzyl)piperidine-4-yl)-N-methylacetamide hydrochloride (Compound 88)

The title compound was synthesized from Compound 50 in the same manner as in Example 76.

Example 89

Production of 2-(5-amino-4,6-dimethylpyrimidine-2-yloxy)-N-(1-(4-cyanobenzyl)piperidine-4-yl)-N-methylacetamide hydrochloride (Compound 89)

The title compound was synthesized from Compound 51 in the same manner as in Example 76.

Example 90

Production of 2-(5-amino-4,6-dimethylpyrimidine-2-yloxy)-N-methyl-N-(1-(3-(trifluoromethyl)benzyl)piperidine-4-yl)acetamide (Compound 90)

The title compound was synthesized from Compound 52 in the same manner as in Example 71.

Example 91

Production of 2-(5-amino-4,6-dimethylpyrimidine-2-yloxy)-N-methyl-N-(1-(3,4,5-trifluorobenzyl)piperidine-4-yl)acetamide (Compound 91)

The title compound was synthesized from Compound 53 in the same manner as in Example 71.

Example 92

Production of 2-(5-amino-4,6-dimethylpyrimidine-2-yloxy)-N-(1-(cyclopropanecarbonyl)piperidine-4-yl)-N-methylacetamide (Compound 92)

The title compound was synthesized from Compound 54 in the same manner as in Example 71.

Example 93

Production of 2-(5-amino-4,6-dimethylpyrimidine-2-yloxy)-N-(1-(biphenyl-4-yl methyl)piperidine-4-yl)-N-methylacetamide hydrochloride (Compound 93)

The title compound was synthesized from Compound 55 in the same manner as in Example 76.

Example 94

Production of 2-(5-amino-4,6-dimethylpyrimidine-2-yloxy)-N-methyl-N-(piperidine-4-yl)acetamide (Compound 94)

The title compound was synthesized from Compound 31 in the same manner as in Example 71.

Example 95

Production of N-(1-benzylpiperidine-4-yl)-2-(4,6-dimethylpyrimidine-2-yloxy)-N-methylacetamide hydrochloride (Compound 95)

N-(1-benzylpiperidine-4-yl)-2-(4,6-dimethylpyrimidine-2-yloxy)-N-methylacetamide (147 mg: 62% yield) was synthesized from 2-(4,6-dimethylpyrimidine-2-yl)oxyaceteic acid (117 mg) and 1-benzyl-N-methylpiperidine-4-amine (131 mg) in the same manner as in Example 49. Then, to a methanol solution of N-(1-benzylpiperidine-4-yl)-2-(4,6-dimethylpyrimidine-2-yloxy)-N-methylacetamide, 1 equivalent of 4N HCl/ethyl acetate solution was added. The mixture was then concentrated under reduced pressure to give the desired product as a white amorphous.

Example 96

Production of 2-(4,6-dimethylpyrimidine-2-yloxy)-N-methyl-N-(1-(4-(trifluoromethyl)benzyl)piperidine-4-yl)acetamide maleate (Compound 96)

2-(4,6-Dimethylpyrimidine-2-yloxy)-N-methyl-N-(1-(4-(trifluoromethyl)-benzyl)piperidine-4-yl)acetamide was synthesized from 2-(4,6-dimethylpyrimidine-2-yl)oxyacetic acid and N-methyl-1-(4-(trifluoromethyl)benzyl)piperidine-4-amine in the same manner as in Example 49. Then, to a methanol solution of 2-(4,6-dimethylpyrimidine-2-yloxy)-N-methyl-N-(1-(4-(trifluoromethyl)benzyl)-piperidine-4-yl)acetamide, 1 equivalent of maleic acid was added and the mixture was concentrated under reduced pressure. The desired product was afforded by recrystallization from 2-propanol/diisopropyl ether as a white solid.

Example 97

Production of 2-(5-amino-4,6-dimethyl-2-oxopyrimidine-1(2H)-yl)-N-(1-benzylpiperidine-4-yl)-N-methylacetamide (Compound 97)

Ethyl 2-(4,6-dimethyl-5-nitro-2-oxopyrimidine-1(2H)-yl) acetate (500 mg), the by-product obtained in Example 6, and 5% Pd—C (40 mg) were suspended in methanol (20 mL). Evacuation and replacement with hydrogen were repeated three times. Subsequently, the suspension was vigorously stirred at room temperature (20 to 30° C.) for 1 hour under hydrogen atmosphere. After the reaction was completed, the mixture was filtered through Celite and the filtrate was evaporated under reduced pressure. The resulting residue and di-tert-butyl dicarbonate (427 mg) were dissolved in dimethylformamide (15 mL) and the solution was stirred at 50° C. overnight. The reaction mixture was distributed between ethyl acetate and water. The aqueous layer was concentrated under reduced pressure. To the resulting residue, a 2N aqueous sodium hydroxide solution (4 mL) was added and the mixture was stirred at room temperature (20 to 30° C.) for 6 hours. Subsequently, a 2N aqueous HCl solution (4 mL) was added portionwise while the reaction mixture was cooled and the mixture was concentrated under reduced pressure. Methanol was then added and insoluble materials were removed by filtration. The filtrate was concentrated under reduced pressure. 9.5 mg (1.3% yield, in 5 steps) of the title compound was synthesized from the resulting residue and 1-benzyl-N-methylpiperidine-4-amine in the same manner as in Example 64.

Example 98

Production of 2-(5-amino-4,6-dimethylpyrimidine-2-yloxy)-N-(1-(cyclopropylmethyl)piperidine-4-yl)-N-methylpropanamide (Compound 98)

The title compound was synthesized from Compound 12 and 1-(cyclopropylmethyl)-N-methyl-piperidine-4-amine in the same manner as in Example 64.

Example 99

Production of 2-(5-amino-4,6-dimethylpyrimidine-2-yloxy)-N-(1-benzylpiperidine-4-yl)-N-methylpropanamide (Compound 99)

The title compound was synthesized from Compound 56 in the same manner as in Example 71.

Example 100

Production of N-(1-benzylpiperidine-4-yl)-2-(4,6-dimethyl-5-(methylamino)pyrimidine-2-yloxy)-N-methylpropanamide (Compound 100)

To a tetrahydrofuran (1 mL) solution of Compound 56 (72 mg), potassium bis(trimethylsilyl)amide (0.5M toluene solution: 273 µL) was added at −78° C. The mixture was stirred at −78° C. for 30 min and methyl iodide (9 µL) was added portionwise. The mixture was then stirred overnight as it was allowed to be slowly warmed to room temperature (20 to 30° C.). Subsequently, a saturated aqueous ammonium chloride solution was added to the reaction mixture and the mixture was extracted twice with chloroform. The organic layer was concentrated under reduced pressure and the resulting residue was purified by amino-coated silica gel (Fuji Sylysia Chemical Ltd.; NH-DM1020) column chromatography (ethyl acetate:hexane=1:19 to 1:1) to give 7.7 mg (10% yield) of tert-butyl 2-(1-((1-benzylpiperidine-4-yl)(methyl)amino)-1-oxopropane-2-yloxy)-4,6-dimethylpyrimidine-5-yl(methyl) carbamate. 2.6 mg (42% yield) of the title compound was synthesized from tert-butyl 2-(1-((1-benzylpiperidine-4-yl) (methyl)amino)-1-oxopropane-2-yloxy)-4,6-dimethylpyrimidine-5-yl(methyl)carbamate in the same manner as in Example 71.

Example 101

Production of 2-(5-amino-4,6-dimethylpyrimidine-2-yloxy)-N-(1-(cyclopropylmethyl)piperidine-4-yl) acetamide (Compound 101)

The title compound was synthesized from Compound 58 in the same manner as in Example 71.

Example 102

Production of 2-(5-amino-4,6-dimethylpyrimidine-2-yloxy)-N-(1-(4-fluorobenzoyl)piperidine-4-yl)acetamide (Compound 102)

The title compound was synthesized from Compound 59 in the same manner as in Example 71.

Example 103

Production of 2-(5-amino-4,6-dimethylpyrimidine-2-yloxy)-N-(1-benzylpiperidine-4-yl)-N-cyclopropylacetamide (Compound 103)

The title compound was synthesized from Compound 60 in the same manner as in Example 71.

Example 104

Production of 2-(5-amino-4,6-diisopropylpyrimidine-2-yloxy)-N-(1-benzylpiperidine-4-yl)-N-methylacetamide (Compound 104)

As in Example 11, a carboxylic acid derivative was synthesized from Compound 13. Then, the title compound was synthesized from the obtained carboxylic acid derivative and 1-benzyl-N-methylpiperidine-4-amine in the same manner as in Example 49.

Example 105

Production of 2-(5-amino-4,6-diisopropylpyrimidine-2-yloxy)-N-(1-(cyclopropylmethyl)piperidine-4-yl)-N-methylacetamide (Compound 105)

As in Example 11, a carboxylic acid derivative was synthesized from Compound 13. Then, the title compound was synthesized from the obtained carboxylic acid derivative and 1-(cyclopropylmethyl)-N-methylpiperidine-4-amine in the same manner as in Example 49.

Example 106

Production of 2-(2-chloro-5-methylpyrimidine-4-ylamino)-N-(1-(cyclopropylmethyl)piperidine-4-yl)-N-methylacetamide (Compound 106)

The title compound was synthesized from Compound 14 in the same manner as in Example 105.

Example 107

Production of N-(1-(cyclopropylmethyl)piperidine-4-yl)-2-(2-(4-methoxybenzylamino)-5-methylpyrimidine-4-ylamino)-N-methylacetamide (Compound 107)

A solution of Compound 106 (93 mg), 4-methoxybenzylamine (345 µL) and diisopropylethylamine (45.5 µL) in n-butanol (1.5 mL) was stirred overnight under reflux. Subsequently, the reaction mixture was concentrated under reduced pressure and the resulting residue was purified by silica gel column chromatography (methylene chloride:methanol=50:1 to 4:1) to give 43 mg (36% yield) of the desired product as a white amorphous.

Example 108

Production of 2-(2-amino-5-methylpyrimidine-4-ylamino)-N-(1-(cyclopropylmethyl)piperidine-4-yl)-N-methylacetamide (Compound 108)

Compound 107 (24.9 mg) was dissolved in methylene chloride (1 mL). While the solution was cooled with ice, trifluoroacetic acid (3 mL) was added. The reaction mixture was stirred at room temperature (20 to 30° C.) overnight. After the reaction was completed, the reaction mixture was concentrated under reduced pressure. The resulting residue was purified by silica gel column chromatography (methylene chloride:methanol=10:1 to 4:1) to give 12.6 mg (68% yield) of the desired product as a white amorphous.

Example 109

Production of N-(1-benzylpiperidine-4-yl)-2-(2-chloro-5-methylpyrimidine-4-ylamino)-N-methylacetamide (Compound 109)

The title compound was synthesized from Compound 14 in the same manner as in Example 104.

Example 110

Production of N-(1-benzylpiperidine-4-yl)-2-(2-(4-methoxy benzylamino)-5-methylpyrimidine-4-ylamino)-N-methylacetamide (Compound 110)

The title compound was synthesized from Compound 109 in the same manner as in Example 107.

Example 111

Production of 2-(2-amino-5-methylpyrimidine-4-ylamino)-N-(1-benzylpiperidine-4-yl)-N-methylacetamide maleate (Compound 111)

2-(2-Amino-5-methylpyrimidine-4-ylamino)-N-(1-benzylpiperidine-4-yl)-N-methylacetamide was synthesized from Compound 110 in the same manner as in Example 108. Then, to a methanol solution of 2-(2-amino-5-methylpyrimidine-4-ylamino)-N-(1-benzylpiperidine-4-yl)-N-methylacetamide, 1 equivalent of maleic acid was added and the mixture was concentrated under reduced pressure to give the title compound.

Example 112

Production of N-(1-benzylpiperidine-4-yl)-2-(2-chloro-5-methylpyrimidine-4-yloxy)-N,2-dimethyl-propanamide maleate (Compound 112)

The title compound was synthesized from Compound 16 and 1-benzyl-N-methylpiperidine-4-amine in the same manner as in Example 96.

Example 113

Production of 2-(2-amino-4,6-dimethylpyrimidine-5-yloxy)-N-(1-benzylpiperidine-4-yl)-N-methylacetamide (Compound 113)

The title compound was synthesized from Compound 17 in the same manner as in Example 104.

Example 114

Production of 2-(4-amino-5-fluoro-2-oxopyrimidine-1(2H)-yl)-N-(1-benzylpiperidine-4-yl)-N-methylacetamide (Compound 114)

The title compound was synthesized from Compound 18 in the same manner as in Example 104.

Example 115

Production of 2-(5-amino-4,6-dimethylpyrimidine-2-yloxy)-N-(1-benzylpiperidine-4-yl)-N-methylacetamide.hydrobromide (Compound 115)

Compound 65 (198 mg) was suspended in methanol (1 mL) and hydrobromic acid (89 mg: 47% aqueous solution) was added to the suspension at room temperature (20 to 30° C.). After the compound was dissolved, the mixture was concentrated under reduced pressure. Ethanol (3 mL) was added to the resulting residue and the mixture was stirred under reflux. Water (0.6 mL) was then added portionwise. Once the residue was dissolved, the mixture was stirred overnight as it was allowed to cool. Subsequently, the mixture was stirred and cooled with ice for 1 hour and was suction-filtered. The resulting solid was washed with ethanol and dried to give 189 mg (78% yield) of the desired product as white crystals.

Example 116

Production of 2-(5-amino-4,6-dimethylpyrimidine-2-yloxy)-N-(1-benzylpiperidine-4-yl)-N-methylacetamide hydrochloride (Compound 116)

Compound 65 (200 mg) was suspended in methanol (1 mL) and 4N HCl/1,4-dioxane solution (130 µL) was added to the suspension at room temperature (20 to 30° C.). After the compound was dissolved, the mixture was concentrated under reduced pressure. Then, isopropanol (2.0 mL) was added to the resulting residue and the mixture was stirred under reflux. Water (0.2 mL) was then added portionwise.

Once the residue was dissolved, the mixture was stirred overnight as it was allowed to cool. Subsequently, the mixture was stirred and cooled with ice for 1 hour and was suction-filtered. The resulting solid was washed with isopropanol and dried to give 162 mg (74% yield) of the desired product as pale yellow crystals.

Example 117

Production of 2-(5-amino-4,6-dimethylpyrimidine-2-yloxy)-N-(1-benzylpiperidine-4-yl)-N-methylacetamide maleate (Compound 117)

Compound 65 (1.0 g) was suspended in methanol (5.0 mL) and maleic acid (307 mg) was added to the suspension at room temperature (20 to 30° C.). After the compound was dissolved, the mixture was concentrated under reduced pressure. Then, isopropanol (5.0 mL) was added to the resulting residue and the mixture was stirred under reflux. Water (0.4 mL) was then added portionwise. Once the residue was dissolved, the mixture was stirred overnight as it was allowed to cool. Subsequently, the mixture was stirred and cooled with ice for 1 hour and was suction-filtered. The resulting solid was washed with isopropanol and dried to give 1.1 g (86% yield) of the desired product as white crystals.

Example 118

Production of 2-(5-amino-4,6-dimethylpyrimidine-2-yloxy)-N-(1-benzylpiperidine-4-yl)-N-methylacetamide methanesulfonate (Compound 118)

Compound 65 (202 mg) was suspended in methanol (1 mL) and methanesulfonic acid (50.6 mg) was added to the suspension at room temperature (20 to 30° C.). After the compound was dissolved, the mixture was concentrated under reduced pressure. Then, isopropanol (1.0 mL) was added to the resulting residue and the mixture was stirred under reflux. Once the residue was dissolved, the mixture was stirred overnight as it was allowed to cool. Subsequently, the mixture was stirred and cooled with ice for 1 hour and was suction-filtered. The resulting solid was washed with isopropanol and dried to give 232 mg (92% yield) of the desired product as white crystals.

Example 119

Production of 2-(5-amino-4,6-dimethylpyrimidine-2-yloxy)-N-(1-benzylpiperidine-4-yl)-N-methylacetamide nitrate (Compound 119)

Compound 65 (186 mg) was suspended in methanol (1 mL) and nitric acid (44.3 mg: d=1.42) was added to the suspension at room temperature (20 to 30° C.). After the compound was dissolved, the mixture was concentrated under reduced pressure. Then, isopropanol (2.0 mL) was added to the resulting residue and the mixture was stirred under reflux. Water (240 µL) was then added portionwise. Once the residue was dissolved, the mixture was stirred overnight as it was allowed to cool. Subsequently, the mixture was stirred and cooled with ice for 1 hour, and was suction-filtered. The resulting solid was washed with isopropanol and dried to give 116 mg (54% yield) of the desired product as white crystals.

Example 120

Production of 2-(5-amino-4,6-dimethylpyrimidine-2-yloxy)-N-(1-benzylpiperidine-4-yl)-N-methylacetamide tosylate (Compound 120)

Compound 65 (201 mg) was suspended in methanol (1 mL) and p-tosylic acid monohydrate (99.3 mg) was added to the suspension at room temperature (20 to 30° C.). After the compound was dissolved, the mixture was concentrated under reduced pressure. Then, isopropanol (2.0 mL) was added to the resulting residue and the mixture was stirred under reflux. Water (150 µL) was then added portionwise. Once the residue was dissolved, the mixture was stirred overnight as it was allowed to cool. Subsequently, the mixture was stirred and cooled with ice for 1 hour, and was suction-filtered. The resulting solid was washed with isopropanol and dried to give 247 mg (84% yield) of the desired product as white crystals.

Example 121

Production of 2-(5-amino-4,6-dimethylpyrimidine-2-yloxy)-N-(1-benzylpiperidine-4-yl)-N-methylacetamide ethanesulfonate (Compound 121)

Compound 65 (202 mg) was suspended in methanol (1 mL) and ethanesulfonic acid (58.8 mg) was added to the suspension at room temperature (20 to 30° C.). After the compound was dissolved, the mixture was concentrated under reduced pressure. Then, ethanol (2.0 mL) was added to the resulting residue and the mixture was stirred under reflux. Water (100 µL) was then added portionwise. Once the residue was dissolved, the mixture was stirred overnight as it was allowed to cool. Subsequently, the mixture was stirred and cooled with ice for 1 hour, and was suction-filtered. The resulting solid was washed with ethanol and dried to give 181 mg (70% yield) of the desired product as white crystals.

Example 122

Production of 2-(5-amino-4,6-dimethylpyrimidine-2-yloxy)-N-(1-benzylpiperidine-4-yl)-N-methylacetamide benzenesulfonate (Compound 122)

Compound 65 (200 mg) was suspended in methanol (1 mL) and benzenesulfonic acid monohydrate (83.4 mg) was added to the suspension at room temperature (20 to 30° C.). After the compound was dissolved, the mixture was concentrated under reduced pressure. Then, isopropanol (2.0 mL) was added to the resulting residue and the mixture was stirred under reflux. Water (230 µL) was then added portionwise. Once the residue was dissolved, the mixture was stirred overnight as it was allowed to cool. Subsequently, the mixture was stirred and cooled with ice for 1 hour, and was suction-filtered. The resulting solid was washed with isopropanol and dried to give 194 mg (69% yield) of the desired product as white crystals.

Example 123

Production of N-(1-benzylpiperidine-4-yl)-N-methyl-2-(3-methyl-5-nitropyridine-2-ylamino)acetamide (Compound 123)

The title compound was synthesized from 2-chloro-3-methyl-5-nitropyridine and 2-amino-N-(1-benzylpiperidine-4-yl)-N-methylacetamide in the same manner as in Example 10.

Example 124

Production of 2-(5-amino-3-methylpyridine-2-yloxy)-N-(1-benzylpiperidine-4-yl)-N-methylacetamide hydrochloride (Compound 124)

The title compound was synthesized from Compound 61 in the same manner as in Example 76.

Example 125

Production of N-(1-benzylpiperidine-4-yl)-2-(5-chloropyridine-3-yloxy)-N-methylacetamide hydrochloride (Compound 125)

The title compound was synthesized from 2-(5-chloropyridine-3-yloxy)acetic acid in the same manner as in Example 95.

Example 126

Production of 2-(5-chloropyridine-3-yloxy)-N-(1-(cyclopropylmethyl)piperidine-4-yl)-N-methylacetamide hydrochloride (Compound 126)

The title compound was synthesized from 2-(5-chloropyridine-3-yloxy)acetic acid and 1-(cyclopropylmethyl)-N-methylpiperidine-4-amine in the same manner as in Example 95.

Example 127

Production of N-(1-benzylpiperidine-4-yl)-2-(3-chloropyrazine-2-ylamino)-N-methylacetamide hydrochloride (Compound 127)

The title compound was synthesized from Compound 23 in the same manner as in Example 95.

Example 128

Production of N-(1-benzylpiperidine-4-yl)-2-(3-chloropyrazine-2-yloxy)-N-methylacetamide hydrochloride (Compound 128)

The title compound was synthesized from Compound 26 in the same manner as in Example 95.

Example 129

Production of N-(1-benzylpiperidine-4-yl)-2-(6-chloropyrazine-2-yloxy)-N-methylacetamide hydrochloride (Compound 129)

The title compound was synthesized from Compound 27 in the same manner as in Example 95.

Example 130

Production of N-(1-benzylpiperidine-4-yl)-N-methyl-2-(3-(methylamino)pyrazine-2-yloxy)acetamide hydrochloride (Compound 130)

A 30% solution of methylamine in ethanol (120 mg) was added to an ethanol solution (1 mL) of Compound 128 (100 mg) and the mixture was irradiated with microwave (160° C., 30 min). The reaction mixture was concentrated under reduced pressure. To the resulting residue, water was added and the product was extracted with ethyl acetate. The organic layer was dried over sodium sulfate, filtered, and concentrated under reduced pressure. The resulting residue was purified by amino-coated silica gel (Fuji Sylysia Chemical Ltd.,; MH-DM1020) column chromatography (hexane:ethyl acetate=1:2) and formed into a hydrochloride to give 68.1 mg (63% yield) of the title compound.

Example 131

Production of N-(1-benzylpiperidine-4-yl)-N-methyl-2-(6-(methylamino)pyrazine-2-yloxy)acetamide hydrochloride (Compound 131)

The title compound was synthesized from Compound 129 in the same manner as in Example 130.

Example 132

Production of N-(1-benzylpiperidine-4-yl)-2-(3-(dimethylamino)pyrazine-2-yloxy)-N-methylacetamide maleate (Compound 132)

The title compound was synthesized from Compound 128 and dimethylamine hydrochloride in the same manner as in Example 130.

Example 133

Production of N-(1-benzylpiperidine-4-yl)-2-(6-(dimethylamino)pyrazine-2-yloxy)-N-methylacetamide hydrochloride (Compound 133)

The title compound was synthesized from Compound 129 and dimethylamine hydrochloride in the same manner as in Example 130.

Example 134

Production of 2-(3-aminopyrazine-2-yloxy)-N-(1-benzylpiperidine-4-yl)-N-methylacetamide hydrochloride (Compound 134)

(4-Methoxyphenyl)methylamine (40 mg) was added to an ethanol solution (1 mL) of Compound 128 (100 mg) and the mixture was irradiated with microwave (160° C., 100 min). The reaction mixture was concentrated under reduced pressure. To the resulting residue, water was added and the product was extracted with ethyl acetate. The organic layer was dried over sodium sulfate, filtered, and concentrated under reduced pressure. The resulting residue was purified by amino-coated silica gel (Fuji Sylysia Chemical Ltd.,; MH-DM1020) column chromatography (hexane:ethyl acetate=1:1) to give a colorless oily material (46.7 mg). Then, this product was dissolved in chloroform (1 mL) and trifluoroacetic acid (1 mL) was added to the solution. The mixture was stirred at room temperature overnight. Subsequently, the reaction mixture was concentrated under reduced pressure and water was added to the residue. The resulting product was extracted with chloroform. The organic layer was dried over sodium sulfate, filtered, and concentrated under reduced pressure. The resulting residue was purified by amino-coated silica gel (Fuji Sylysia Chemical Ltd.,; MH-DM1020) column chromatography (ethyl acetate) and formed into a hydrochloride to give 21.5 mg (21% yield) of the title compound.

Example 135

Production of 2-(6-chloropyridazine-3-yloxy)-N-(1-(cyclopropanecarbonyl)piperidine-4-yl)-N-methylacetamide (Compound 135)

The title compound was synthesized from ethyl 2-(6-chloropyridazine-3-yloxy)acetate and cyclopropyl (4-(methylamino)piperidine-1-yl)methanone in the same manner as in Example 105 (63% yield, in 2 steps).

Example 136

Production of N-(1-(cyclopropanecarbonyl)piperidine-4-yl)-2-(6-(dimethylamino)pyridazine-3-yloxy)-N-methylacetamide (Compound 136)

A mixture of Compound 135 (60 mg), 2M dimethylamine/tetrahydrofuran solution (766 μL), potassium iodide (2.82 mg), triethylamine (23.7 μL) and n-butanol (1.0 mL) was stirred at 110° C. for 2 days in a sealed tube. Subsequently, the reaction mixture was concentrated under reduced pressure and the resulting residue was purified by silica gel column chromatography (ethyl acetate:hexane=1:3 to 99:1) to give 12.1 mg (19% yield) of the desired product as a pale yellow amorphous.

Example 137

Production of N-(1-benzylpiperidine-4-yl)-2-(6-chloropyridazine-3-yloxy)-N-methylacetamide (Compound 137)

The title compound was synthesized from ethyl 2-(6-chloropyridazine-3-yloxy)acetate in the same manner as in Example 104 (48% yield, in 2 steps).

Example 138

Production of N-(1-benzylpiperidine-4-yl)-2-(6-chloropyridazine-3-yloxy)-N-cyclopropylacetamide (Compound 138)

The title compound was synthesized from ethyl 2-(6-chloropyridazine-3-yloxy)acetate and 1-benzyl N-cyclopropylpiperidine-4-amine in the same manner as in Example 104.

Example 139

Production of N-(1-benzylpiperidine-4-yl)-2-(3,5-dichloropyridazine-4-ylamino)-N-methylacetamide (Compound 139)

The title compound was synthesized from Compound 29 in the same manner as in Example 104.

Example 140

Production of N-(1-benzylpiperidine-4-yl)-2-(3-chloro-5-methoxypyridazine-4-ylamino)-N-methylacetamide (Compound 140)

A solution of Compound 139 (10 mg) and sodium methoxide (1.3 mg) in methanol (MIL) was stirred overnight under reflux. The reaction mixture was concentrated under reduced pressure and the resulting residue was purified by amino-coated silica gel (Fuji Sylysia Chemical Ltd.,; NH-DM1020) column chromatography (ethyl acetate:hexane=1:9 to 1:1) to give 3.0 mg (30% yield) of the desired product as a white amorphous.

Example 141

Production of N-(1-benzylpiperidine-4-yl)-2-(5,6-dichloropyridazine-4-ylamino)-N-methylacetamide (Compound 141)

The title compound was synthesized from Compound 28 in the same manner as in Example 104.

The physical property data of the compounds produced in Examples above are summarized in Tables 1 to 24.

TABLE 1

| Compd. No | Chemical Structure | Properties (mp) | MS(+) | 1H-NMR (CDCl$_3$) |
|---|---|---|---|---|
| 1 | 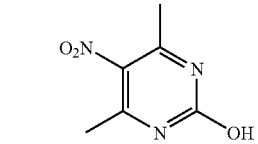 | Yellow solid (Washed with methylene chloride) (198-201° C.) | 170 (M + H) | (DMSO) 2.44 (6H, s), 12.66 (1H, brs) |
| 2 | 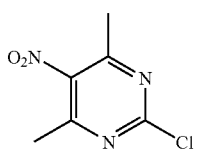 | Yellow amorphous | 188 (M + H) | 2.59 (6H, s) |
| 3 | 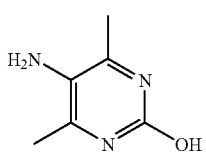 | Yellow solid | 140 (M + H) | (DMSO) 2.15 (6H, s), 3.99 (2H, s), 11.00 (1H, brs) |

TABLE 1-continued

| Compd. No | Chemical Structure | Properties (mp) | MS(+) | 1H-NMR (CDCl3) |
|---|---|---|---|---|
| 4 | 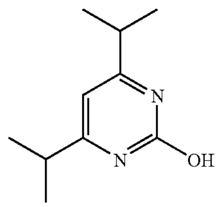 | Brown amorphous | 181 (M + H) | 1.33 (12H, d), 3.00 (2H, sept), 6.35 (1H, s) |
| 5 | 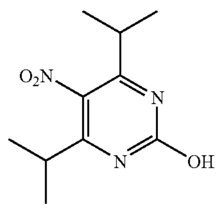 [SMILES: CC(C)c1nc(O)nc(C(C)C)c1[N+](=O)[O-]] | Brown amorphous | 226 (M + H) | 1.37 (12H, d), 3.04 (2H, sept) |
| 6 | 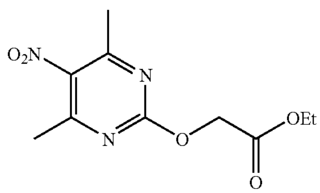 [SMILES: CCOC(=O)COc1nc(C)c([N+](=O)[O-])c(C)n1] | Yellow solid | 256 (M + H) | 1.28 (3H, t), 2.52 (6H, s), 4.25 (2H, q), 4.94 (2H, s) |

TABLE 2

| Compd. No | Chemical Structure | Properties (mp) | MS(+) | 1H-NMR (CDCl3) |
|---|---|---|---|---|
| 7 | 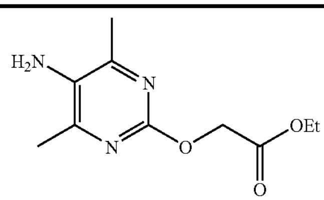 | Pale yellow solid | | 1.26 (3H, t), 2.32 (6H, s), 3.26 (2H, brs), 4.22 (2H, q), 4.82 (2H, s) |
| 8 | 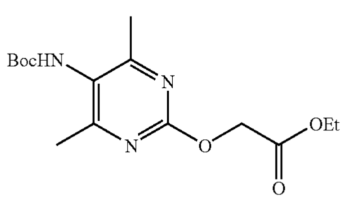 [SMILES: CCOC(=O)COc1nc(C)c(NC(=O)OC(C)(C)C)c(C)n1] | White solid (131-134° C.) | 326 (M + H) | 1.26 (3H, t), 1.50 (9H, brs), 2.39 (6H, s), 4.23 (2H, q), 4.87 (2H, s), 5.62-5.90 (1H, brs) |
| 9 | 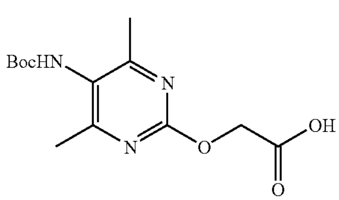 [SMILES: Cc1nc(OCC(=O)O)nc(C)c1NC(=O)OC(C)(C)C] | White solid (168-169° C.) | 298 (M + H) | (CD3OD) 1.35-151 (9H, m), 2.35 (6H, s), 4.89 (2H, s) |
| 10 | 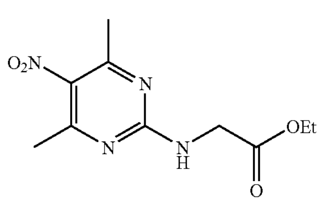 [SMILES: CCOC(=O)CNc1nc(C)c([N+](=O)[O-])c(C)n1] | Pale yellow amorphous | 2.55 (M + H) | 1.30 (3H, t), 2.47 (6H, s), 4.20-4.30 (4H, m), 5.91 (1H, brs) |

TABLE 2-continued

| Compd. No | Chemical Structure | Properties (mp) | MS(+) | 1H-NMR (CDCl₃) |
|---|---|---|---|---|
| 11 | (O₂N, dimethyl pyrimidine, NH-CH₂-COOH) | Pale yellow amorphous | 227 (M + H) | 2.41-2.58 (6H, m), 4.35 (2H, d), 7.69 (1H, brs) |
| 12 | (BocHN, dimethyl pyrimidine, O-CH(CH₃)-COOH) | Pale yellow amorphous | 312 (M + H) | 1.34-1.59 (9H, brs), 1.66 (3H, d), 2.36 (6H, s), 5.32 (1H, q), 5.96 & 6.71 (1H, each brs) |

TABLE 3

| Compd. No | Chemical Structure | Properties (mp) | MS(+) | 1H-NMR (CDCl₃) |
|---|---|---|---|---|
| 13 | (H₂N, diisopropyl pyrimidine, O-CH₂-CO-OEt) | Pale yellow amorphous | 282 (M + H) | 1.19-1.35 (3H, m), 1.25 (12H, d), 2.99 (2H, sept), 3.33 (2H, brs), 4.20 (2H, q), 4.79 (2H, s) |
| 14 | (Cl, methyl pyrimidine, NH-CH₂-CO-OEt) | White amorphous | | 1.32 (3H, t), 2.08 (3H, d), 4.24-4.33 (4H, m), 5.34 (1H, brs), 7.88 (1H, d) |
| 15 | (Cl, methyl pyrimidine, O-C(CH₃)₂-CO₂Et) | Colorless oily material | 259 (M + H) | 1.22 (3H, t), 1.71 (6H, s), 2.14 (3H, d), 4.20 (2H, q), 8.12 (1H, d) |
| 16 | (Cl, methyl pyrimidine, O-C(CH₃)₂-CO₂H) | White amorphous | 231 (M + H) | 1.76 (6H, s), 2.14 (3H, brs), 8.15 (1H, d) |
| 17 | (H₂N, dimethyl pyrimidine, O-CH₂-CO₂Et) | Brown amorphous | | (DMSO) 1.22 (3H, t), 2.20 (6H, s), 4.17 (2H, q), 4.42 (2H, s), 6.21 (2H, brs) |
| 18 | (F, H₂N, pyrimidinone, N-CH₂-CO₂Et) | White amorphous | | (DMSO) 1.20 (3H, t), 4.13 (2H, q), 4.39 (2H, s), 7.52 (1H, brs), 7.76 (1H, brs), 7.94 (1H, d) |

TABLE 4

| Compd. No | Chemical Structure | Properties (mp) | MS(+) | 1H-NMR (CDCl3) |
|---|---|---|---|---|
| 19 | O2N-pyridine(Me)-O-CH2-C(=O)-OEt | Brown amorphous | 241 (M + H) | 1.29 (3H, t), 2.35 (3H, s), 4.24 (2H, q), 5.01 (2H, s), 8.23 (1H, d), 8.86 (1H, d) |
| 20 | BocHN-pyridine(Me)-O-CH2-C(=O)-OEt | Yellow oily material | 311 (M + H) | 1.26 (3H, t), 1.51 (9H, s), 2.25 (3H, s), 4.21 (2H, q), 4.86 (2H, s), 6.29-6.41 (1H, brs), 7.75 (1H, d), 8.02 (1H, brs) |
| 21 | BocHN-pyridine(Me)-O-CH2-C(=O)-OH | Pale yellow amorphous | 283 (M + H) | (DMSO) 1.46 (9H, s), 2.15 (3H, s), 4.76 (2H, s), 7.67 (1H, s), 7.91 (1H, s), 9.25 (1H, brs), 12.57-12.98 (1H, brs) |
| 22 | 3-Cl-pyrazine-NH-CH2-CO2Et | Colorless oily material | 216 (M + H) | 1.31 (3H, t), 4.22 (2H, d), 4.26 (2H, q), 5.72 (1H, brs), 7.65 (1H, d), 7.95 (1H, d) |
| 23 | 3-Cl-pyrazine-NH-CH2-CO2H | White solid (149-150° C.) | 188 (M) | (CD3OD) 4.13 (2H, s), 7.57 (1H, d), 7.96 (1H, d) |
| 24 | 3-Cl-pyrazine-O-CH2-CO2Et | Colorless oily material | 217 (M + H) | 1.28 (3H, t), 4.24 (2H, q), 4.98 (2H, s), 7.99 (1H, d), 8.00 (1H, d) |

TABLE 5

| Compd. No | Chemical Structure | Properties (mp) | MS(+) | 1H-NMR (CDCl3) |
|---|---|---|---|---|
| 25 | 6-Cl-pyrazine-O-CH2-CO2Et | Colorless oily material | 217 (M + H) | 1.30 (3H, t), 4.26 (2H, q), 4.91 (2H, s), 8.21 (1H, s), 8.27 (1H, s) |
| 26 | 3-Cl-pyrazine-O-CH2-CO2H | White solid (144-145° C.) | 188 (M) | 5.03 (2H, s), 8.01 (1H, d), 8.03 (1H, d) |
| 27 | 6-Cl-pyrazine-O-CH2-CO2H | White solid | 188 (M) | 4.99 (2H, s), 8.23 (1H, s), 8.28 (1H, s) |
| 28 | 3,4-diCl-pyridazine-NH-CH2-CO2Et | Pale pink amorphous | 250 (M + H) | 1.35 (3H, t), 4.09 (2H, d), 4.33 (2H, q), 5.59 (1H, brs), 8.46 (1H, s) |

TABLE 5-continued

| Compd. No | Chemical Structure | Properties (mp) | MS(+) | 1H-NMR (CDCl₃) |
|---|---|---|---|---|
| 29 | 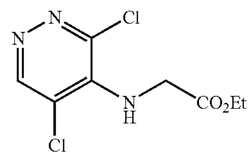 [SMILES: CCOC(=O)CNc1c(Cl)cnnc1Cl] | Pale white amorphous | 250 (M + H) | 1.33 (3H, t), 4.31 (2H, q), 4.50 (2H, d), 5.80 (1H, brs), 8.66 (1H, s) |
| 30 | 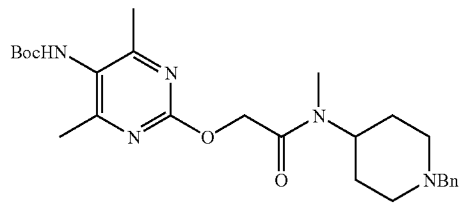 [SMILES: Cc1nc(OCC(=O)N(C)C2CCN(Cc3ccccc3)CC2)nc(C)c1NC(=O)OC(C)(C)C] | Yellow amorphous | 484 (M + H) | 1.32-2.14 (6H, m), 1.50 (9H, brs), 2.36 (6H, s), 2.80-3.03 (2H, m), 2.85 & 2.92 (3H, each s), 3.48-3.57 & 4.45 (1H, each m), 3.49 & 3.52 (2H, each s), 4.96 & 5.01 (2H, each s), 5.77 (1H, brs), 7.21-7.37 (5H, m) |

TABLE 6

| Compd. No | Chemical Structure | Properties (mp) | MS(+) | 1H-NMR (CDCl₃) |
|---|---|---|---|---|
| 31 | 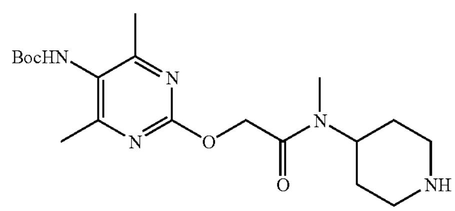 | White solid (99-100° C.) | 394 (M + H) | 140-1.80 (13H, m), 2.37 (6H, s), 2.66-273 (2H, m), 2.86 & 2.93 (3H, each s), 3.10-3.20 (2H, m), 3.48 (1H, s), 3.56-3.62 & 4.48-4.53 (1H, each m), 4.96 & 5.02 (1H, each s), 5.63 & 5.86 (1H, each brs) |
| 32 | 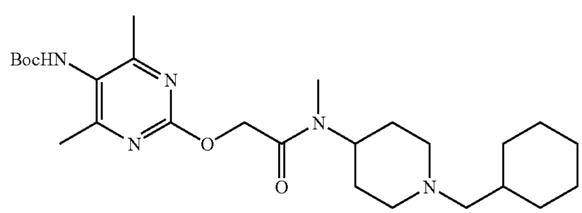 [SMILES: Cc1nc(OCC(=O)N(C)C2CCN(CC3CCCCC3)CC2)nc(C)c1NC(=O)OC(C)(C)C] | White solid | 490 (M + H) | 0.81-0.90 (2H, m), 1.13-1.28 (3H, m), 1.40-1.76 (18H, m), 1.92-1.99 (2H, m), 2.08-2.12 (2H, m), 2.37 (6H, s), 2.85-2.95 (5H, m), 3.45-3.55 & 4.45 (1H, each m), 4.96 & 5.02 (2H, each s), 5.50 & 5.76 (1H, each brs) |
| 33 | 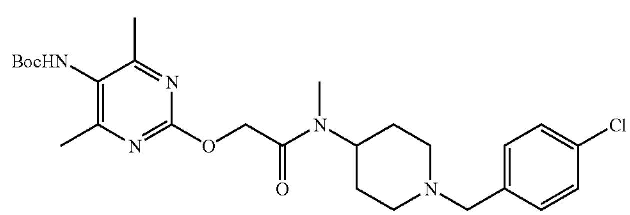 [SMILES: Cc1nc(OCC(=O)N(C)C2CCN(Cc3ccc(Cl)cc3)CC2)nc(C)c1NC(=O)OC(C)(C)C] | White solid | 518 (M + H) | 1.38-1.80 (13H, m), 1.88-2.10 (2H, m), 2.37 (6H, s), 2.85-2.97 (5H, m), 3.43-3.55 (2H, m), 3.43-3.55 & 4.40-4.46 (1H, each m), 4.96 & 5.01 (2H, each s), 5.50 & 5.77 (1H, each brs), 7.23-7.29 (4H, m) |
| 34 | 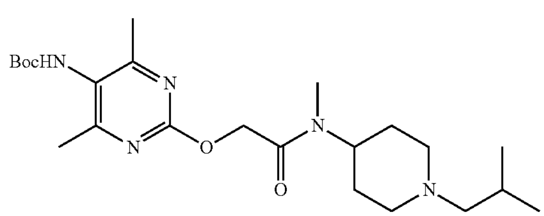 [SMILES: Cc1nc(OCC(=O)N(C)C2CCN(CC(C)C)CC2)nc(C)c1NC(=O)OC(C)(C)C] | White solid | 450 (M + H) | 0.87-0.90 (6H, m), 1.38-1.62 (10H, m), 1.68-1.78 (3H, m), 1.89-2.08 (5H, m), 2.37 (6H, s), 2.85-2.97 (5H, m), 3.43-3.53 & 4.37-4.44 (1H, each m), 4.96 & 5.02 (2H, each s), 5.48 & 5.75 (1H, each brs) |

TABLE 6-continued

| Compd. No | Chemical Structure | Properties (mp) | MS(+) | 1H-NMR (CDCl₃) |
|---|---|---|---|---|
| 35 | 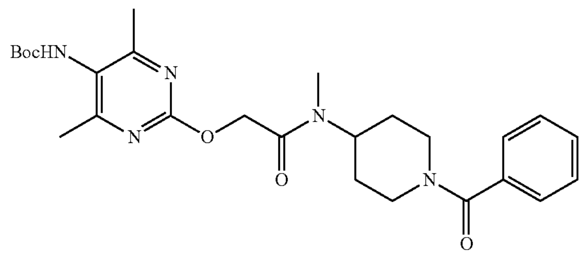 [SMILES: Cc1nc(OCC(=O)N(C)C2CCN(C(=O)c3ccccc3)CC2)nc(C)c1NC(=O)OC(C)(C)C] | White solid | 498 (M + H) | 1.38-1.80 (13H, m), 2.37 (6H, s), 2.75-3.20 (5H, m), 3.80-3.90 (1H, m), 3.80-3.90 & 4.66-4.72 (1H, each m), 4.80-5.05 (3H, m), 5.60 & 5.85 (1H, each brs), 7.39-7.45 (5H, m) |
| 36 | 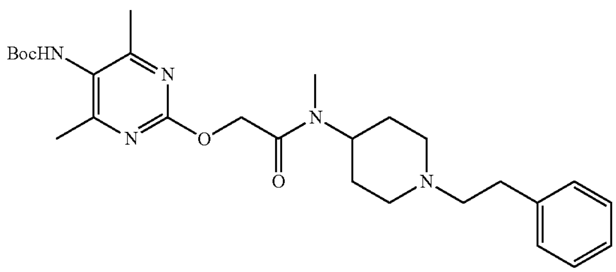 [SMILES: Cc1nc(OCC(=O)N(C)C2CCN(CCc3ccccc3)CC2)nc(C)c1NC(=O)OC(C)(C)C] | White solid | 498 (M + H) | 1.40-1.55 (9H, m), 1.63-1.80 (4H, m), 1.90-2.21 (2H, m), 2.38 (6H, s), 2.53-2.66 (2H, m), 2.77-2.82 (2H, m), 2.87 & 2.94 (3H, each s), 3.05-3.13 (2H, m), 3.50-3.58 & 4.44-4.50 (1H, each m), 4.97 & 5.02 (2H, each s), 5.55 & 5.80 (1H, each brs), 7.15-7.34 (5H, m) |

TABLE 7

| Compd. No | Chemical Structure | Properties (mp) | MS(+) | 1H-NMR (CDCl₃) |
|---|---|---|---|---|
| 37 | 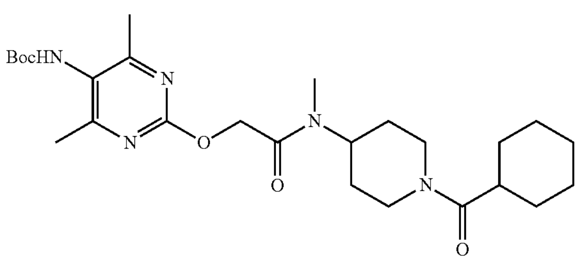 | Colorless oily material | 504 (M + H) | 1.22-1.85 (23H, m), 2.38 (6H, s), 2.42-2.57 (2H, m), 2.82 & 2.90 (3H, each s), 3.05-3.11 (1H, m), 3.73-3.83 & 4.62-4.69 (1H, each m), 3.95-4.02 (1H, m), 4.72-4.80 (1H, m), 4.93-5.05 (2H, m), 5.55 & 5.80 (1H, each brs) |
| 38 | 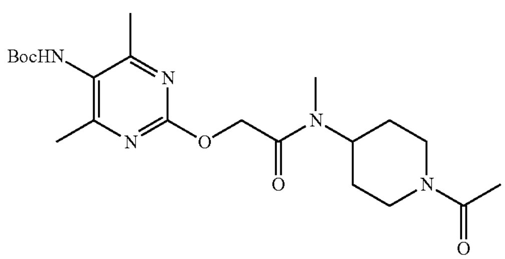 [SMILES: CC(=O)N1CCC(N(C)C(=O)COc2nc(C)c(NC(=O)OC(C)(C)C)c(C)n2)CC1] | White solid | 436 (M + H) | 1.40-1.85 (13H, m), 2.11 (3H, s), 2.38 (6H, s), 2.53-2.60 (1H, m), 2.82 & 2.90 (3H, each s), 3.10-3.17 (1H, m), 3.80-3.95 (1H, m), 3.80-3.95 & 4.62-4.70 (1H, each m), 4.70-4.76 (1H, m), 4.92-5.03 (2H, m), 5.60 & 5.83 (1H, each brs) |
| 39 | 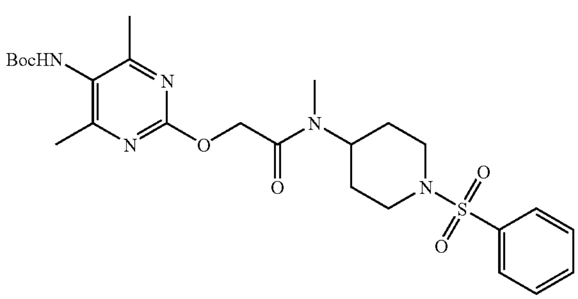 [SMILES: Cc1nc(OCC(=O)N(C)C2CCN(S(=O)(=O)c3ccccc3)CC2)nc(C)c1NC(=O)OC(C)(C)C] | White solid | 534 (M + H) | 1.33-1.56 (9H, m), 1.62-1.68 (2H, m), 1.75-2.04 (2H, m), 2.30-2.37 (8H, m), 2.81 & 2.90 (3H, each s), 3.47-3.57 & 4.31-4.37 (1H, each m), 3.88-3.98 (2H, m), 4.90-4.93 (2H, m), 5.50 & 5.76 (1H, each brs), 7.52-7.63 (3H, m), 7.73-7.79 (2H, m) |

TABLE 7-continued

| Compd. No | Chemical Structure | Properties (mp) | MS(+) | 1H-NMR (CDCl₃) |
|---|---|---|---|---|
| 40 | (structure) | White solid | 476 (M + H) | 1.08-1.28 (5H, m), 1.40-1.55 (9H, m), 1.62-1.90 (9H, m), 2.28-2.37 (9H, m), 2.82-3.01 (5H, m), 3.40-3.50 & 4.37-4.41 (1H, each m), 4.96 & 5.01 (2H, each s), 5.52 & 5.77 (1H, each brs) |
| 41 | (structure) | White amorphous | 505 (M + H) | 1.41-1.84 (19H, m), 2.37 (6H, s), 2.80-2.91 (5H, m), 3.13-3.21 (4H, m), 3.65-3.78 (2H, m), 3.65-3.78 & 4.50-4.60 (1H, each m), 4.96 & 5.03 (2H, each s), 5.75 & 5.93 (1H, each brs) |
| 42 | (structure) | Colorless oily material | 498 (M + H) | 1.40-1.60 (10H, m), 1.67-1.95 (3H, m), 2.05-2.12 (2H, m), 2.35 (3H, s), 2.37 (6H, s), 2.84-3.03 (5H, m), 3.43 & 3.46 (2H, each s), 3.47-3.57 & 4.41-4.48 (1H, each m), 4.95 & 5.02 (2H, each s), 5.58 & 5.81 (1H, each brs), 7.13-7.26 (4H, m) |

TABLE 8

| Compd. No | Chemical Structure | Properties (mp) | MS(+) | 1H-NMR (CDCl₃) |
|---|---|---|---|---|
| 43 | (structure) | White solid (107-109° C.) | 470 (M + H) | 1.40-1.55 (9H, m), 1.70-2.05 (4H, m), 2.38 (6H, s), 2.79-2.94 (5H, m), 3.72-3.80 (2H, m), 3.72-3.80 & 4.55-4.65 (1H, m), 4.99 & 5.06 (2H, each s), 5.48 & 5.76 (1H, each s), 6.84 (1H, t), 6.94 (2H, d), 7.22-7.28 (2H, m) |
| 44 | (structure) | Pale Yellow oily material | 452 (M + H) | 1.35-1.63 (11H, m), 1.70-1.85 (2H, m), 1.94-2.11 (2H, m), 2.37 (6H, m), 2.52-2.60 (2H, m), 2.85 & 2.92 (3H, each s), 2.99-3.09 (2H, m), 3.36 (3H, d), 3.47-3.52 (2H, m), 3.47-3.52 & 4.39-4.48 (1H, each m), 4.96 & 5.01 (2H, each s), 5.66 & 5.88 (1H, each brs) |
| 45 | (structure) | White amorphous (69-70° C.) | 485 (M + H) | 1.41-1.61 (10H, m), 1.69-2.13 (5H, m), 2.36 (6H, s), 2.85-2.97 (5H, m), 3.49-3.53 (2H, m), 3.49-3.53 & 4.40-4.48 (1H, each m), 4.94 & 5.00 (2H, each s), 6.10 & 6.19 (1H, each brs), 7.23-7.28 (1H, m), 7.63-7.66 (1H, m), 8.49-8.54 (2H, m) |

TABLE 8-continued

| Compd. No | Chemical Structure | Properties (mp) | MS(+) | 1H-NMR (CDCl₃) |
|---|---|---|---|---|
| 46 | (structure: BocHN-dimethylpyrimidine-O-CH₂-C(O)-N(Me)-piperidine-N-CH₂-(4-fluorophenyl)) | White amorphous (84-85° C.) | 502 (M + H) | 1.40-2.08 (15H, m), 2.37 (6H, s), 2.85-2.98 (5H, m), 3.44 & 3.48 (2H, each s), 3.44-3.51 & 4.40-4.47 (1H, each m), 4.96 & 5.01 (2H, each s), 5.50 & 5.77 (1H, each brs), 6.97 & 7.02 (2H, m), 7.24-7.28 (2H, m) |
| 47 | (structure: BocHN-dimethylpyrimidine-O-CH₂-C(O)-N(Me)-piperidine-N-CH₂-tetrahydrofuran) | White amorphous (59-90° C.) | 478 (M + H) | 1.40-2.15 (19H, m), 2.37 (6H, s), 2.42-2.52 (2H, m), 2.84 & 2.91 (3H, each s), 3.04-3.15 (2H, m), 3.46-3.50 & 4.39-4.44 (1H, each m), 3.71-3.75 (1H, m), 3.85-3.89 (1H, m), 3.97-4.03 (1H, m), 4.96 & 5.01 (2H, each s), 5.50 & 5.77 (1H, each brs) |
| 48 | (structure: BocHN-dimethylpyrimidine-O-CH₂-C(O)-N(Me)-piperidine-N-pyridin-3-yl) | Colorless oily material | 471 (M + H) | 1.39-1.51 (9H, m), 1.73-1.92 (4H, m), 2.39 (6H, s), 2.85-2.95 (5H, m), 3.74-3.81 (2H, m), 3.74-3.81 & 4.59-4.65 (1H, each m), 4.99 & 5.05 (2H, each s), 5.89 & 5.65 (1H, each brs), 7.14-7.21 (2H, m), 8.07-8.11 (1H, m), 8.32 (1H, s) |

TABLE 9

| Compd. No | Chemical Structure | Properties (mp) | MS(+) | 1H-NMR (CDCl₃) |
|---|---|---|---|---|
| 49 | (structure: BocHN-dimethylpyrimidine-O-CH₂-C(O)-N(Me)-piperidine-N-CH₂-cyclopropyl) | Pale yellow amorphous | 448 (M + H) | 0.10 (2H, m), 0.52 (2H, m), 0.85 (1H, m), 1.32-2.10 (6H, m), 1.50 (9H, brs), 2.21-2.30 (2H, m), 2.38 (6H, s), 2.86 & 2.93 (3H, each s), 3.09-3.23 (2H, m), 3.43-3.57 & 4.44 (1H, each m), 4.97 & 5.02 (2H, each s), 5.47 & 5.75 (1H, each brs) |
| 50 | (structure: BocHN-dimethylpyrimidine-O-CH₂-C(O)-N(Me)-piperidine-N-CH₂-(3-methoxyphenyl)) | Colorless oily material | 514 (M + H) | 1.35-1.62 (10H, m), 1.70-2.01 (3H, m), 2.03-2.10 (2H, m), 2.37 (6H, s), 2.86-3.00 (5H, m), 3.46 & 3.50 (2H, each s), 3.45-3.52 & 4.40-4.46 (1H, each m), 3.81 (3H, s), 4.96 & 5.01 (2H, each s), 5.55 & 5.80 (1H, each brs), 6.78-6.90 (3H, m), 7.22 (1H, t) |

TABLE 9-continued

| Compd. No | Chemical Structure | Properties (mp) | MS(+) | 1H-NMR (CDCl₃) |
|---|---|---|---|---|
| 51 | 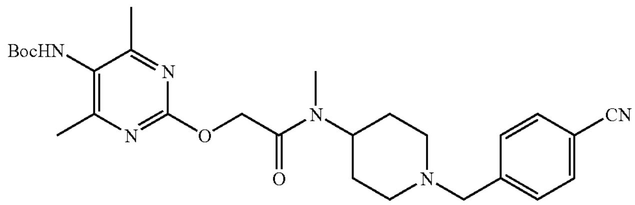 [SMILES: Cc1nc(OCC(=O)N(C)C2CCN(Cc3ccc(C#N)cc3)CC2)nc(C)c1NC(=O)OC(C)(C)C] | White solid (71-72° C.) | 509 (M + H) | 1.31-1.50 (9H, m), 1.55-1.95 (4H, m), 2.00-2.14 (2H, m), 2.37 (6H, s), 2.86-2.94 (5H, m), 3.52 & 3.55 (2H, each s), 3.51-3.57 & 4.40-4.47 (1H, each m), 4.96 & 5.01 (2H, each s), 5.50 & 5.78 (1H, each brs), 7.44 (2H, d), 7.61 (2H, d) |
| 52 | 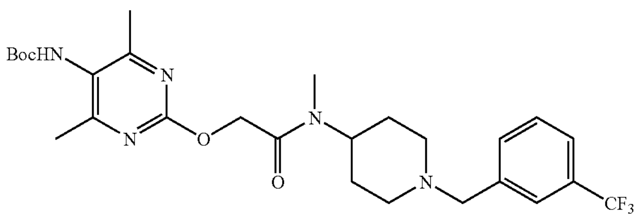 [SMILES: Cc1nc(OCC(=O)N(C)C2CCN(Cc3cccc(C(F)(F)F)c3)CC2)nc(C)c1NC(=O)OC(C)(C)C] | Colorless oily material | 552 (M + H) | 1.35-1.52 (9H, m), 1.58-2.00 (4H, m), 2.05-2.13 (2H, m), 2.37 (6H, s), 2.86-2.97 (5H, m), 3.53 & 3.56 (2H, each s), 3.52-3.58 & 4.40-4.50 (1H, each m), 4.96 & 5.01 (2H, each s), 5.56 & 5.82 (1H, each brs), 7.42-7.59 (4H, m) |
| 53 | 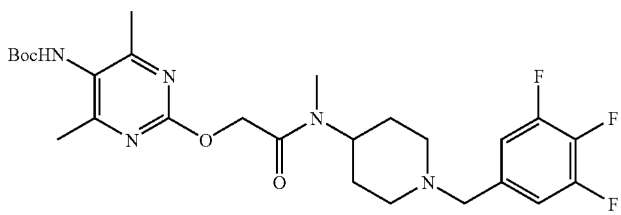 [SMILES: Cc1nc(OCC(=O)N(C)C2CCN(Cc3cc(F)c(F)c(F)c3)CC2)nc(C)c1NC(=O)OC(C)(C)C] | Colorless oily material | 538 (M + H) | 1.45-1.55 (9H, m), 1.58-1.94 (4H, m), 2.04-2.12 (2H, m), 2.37 (6H, s), 2.83-2.94 (5H, m), 3.40 & 3.42 (2H, each s), 3.52-3.58 & 4.40-4.49 (1H, each m), 4.96 & 5.01 (2H, each s), 5.55 & 5.81 (1H, each brs), 6.96 (2H, t) |
| 54 | 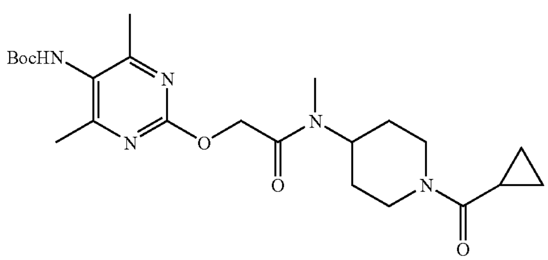 [SMILES: Cc1nc(OCC(=O)N(C)C2CCN(C(=O)C3CC3)CC2)nc(C)c1NC(=O)OC(C)(C)C] | Colorless oily material | 462 (M + H) | 0.75-0.78 (2H, m), 0.95-1.00 (2H, m), 1.40-1.50 (9H, m), 1.60-1.81 (5H, m), 2.38 (6H, s), 2.53-2.65 (1H, m), 2.83 & 2.90 (3H, each s), 3.13-3.20 (1H, m), 3.78-3.85 & 4.65-4.75 (2H, each m), 4.28-4.32 (1H, m), 4.96-5.08 (2H, m), 5.58 & 5.81 (1H, each brs) |

TABLE 10

| Compd. No. | Chemical Structure | Properties (mp) | MS(+) | 1H-NMR (CDCl₃) |
|---|---|---|---|---|
| 55 | 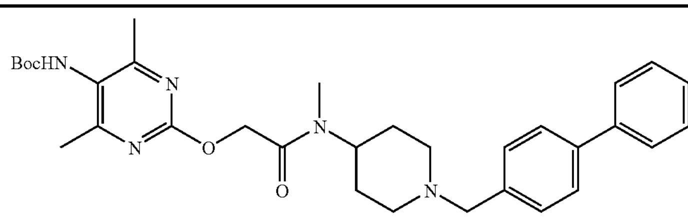 | Colorless oily material | 560 (M + H) | 1.41-1.51 (9H, m), 1.58-2.13 (6H, m), 2.37 (6H, s), 2.86-3.04 (5H, m), 3.52-3.56 (2H, m), 3.52-3.56 & 4.40-4.50 (1H, each m), 4.96 & 5.02 (2H each s), 5.50 & 5.78 (1H, each brs), 7.31-7.45 (5H, m), 7.53-7.60 (4H, m) |

TABLE 10-continued

| Compd. No. | Chemical Structure | Properties (mp) | MS(+) | 1H-NMR (CDCl₃) |
|---|---|---|---|---|
| 56 | 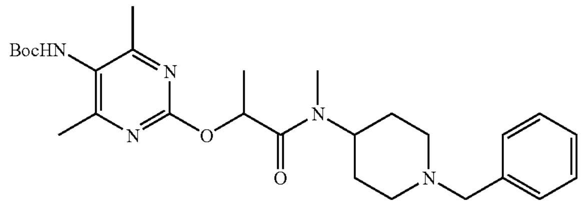 [SMILES: Cc1nc(OC(C)C(=O)N(C)C2CCN(Cc3ccccc3)CC2)nc(C)c1NC(=O)OC(C)(C)C] | White amorphous | 498 (M + H) | 1.29-2.12 (9H, m), 1.49 (9H, brs), 2.33 (6H, s), 2.80-3.04 (2H, m), 2.84 & 3.01 (3H, each s), 3.45-3.55 (2H, m), 3.64-3.75 & 4.47 (1H, each m), 5.38-5.60 (1H, m), 5.72 (1H, brs), 7.20-7.35 (5H, m) |
| 57 | 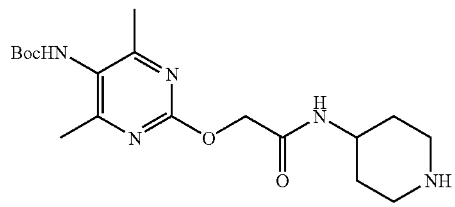 [SMILES: Cc1nc(OCC(=O)NC2CCNCC2)nc(C)c1NC(=O)OC(C)(C)C] | White amorphous | 380 (M + H) | 1.28-1.60 (11H, m), 1.92 (2H, m), 2.42 (6H, s), 2.69 (2H, m), 3.03-3.12 (2H, m), 3.98 (1H, m), 4.85 (2H, s), 5.85 (1H, brs), 6.55 (1H, brd,) |
| 58 | 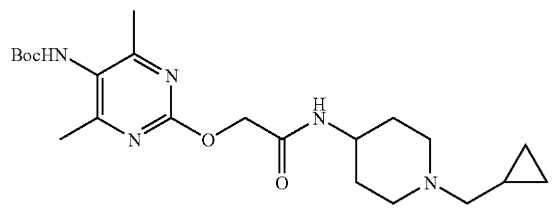 [SMILES: Cc1nc(OCC(=O)NC2CCN(CC3CC3)CC2)nc(C)c1NC(=O)OC(C)(C)C] | White amorphous | | 0.09 (2H, m), 0.50 (2H, m), 0.85 (1H, m), 1.35-1.68 (11H, m), 1.89-1.98 (2H, m), 2.10 (2H, m), 2.24 (2H, d), 2.42 (6H, s), 3.01 (2H, m), 3.88 (1H, m), 4.85 (2H, s), 5.82 (1H, brs), 6.50 (1H, brd,) |
| 59 | 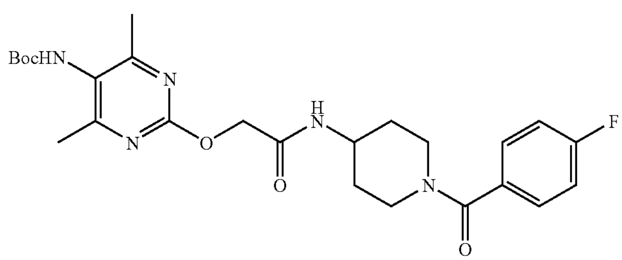 [SMILES: Cc1nc(OCC(=O)NC2CCN(C(=O)c3ccc(F)cc3)CC2)nc(C)c1NC(=O)OC(C)(C)C] | White amorphous | 502 (M + H) | 1.32-1.68 (11H, m), 1.99 (2H, m), 2.43 (6H, s), 2.82-3.22 (2H, m), 3.65-3.87 (1H, m), 4.09-4.21 (1H, m), 4.55-4.75 (1H, m), 4.86 (2H, s), 5.83 (1H, brs), 6.59 (1H, brd), 7.10 (2H, m), 7.38-7.45 (2H, m) |
| 60 | 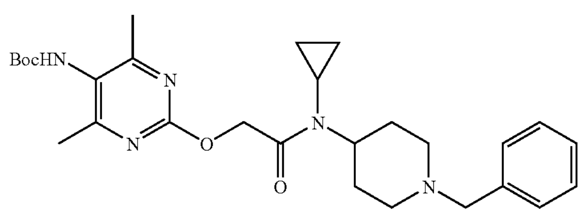 [SMILES: Cc1nc(OCC(=O)N(C2CC2)C2CCN(Cc3ccccc3)CC2)nc(C)c1NC(=O)OC(C)(C)C] | White amorphous | 510 (M + H) | 0.85-0.98 (4H, m), 1.50 (9H, brs), 1.68 (2H, m), 1.97-2.10 (4H, m), 2.35 (6H, s), 2.62 (1H, m), 2.91 (2H, m), 3.48 (2H, s), 4.07 (1H, brs), 5.12 (2H, s), 5.75 (1H, brs), 7.20-7.32 (5H, m) |

TABLE 11

| Compd. No | Chemical Structure | Properties (mp) | MS(+) | 1H-NMR (CDCl₃) |
|---|---|---|---|---|
| 61 | 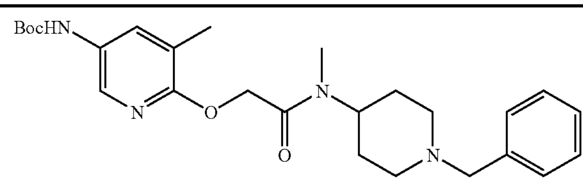 | White amorphous | 469 (M + H) | 1.31-2.12 (6H, m), 1.50 & 1.51 (9H, each s), 2.23 & 2.26 (3H, each s), 2.80-3.03 (2H, m), 2.86 & 2.90 (3H, each s), 3.48 (2H, m), 3.52-3.67 & 4.46 (1H, each m), 4.97 & 5.00 (2H, each s), 6.27 (1H, brs), 7.19-7.36 (5H, m), 7.60-7.79 (2H, m) |

TABLE 11-continued

| Compd. No | Chemical Structure | Properties (mp) | MS(+) | 1H-NMR (CDCl₃) |
|---|---|---|---|---|
| 62 | (structure) | Pale yellow amorphous | 413 (M + H) | 1.41-2.19 (6H, m), 2.48 (6H, s), 2.80-3.05 (5H, m), 3.40-3.58 & 4.50 (1H, each m), 3.51 & 3.56 (2H, each s), 4.18 & 4.21 (2H, each d), 6.46-6.61 (1H, m), 7.19-7.38 (5H, m) |
| 63 | (structure) | Pale yellow amorphous (82-85° C.) | 383 (M + H) | 1.48-2.27 (6H, m), 2.28 & 2.29 (6H, each s), 2.84-3.03 (2H, m), 2.88 & 2.90 (3H, each s), 3.43-3.65 & 4.51 (1H, each m), 3.50 & 3.54 (2H, each s), 4.12 & 4.17 (2H, each d), 5.57 (1H, m), 7.21-7.39 (5H, m) |
| 64 | (structure) | White solid (122-127° C.) | 427 (M + H) | 1.50-2.18 (6H, m), 2.31 (6H, s), 2.81-3.01 (2H, m), 2.85 & 2.94 (3H, each s), 3.21 (2H, brs), 3.46-3.62 & 4.45 (1H, each m), 3.53 & 3.56 (2H, each s), 4.91 & 4.97 (2H, each s), 5.39-5.71 (1H, brs), 5.87-6.20 (1H, brs), 7.40 (2H, d), 7.76 (2H, d) |
| 65 | (structure) | White crystal (164-166° C.) | 384 (M + H) | 1.54-2.14 (6H, m), 2.31 (6H, s), 2.83-3.04 (2H, m), 2.85 & 2.93 (3H, each s), 3.21 (2H, brs), 3.49 & 3.51 (2H, each s), 3.57 & 4.45 (1H, each m), 4.90 & 4.96 (2H, each s), 7.22-7.38 (5H, m) |
| 66 | (structure) 2HCl | White crystal (Methanol/ ethyl acetate) (208-212° C.) | 348 (M + H) | (CD₃OD) 0.40-0.51 (2H, m), 0.71-0.83 (2H, m), 1.13 (1H, m), 1.87-2.33 (4H, m), 2.33 (6H, each s), 2.86 & 3.03 (3H, each s), 3.00-3.25 (4H, m), 3.70-3.82 (2H, m), 4.10 & 4.52 (1H, each m), 5.01 & 5.11 (2H, each s) |

TABLE 12

| Compd. No | Chemical Structure | Properties (mp) | MS(+) | 1H-NMR (CDCl3) |
|---|---|---|---|---|
| 67 | 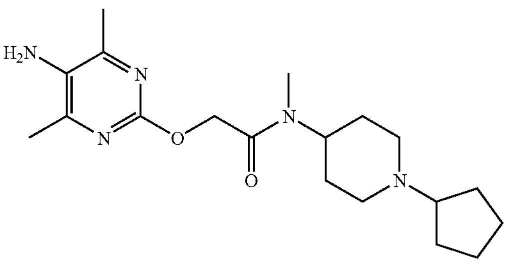 [SMILES: Cc1nc(OCC(=O)N(C)C2CCN(C3CCCC3)CC2)nc(C)c1N] | White amorphous (202-206° C.) | 362 (M + H) | 1.30-1.46 (2H, m), 1.46-2.09 (12H, m), 2.32 (6H, s), 2.48 (1H, m), 2.85 & 2.93 (3H, each s), 3.03-3.19 (2H, m), 3.21 (2H, brs), 3.56 & 4.46 (1H, each m), 4.91 & 4.98 (2H, each s) |
| 68 | 2HCl | White crystal (Ether/methanol) (202-206° C.) | 404 (M + H) | (CD3OD) 0.94-1.09 (2H, m), 1.13-1.42 (4H, m), 1.56-1.81 (7H, m), 1.85-2.20 (4H, m), 2.31 (6H, s), 2.84 & 3.01 (3H, each s), 2.95-3.19 (4H, m), 3.55-3.70 (2H, m), 4.02-4.13 & 4.48 (1H, each m), 4.97 & 5.06 (2H, each s) |
| 69 | 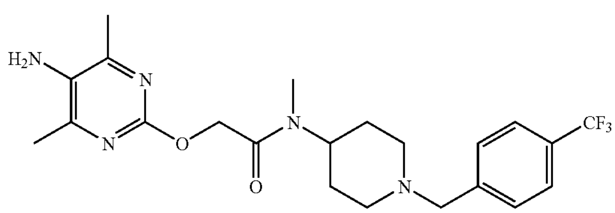 [SMILES: Cc1nc(OCC(=O)N(C)C2CCN(Cc3ccc(C(F)(F)F)cc3)CC2)nc(C)c1N] | Pale yellow crystal (Methylene chloride) (176-179° C.) | 452 (M + H) | 1.52-2.16 (6H, m), 2.31 (6H, s), 2.85-3.03 (2H, m), 2.86 & 2.94 (3H, each s), 3.21 (2H, brs), 3.50-3.64 & 4.46 (1H, each m), 3.52 & 3.55 (2H, each s), 4.91 & 4.97 (2H, each s), 7.44 (2H, d), 7.57 (2H, d) |
| 70 | 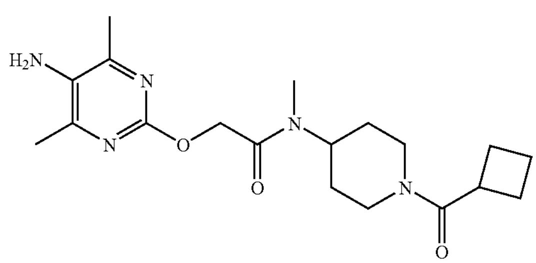 [SMILES: Cc1nc(OCC(=O)N(C)C2CCN(C(=O)C3CCC3)CC2)nc(C)c1N] | Pale yellow amorphous (79-83° C.) | 376 (M + H) | 1.39-2.22 (8H, m), 2.26-2.42 (2H, m), 2.32 (6H, s), 2.57 (1H, m), 2.80 & 2.89 (3H, each s), 3.01 (1H, m), 3.15-3.31 & 4.60-4.80 (5H, m), 3.70-3.86 (1H, m), 4.90 & 4.92 (2H, each s) |
| 71 | 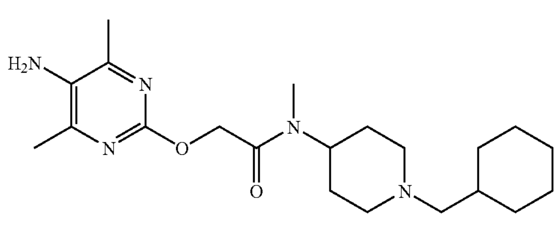 [SMILES: Cc1nc(OCC(=O)N(C)C2CCN(CC3CCCCC3)CC2)nc(C)c1N] | White solid (151-152° C.) | 390 (M + H) | 0.80-0.89 (2H, m), 1.13-1.27 (3H, m), 1.40-1.76 (9H, m), 1.88-1.99 (3H, m), 2.07-2.10 (2H, m), 2.32 (6H, s), 2.84-2.95 (5H, m), 3.21 (2H, s), 3.45-3.55 & 4.35-4.45 (1H, each m), 4.91 & 4.97 (2H, each s) |
| 72 | 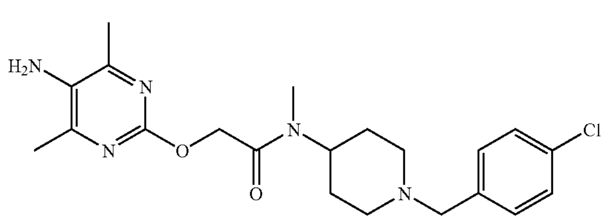 [SMILES: Cc1nc(OCC(=O)N(C)C2CCN(Cc3ccc(Cl)cc3)CC2)nc(C)c1N] | White solid (60-61° C.) | 418 (M + H) | 1.56-2.09 (6H, m), 2.31 (6H, s), 2.84-2.96 (5H, m), 3.21 (2H, s), 3.43 & 3.47 (2H, each s), 3.50-3.60 & 4.41-4.48 (1H, each m), 4.90 & 4.96 (2H, each s), 7.22-7.29 (4H, m) |

TABLE 13

| Compd No. | Chemical Structure | Properties (mp) |
|---|---|---|
| 73 | 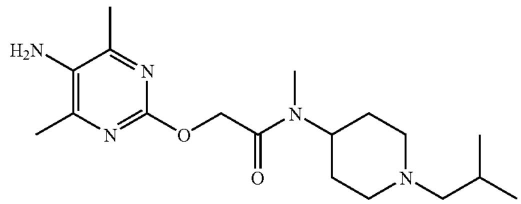 [SMILES: Cc1nc(OCC(=O)N(C)C2CCN(CC(C)C)CC2)nc(C)c1N] | White solid (180-181° C.) |
| 74 | 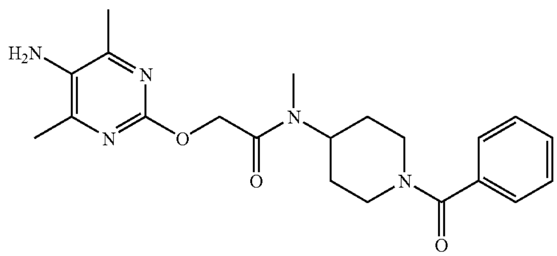 [SMILES: Cc1nc(OCC(=O)N(C)C2CCN(C(=O)c3ccccc3)CC2)nc(C)c1N] | White solid (216-217° C.) |
| 75 | 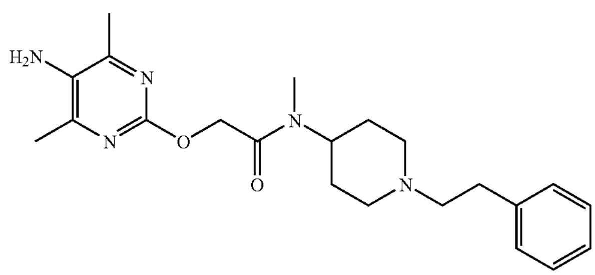 [SMILES: Cc1nc(OCC(=O)N(C)C2CCN(CCc3ccccc3)CC2)nc(C)c1N] | White solid (153-154° C.) |
| 76 | H—Cl | Pale yellow solid (100-102° C.) |
| 77 | H—Cl | White solid (58-60° C.) |
| 78 | 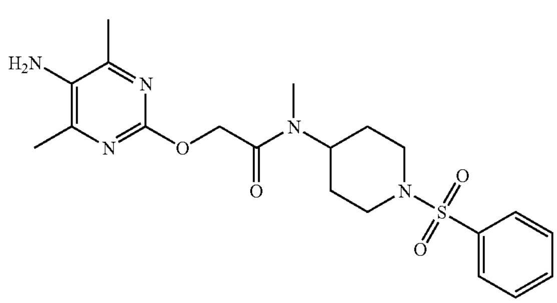 [SMILES: Cc1nc(OCC(=O)N(C)C2CCN(S(=O)(=O)c3ccccc3)CC2)nc(C)c1N] | White amorphous (231-232° C.) |

TABLE 13-continued

| Compd No. | MS(+) | 1H-NMR (CDCl₃) |
|---|---|---|
| 73 | 350(M + H) | 0.87-0.90 (6H, m), 1.52-1.78 (4H, m), 1.88-2.07 (5H, m), 2.31 (6H, s), 2.85-2.96 (5H, m), 3.23 (2H, s), 3.48-3.58 & 4.39-4.46 (1H, each m), 4.91 & 4.98 (2H, each s) |
| 74 | 398(M + H) | 1.54-1.80 (4H, m), 2.32 (6H, s), 2.75-3.00 (4H, m), 3.00-3.25 (3H, m), 3.80-3.90 (1H, m), 3.80-3.90 & 4.65-4.75 (1H, each m), 4.82-5.02 (3H, m), 7.39-7.43 (5H, m) |
| 75 | 398(M + H) | 1.61-2.16 (6H, m), 2.32 (6H, s), 2.56-2.61 (2H, m), 2.77-2.94 (5H, m), 3.04-3.12 (2H, m), 3.22 (2H, s), 3.52-3.60 & 4.44-4.51 (1H, each m), 4.92 & 4.98 (2H, each s), 7.18-7.28 (5H, m) |
| 76 | 404(M + H) | (CD₃OD) 1.20-1.99 (14H, m), 2.47 (6H, s), 2.56-2.68 (2H, m), 2.81 & 2.94 (3H, each s), 3.09-3.25 (1H, m), 3.34 (2H, s), 3.84-3.94 & 4.49-4.53 (1H, each m), 4.11-4.19 (1H, m), 4.64-4.70 (1H, m), 5.21 & 5.34 (2H, each s) |
| 77 | 336(M + H) | (CD₃OD) 1.62-1.93 (4H, m), 2.11 & 2.14 (3H, each s), 2.50 (6H, s), 2.59-2.75 (1H, m), 2.82 & 2.95 (3H, each s), 3.12-3.28 (1H, m), 3.31 (2H, s), 3.83-3.89 & 4.46-4.54 (1H, each m), 3.99-4.07 (1H, m), 4.62-4.69 (1H, m), 5.26 & 5.39 (2H, each s) |
| 78 | 434(M + H) | 1.64-2.03 (4H, m), 2.28-2.37 (8H, m), 2.80 & 2.90 (3H, each s), 3.22 (2H, s), 3.53-3.63 & 4.32-4.38 (1H, each m), 3.88-4.00 (2H, m), 4.88 (2H, s), 7.52-7.63 (3H, m), 7.74-7.76 (2H, d) |

TABLE 14

| Compd No. | Chemical Structure | Properties (mp) |
|---|---|---|
| 79 | [Structure: 5-amino-4,6-dimethylpyrimidin-2-yl-O-CH₂-C(O)-N(CH₃)-piperidin-4-yl-N-cyclohexyl] | White amorphous (187-188° C.) |
| 80 | [Structure: 5-amino-4,6-dimethylpyrimidin-2-yl-O-CH₂-C(O)-N(CH₃)-piperidin-4-yl-N-C(O)-piperidinyl] | White solid (200-201° C.) |
| 81 | [Structure: 5-amino-4,6-dimethylpyrimidin-2-yl-O-CH₂-C(O)-N(CH₃)-piperidin-4-yl-N-CH₂-(2-methylphenyl)] | White amorphous (144-146° C.) |
| 82 | [Structure: 5-amino-4,6-dimethylpyrimidin-2-yl-O-CH₂-C(O)-N(CH₃)-piperidin-4-yl-N-phenyl] | White amorphous (59-61° C.) |

TABLE 14-continued

| | | | |
|---|---|---|---|
| 83 | 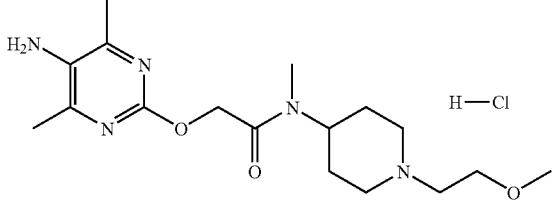 | H—Cl | Pale yellow solid (194-195° C.) |
| 84 | 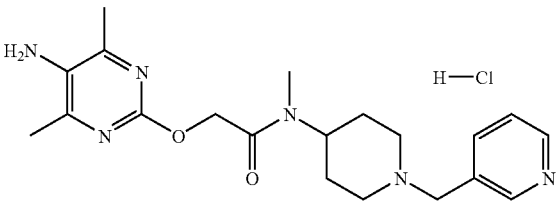 | H—Cl | White solid (142-143° C.) |

| Compd No. | MS(+) | 1H-NMR (CDCl₃) |
|---|---|---|
| 79 | 376(M + H) | 0.88-1.32 (7H, m), 1.56-1.90 (7H, m), 2.25-2.37 (9H, m), 2.85-3.01 (5H, m), 3.21 (2H, s), 3.45-3.55 & 4.38-4.45 (1H, each m), 4.91 & 4.97 (2H, s) |
| 80 | 405(M + H) | 1.55-1.85 (10H, m), 2.32 (6H, s), 2.75-2.92 (5H, m), 3.15-3.25 (6H, m), 3.71-3.77 (2H, m), 3.71-3.77 & 4.56-4.60 (1H, each m), 4.92 & 4.99 (2H, each s) |
| 81 | 398(M + H) | 1.58-1.90 (4H, m), 2.04-2.12 (2H, m), 2.31 (6H, s), 2.35 (3H, s), 2.73-2.98 (5H, m), 3.21 (2H, s), 3.42 & 3.45 (2H, each s), 3.50-3.60 & 4.40-4.50 (1H, each m), 4.90-4.98 (2H, each s), 7.15-7.26 (4H, m) |
| 82 | 370(M + H) | 1.71-2.05 (4H, m), 2.33 (6H, s), 2.74-2.95 (5H, m), 3.22 (2H, s), 3.72-3.80 (2H, m), 3.72-3.80 & 4.58-4.64 (1H, each m), 4.97 & 5.02 (2H, each s), 6.85 (1H, t), 6.94 (2H, d), 7.23-7.28 (2H, m) |
| 83 | 352(M + H) | (CD₃OD) 1.82-2.21 (4H, m), 2.31 (6H, s), 2.84-3.13 (5H, m), 3.22-3.37 (2H, m), 3.41 (3H, s), 3.55-3.65 (2H, m), 3.67-3.71 (2H, m), 4.02-4.08 & 4.45-4.52 (1H, each m), 4.97 & 5.02 (2H, each s) |
| 84 | 385(M + H) | (CD₃OD) 1.86-2.20 (4H, m), 2.30 (6H, s), 2.82 & 3.00 (3H, each s), 3.12-3.16 (2H, m), 3.50-3.60 (2H, m), 4.05-4.11 & 4.46-4.52 (1H, each m), 4.34-4.40 (2H, m), 4.97 & 5.05 (2H, each s), 7.56-7.59 (1H, m), 8.01-8.05 (1H, m), 8.66-8.71 (2H, m) |

TABLE 15

| Compd No. | Chemical Structure | Properties (mp) |
|---|---|---|
| 85 | 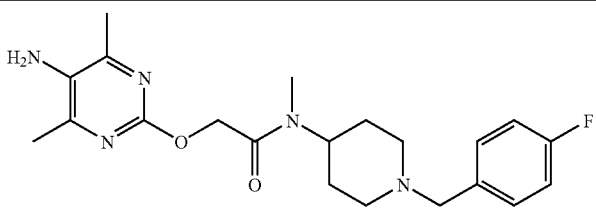 | White amorphous (54-55° C.) |
| 86 | 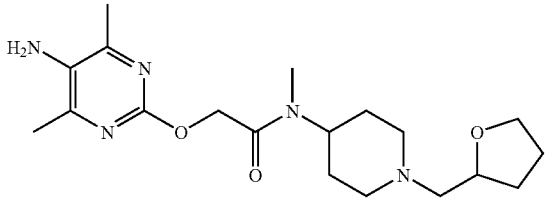 [SMILES: Cc1nc(OCC(=O)N(C)C2CCN(CC3CCCO3)CC2)nc(C)c1N] | White amorphous (158-159° C.) |

TABLE 15-continued

| | Structure | Description |
|---|---|---|
| 87 | (5-amino-4,6-dimethylpyrimidin-2-yloxy)acetamide with N-methyl-piperidin-4-yl, N-(pyridin-3-yl), HCl | Pale yellow solid (120-121° C.) |
| 88 | (5-amino-4,6-dimethylpyrimidin-2-yloxy)acetamide with N-methyl-piperidin-4-yl, N-(3-methoxybenzyl), HCl | White solid (139-140° C.) |
| 89 | (5-amino-4,6-dimethylpyrimidin-2-yloxy)acetamide with N-methyl-piperidin-4-yl, N-(4-cyanobenzyl), HCl | White solid (124-125° C.) |
| 90 | (5-amino-4,6-dimethylpyrimidin-2-yloxy)acetamide with N-methyl-piperidin-4-yl, N-(3-trifluoromethylbenzyl) | White amorphous (40-50° C.) |

| Compd No. | MS(+) | 1H-NMR (CDCl₃) |
|---|---|---|
| 85 | 402(M + H) | 1.56-2.08 (6H, m), 2.31 (6H, s), 2.84-2.97 (5H, m), 3.21 (2H, s), 3.44 & 3.47 (2H, each s), 3.50-3.60 & 4.42-4.48 (1H, m), 4.91 & 4.97 (2H, each s), 6.97-7.01 (2H, m), 7.24-7.28 (2H, m) |
| 86 | 378(M + H) | 1.40-1.62 (3H, m), 1.71-2.15 (7H, m), 2.32 (6H, s), 2.34-2.52 (2H, m), 2.84 & 2.92 (3H, each s), 3.04-3.11 (2H, m), 3.21 (2H, s), 3.51-3.57 & 4.41-4.49 (1H, each m), 3.71-3.77 (1H, m), 3.85-3.91 (1H, m), 3.98-4.04 (1H, m) |
| 87 | 371(M + H) | (CD₃OD) 1.73-1.99 (4H, m), 2.32 (6H, s), 2.83 & 2.99 (3H, each s), 3.03-3.11 (2H, m), 4.01-4.04 (2H, m), 4.01-4.04 & 4.52-4.55 (1H, each m), 4.98 & 5.08 (2H, each s), 7.67-7.70 (1H, m), 7.94-7.96 (1H, m), 8.03-8.05 (1H, m), 8.35 (1H, s) |
| 88 | 414(M + H) | (CD₃OD) 1.75-1.90 (2H, m), 2.03-2.20 (2H, m), 2.30 (6H, s), 2.82 & 3.00 (3H, each s), 3.05-3.20 (2H, m), 3.50-3.60 (2H, m), 3.84 (3H, s), 4.03-4.13 & 4.45-4.55 (1H, each m), 4.28 (2H, s), 4.96 & 5.05 (2H, each s), 7.06-7.11 (3H, m), 7.40 (1H, t, J = 7.9 Hz) |
| 89 | 409(M + H) | (CD₃OD) 1.76-2.14 (4H, m), 2.30 (6H, s), 2.69-3.00 (5H, m), 3.29-3.36 (2H, m), 3.88-3.98 & 4.41-4.49 (1H, each m), 4.08 & 4.16 (2H, each s), 4.96 & 5.04 (2H, each s), 7.67 (2H, d, J = 8.1 Hz), 7.81 (1H, d, J = 8.1 Hz) |
| 90 | 452(M + H) | 1.59-2.15 (6H, m), 2.31 (6H, s), 2.86-2.96 (5H, m), 3.21 (2H, s), 3.52-3.55 (2H, each s), 3.52-3.55 & 4.42-4.49 (1H, each m), 4.91 & 4.97 (2H, each s), 7.40-7.59 (4H, m) |

TABLE 16

| Compd. No. | Chemical Structure | Properties (mp) |
|---|---|---|
| 91 | 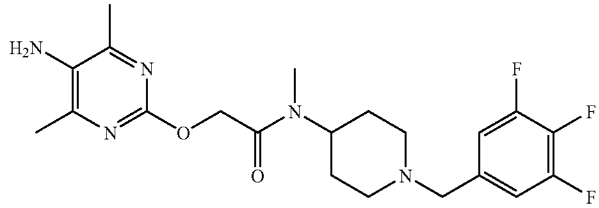 [SMILES: Cc1nc(OCC(=O)N(C)C2CCN(Cc3cc(F)c(F)c(F)c3)CC2)nc(C)c1N] | White solid (146-147° C.) |
| 92 | 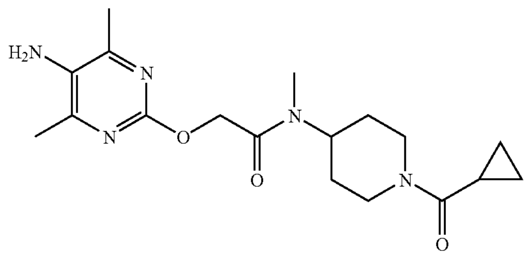 [SMILES: Cc1nc(OCC(=O)N(C)C2CCN(C(=O)C3CC3)CC2)nc(C)c1N] | White amorphous (85-86° C.) |
| 93 | 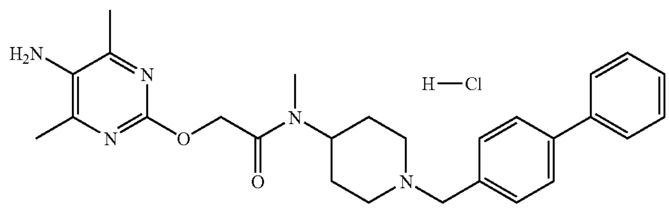 | White solid (229-230° C.) |
| 94 | 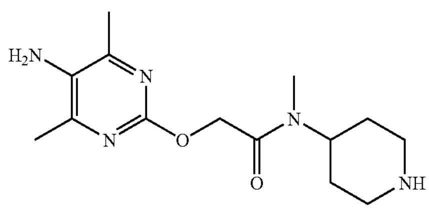 [SMILES: Cc1nc(OCC(=O)N(C)C2CCNCC2)nc(C)c1N] | White amorphous (161-163° C.) |
| 95 | 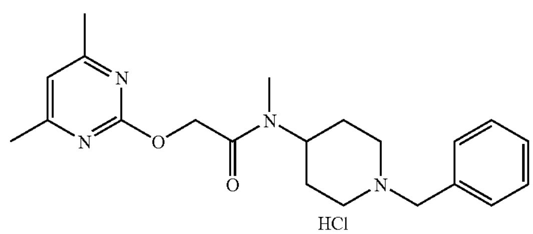 [SMILES: Cc1cc(C)nc(OCC(=O)N(C)C2CCN(Cc3ccccc3)CC2)n1 ; Cl] | White amorphous (65-70° C.) |
| 96 | 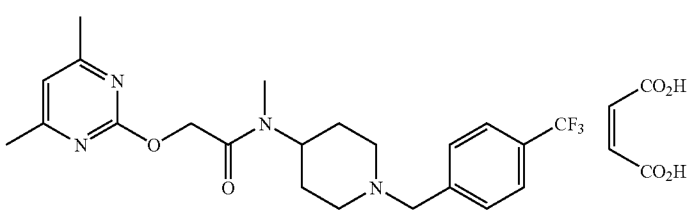 | White solid (170-173° C.) |

| Compd. No. | MS($^+$) | 1H-NMR (CDCl$_3$) |
|---|---|---|
| 91 | 438(M + H) | 1.58-2.15 (6H, m), 2.31 (6H, s), 2.84-2.95 (5H, m), 3.22 (2H, s), 3.39 & 3.42 (2H, each s), 3.52-3.62 & 4.42-4.49 (1H, each m), 4.91 & 4.97 (2H, each s), 6.93-6.99 (2H, m) |
| 92 | 362(M + H) | 0.74-0.77 (2H, m), 0.94-1.02 (2H, m), 1.54-1.78 (5H, m), 2.33 (6H, s), 2.57-2.65 (1H, m), 2.82 & 2.91 (3H, each s), 3.05-3.23 (3H, m), 3.80-3.90 & 4.28-4.31 (1H, each m), 4.66-4.73 (2H, m), 4.91-5.00 (2H, m) |

TABLE 16-continued

| | | |
|---|---|---|
| 93 | 460(M + H) | (CD$_3$OD) 1.85-2.15 (4H, m), 2.30 (6H, s), 2.82 & 3.00 (3H, each s), 3.12-3.14 (2H, m), 3.52-3.61 (2H, m), 4.00-4.10 & 4.45-4.55 (1H, each m), 4.34 (2H, s), 4.97 & 5.05 (2H, each s), 7.38 (1H, t), 7.47 (2H, dd), 7.59 (2H, d), 7.65 (2H, d), 7.76 (2H, d) |
| 94 | 294(M + H) | 1.53-1.83 (4H, m), 2.32 (6H, s), 2.70 (2H, m), 2.86 & 2.94 (3H, each s), 3.10-3.28 (4H, m), 3.64 & 4.53 (1H, each m), 4.91 & 4.99 (2H, each s) |
| 95 | 369(M + H) | (CD$_3$OD) 1.69-2.11 (4H, m), 2.37 (6H, s), 2.48-2.73 (2H, m), 2.83 & 2.99 (3H, each s), 3.18-3.46 (2H, m), 3.78-3.90 & 4.35-4.47 (1H, each m), 3.85 & 3.93 (2H, each s), 5.07 & 5.15 (2H, each s), 6.87 (1H, s), 7.41 (5H, m) |
| 96 | 437(M + H) | (DMSO) 1.55-1.71 (2H, m), 1.81-2.09 & 2.23-2.37 (4H, m), 2.30 (6H, s), 2.62-3.07 (2H, m), 2.70 & 2.87 (3H, each s), 3.73-3.93 & 4.08-4.47 (3H, m), 4.97 & 5.07 (2H, each s), 6.08 (2H, s), 6.87 (1H, s), 7.70 (2H, m), 7.84 (2H, m) |

TABLE 17

| Compd. No. | Chemical Structure | Properties (mp) |
|---|---|---|
| 97 | 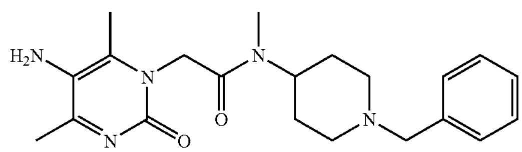 [SMILES: Cc1nc(=O)n(CC(=O)N(C)C2CCN(Cc3ccccc3)CC2)c(C)c1N] | Pale yellow amorphous (97-102° C.) |
| 98 | 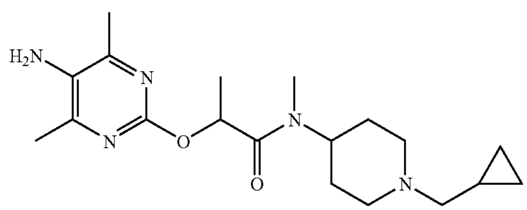 [SMILES: Cc1nc(OC(C)C(=O)N(C)C2CCN(CC3CC3)CC2)nc(C)c1N] | White amorphous (139-144° C.) |
| 99 | 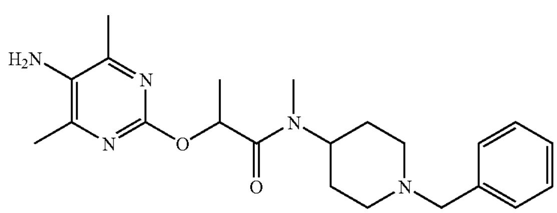 | White amorphous (181-185° C.) |
| 100 | 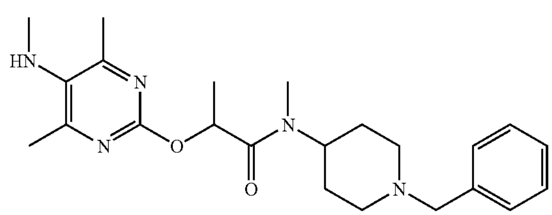 [SMILES: CNc1c(C)nc(OC(C)C(=O)N(C)C2CCN(Cc3ccccc3)CC2)nc1C] | Pale yellow amorphous |
| 101 | 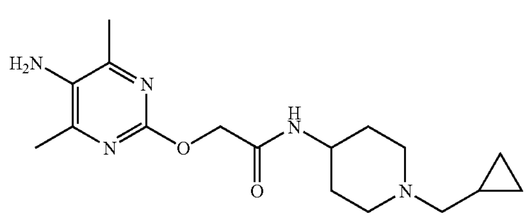 [SMILES: Cc1nc(OCC(=O)NC2CCN(CC3CC3)CC2)nc(C)c1N] | White amorphous (179-181° C.) |

TABLE 17-continued

| | | |
|---|---|---|
| 102 | [Chemical structure: 5-amino-4,6-dimethylpyrimidin-2-yloxy-acetamide-N-piperidinyl-(4-fluorobenzoyl)] | White amorphous |

| Compd. No. | MS(+) | 1H-NMR (CDCl₃) |
|---|---|---|
| 97 | 384(M + H) | 1.53-2.42 (6H, m), 2.23 (3H, s), 2.40 (3H, s), 2.75-3.05 (4H, m), 2.87 & 2.98 (3H, each s), 3.49 & 3.53 (2H, each s), 3.52-3.68 & 4.32-4.47 (1H, each m), 4.89 & 4.95 (2H, each s), 7.22-7.38 (5H, m) |
| 98 | 362(M + H) | 0.10 (2H, m), 0.52 (2H, m), 0.85 (1H, m), 1.20-2.12 (6H, m), 1.56 (3H, d), 2.18-2.37 (2H, m), 2.29 (6H, s), 2.84 & 3.03 (3H, each s), 3.05-3.23 (4H, m), 3.70-3.83 & 4.48 (1H, each m), 5.38 & 5.52 (1H, each q) |
| 99 | 398(M + H) | 1.48-2.13 (6H, m), 1.54 & 1.55 (3H, each d), 2.27 (6H, s), 2.84 & 3.03 (3H, each s), 2.88-3.08 (2H, m), 3.17 (2H, brs), 3.48 & 3.52 (2H, each s), 3.76 & 4.49 (1H, each m), 5.36 & 5.51 (1H, each q), 7.20-7.39 (5H, m) |
| 100 | 412(M + H) | 1.50-2.26 (6H, m), 1.54 & 1.55 (3H, each d), 2.35 (6H, s), 2.66 (3H, s), 2.82-3.09 (2H, m), 2.84 & 3.04 (3H, each s), 3.40-3.60 (2H, m), 3.75 & 4.50 (1H, each m), 5.37 & 5.53 (1H, each q), 7.19-7.40 (5H, m) |
| 101 | 334(M + H) | 0.06-0.12 (2H, m), 0.48-0.55 (2H, m), 0.86 (1H, m), 1.43-1.55 (2H, m), 1.88-1.97 (2H, m), 2.09 (2H, m), 2.23 (2H, d), 2.36 (6H, s), 2.95-3.04 (2H, m), 3.30 (2H, brs), 3.81-3.93 (1H, m), 4.79 (2H, s), 6.51 (1H, brd), |
| 102 | 402(M + H) | 1.29-1.55 (2H, m), 1.88-2.11 (2H, m), 2.37 (6H, s), 2.81-3.22 (2H, m), 3.32 (2H, brs), 3.62-3.87 (1H, m), 4.09-4.21 (1H, m), 4.53-4.72 (1H, m), 4.80 (2H, s), 6.62 (1H, brd), 7.10 (2H, m), 7.40 (2H, m) |

TABLE 18

| Compd. No. | Chemical Structure | Properties (mp) |
|---|---|---|
| 103 | [Chemical structure: 5-amino-4,6-dimethylpyrimidin-2-yloxy-acetyl-N-cyclopropyl-N-(1-benzylpiperidin-4-yl)] | White amorphous (137-140° C.) |
| 104 | [Chemical structure: 5-amino-4,6-diisopropylpyrimidin-2-yloxy-acetyl-N-methyl-N-(1-benzylpiperidin-4-yl)] | White amorphous |
| 105 | [Chemical structure: 5-amino-4,6-diisopropylpyrimidin-2-yloxy-acetyl-N-methyl-N-(1-cyclopropylmethylpiperidin-4-yl)] | White amorphous |

TABLE 18-continued

| | | |
|---|---|---|
| 106 | [structure] | Pale yellow amorphous |
| 107 | [structure] | White amorphous |
| 108 | [structure] | White amorphous (186-189° C.) |

| Compd. No. | MS(+) | 1H-NMR (CDCl₃) |
|---|---|---|
| 103 | 410(M + H) | 0.88-0.95 (4H, m), 1.68 (2H, m), 2.02 (4H, m), 2.30 (6H, s), 2.62 (1H, m), 2.91 (2H, m), 3.18 (2H, brs), 3.48 (2H, s), 4.10 (1H, m), 5.07 (2H, s), 7.20-7.35 (5H, m) |
| 104 | 440(M + H) | 1.23 (12H, d), 1.49-2.19 (6H, m), 2.80-3.05 (4H, m), 2.83 & 2.93 (3H, each s), 3.26 (2H, brs), 3.45-3.69 & 4.40-4.55 (1H, each m), 3.51 & 3.53 (2H, each s), 4.91 & 4.96 (2H, each s), 7.19-7.38 (5H, m) |
| 105 | 404(M + H) | 0.07-0.13 (2H, m), 0.50-0.60 (2H, m), 0.80-0.94 (1H, m), 1.24 (12H, d), 1.52-2.48 (8H, m), 2.83 & 2.95 (3H, each s), 2.98 (2H, m), 3.12-3.38 (4H, m), 3.58-3.70 & 4.47 (1H, each m), 4.92 & 4.97 (2H, each s) |
| 106 | 352(M + H) | 0.24-0.46 (2H, m), 0.64-0.82 (2H, m), 1.10-1.31 (1H, m), 1.40-1.84 (6H, m), 2.09 & 2.10 (3H, each s), 2.43-2.83 (2H, m), 2.98 & 3.02 (3H, each s), 3.36-3.78 & 4.60-4.76 (3H, m), 4.23 (2H, d), 6.05-6.15 & 6.28-6.37 (1H, each brs), 7.85 (1H, s) |
| 107 | 453(M + H) | 0.09-0.22 (2H, m), 0.52-0.62 (2H, m), 0.82-0.98 (1H, m), 1.60-2.39 (8H, m), 1.98 (3H, s), 2.89 & 2.92 (3H, each s), 3.18-3.28 (2H, m), 3.40-3.51 & 4.45-4.60 (1H, each m), 3.79 (3H, s), 4.11 & 4.16 (2H, each d), 4.51 (2H, d), 5.92-6.05 (1H, m), 6.80-6.90 (2H, m), 7.20-7.33 (2H, m), 7.57 & 7.59 (1H, each s) |
| 108 | 333(M + H) | 0.12 (2H, m), 0.54 (2H, m), 0.82-0.92 (1H, m), 1.60-2.18 (6H, m), 1.99 (3H, s), 2.27 & 2.30 (2H, each d), 2.92 & 2.93 (3H, each s), 3.19 (2H, m), 3.42-3.59 & 4.42-4.55 (1H, each m), 4.15 & 4.19 (2H, each d), 4.65-4.74 (2H, m), 5.82-5.97 (1H, m), 7.61 (1H, s) |

TABLE 19

| Compd. No. | Chemical Structure | Properties (mp) |
|---|---|---|
| 109 | [structure] | White amorphous (154-156° C.) |
| 110 | [structure] | White amorphous |

TABLE 19-continued

| Compd. No. | MS(+) | 1H-NMR (CDCl₃) |
|---|---|---|
| 109 | 388(M + H) | 1.50-2.23 (6H, m), 2.08 (3H, d), 2.90-3.13 (2H, m), 2.93 (3H, s), 3.46-3.62 & 4.48 (3H, m), 4.19 & 4.22 (2H, each d), 6.23 & 6.33 (1H, each brs), 7.21-7.38 (5H, m), 7.84 (1H, s) |
| 110 | 489(M + H) | 1.49-2.17 (6H, m), 1.98 (5H, s), 2.77-3.03 (2H, m), 2.86 & 2.90 (3H, each s), 3.40-3.54 & 4.40-4.53 (5H, m), 3.79 (3H, s), 4.02-4.19 (2H, m), 5.25 (1H, brs), 5.81 (1H, m), 6.75-6.90 (2H, m), 7.12-7.35 (7H, m), 7.63 (1H, m) |
| 111 | 369(M + H) | (CD₃OD) 1.58-2.00 (4H, m), 2.04 (3H, d), 2.20-2.33 (2H, m), 2.86 & 2.97 (3H, each s), 3.07 (2H, m), 3.62 & 3.65 (2H, each s), 3.72 & 4.30-4.45 (1H, each m), 4.33 & 4.41 (2H, each s), 6.25 (2H, s), 7.25-7.38 (5H, m), 7.46 (1H, d) |
| 112 | 417(M + H) | (CD₃OD) 1.72 (6H, s), 1.81-2.10 (4H, m), 2.16 (3H, s), 2.82 (3H, s), 3.00-3.18 (2H, m), 3.40-3.55 (2H, m), 4.26 (2H, brs), 4.93 (1H, m), 6.25 (2H, s), 7.48 (5H, brs), 8.27 (1H, d) |
| 113 | 384(M + H) | 1.53-2.20 (6H, m), 2.34 (6H, s), 2.90 & 2.91 (3H, each s), 2.98 (2H, m), 3.47-3.62 & 4.51 (1H, each m), 3.52 (2H, brs), 4.38 (2H, s), 4.75 (2H, brs), 7.23-7.37 (5H, m) |
| 114 | 374(M + H) | (DMSO) 1.39-1.85 (4H, m), 1.90-2.12 (2H, m), 2.72 & 2.85 (3H, each s), 2.87 (2H, m), 3.45 & 3.48 (2H, each s), 3.60 & 4.18 (1H, each m), 4.48 & 4.55 (2H, each s), 7.20-7.38 (5H, m), 7.40 (1H, brs), 7.62 (1H, brs), 7.78 & 7.80 (1H, each d) |

TABLE 20

| Compd. No | Chemical Structure | Properties (mp) |
|---|---|---|
| 115 | 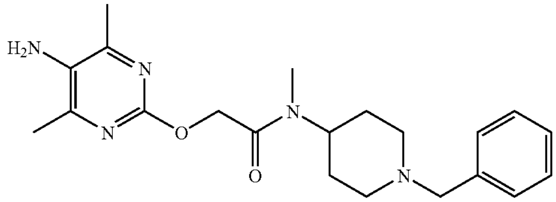 | White crystal (220-223° C.) |

TABLE 20-continued

| 116 | (structure: 5-amino-4,6-dimethylpyrimidin-2-yloxy-acetyl-N-methyl-N-(1-benzylpiperidin-4-yl)amide · HCl) | Pale yellow crystal (215-217° C.) |
| 117 | (structure: same free base · maleic acid) | White crystal (169-172° C.) |
| 118 | (structure: same free base · MeSO₃H) | White crystal (218-221° C.) |
| 119 | (structure: same free base · HNO₃) | White crystal (216-220° C.) |
| 120 | (structure: same free base · p-TsOH) | White crystal (190-193° C.) |

| Compd. No | MS(+) | 1H-NMR (CDCl₃) |
|---|---|---|
| 115 | 384(M + H) | (DMSO) 1.53-2.27 (4H, m), 2.21 (6H, s), 2.67 & 2.85 (3H, each s), 3.10 (2H, m), 3.25-3.53 (2H, m), 3.94 & 4.49 (3H, m), 4.30 (2H, s), 4.82 & 4.92 (2H, each s), 7.41-7.66 (5H, m), 9.29-9.80 (1H, m) |
| 116 | 384(M + H) | (DMSO) 1.55-1.92 (2H, m), 2.12-2.40 (2H, m), 2.21 (6H, s), 2.68 & 2.86 (3H, each s), 2.97-3.11 (2H, m), 3.26-3.48 (2H, m), 3.95 & 4.40-4.60 (3H, m), 4.25 (2H, m), 4.81 & 4.91 (2H, each s), 7.41-7.71 (5H, m), 10.76-11.01 (1H, m) |
| 117 | 384(M + H) | (DMSO) 1.55-2.08 (4H, m), 2.21 (6H, s), 2.67 & 2.84 (3H, each s), 3.02 (2H, m), 3.31 (2H, m), 3.90 & 4.30-4.62 (3H, m), 4.21 (2H, brs), 4.82 & 4.92 (2H, each s), 6.04 (2H, s), 7.47 (5H, brs) |

TABLE 20-continued

| | | |
|---|---|---|
| 118 | 384(M + H) | (DMSO) 1.61-2.10 (4H, m), 2.21 (6H, s), 2.31 (3H, s), 2.67 & 2.84 (3H, each s), 3.02-3.18 (2H, m), 3.26-3.51 (2H, m), 3.95 & 4.41 (1H, each m), 4.29 (2H, m), 4.49 (2H, brs), 4.82 & 4.92 (2H, each s), 7.49 (5H, m), 9.15-9.40 (1H, m) |
| 119 | 384(M + H) | (DMSO) 1.62-2.09 (4H, m), 2.20 (6H, s), 2.66 & 2.84 (3H, each s), 3.02-3.19 (2H, m), 3.28-3.52 (2H, m), 3.95 & 4.42 (1H, each m), 4.30 (2H, m), 4.52 (2H, brs), 4.82 & 4.93 (2H, each s), 7.42-7.63 (5H, m), 9.12-9.79 (1H, m) |
| 120 | 384(M + H) | (DMSO) 1.63-2.11 (4H, m), 2.21 (6H, s), 2.29 (3H, s), 2.66 & 2.84 (3H, each s), 3.02-3.18 (2H, m), 3.26-3.51 (2H, m), 3.95 & 4.36-4.58 (1H, each m), 4.29 (2H, m), 4.49 (2H, brs), 4.82 & 4.92 (2H, each s), 7.11 (2H, d), 7.45-7.62 (7H, m), 9.12-9.76 (1H, m) |

TABLE 21

| Compd. No | Chemical Structure | Properties (mp) |
|---|---|---|
| 121 | [Structure: 5-amino-4,6-dimethylpyrimidin-2-yloxy-acetyl-N-methyl-N-(1-benzylpiperidin-4-yl)amide, EtSO₃H salt] | White crystal (231-234° C.) |
| 122 | [Structure: 5-amino-4,6-dimethylpyrimidin-2-yloxy-acetyl-N-methyl-N-(1-benzylpiperidin-4-yl)amide, benzenesulfonic acid salt] | White crystal (226-228° C.) |
| 123 | [Structure: 3-methyl-5-nitro-2-(N-methylaminoacetyl)pyridine derivative with N-methyl-N-(1-benzylpiperidin-4-yl)amide] | Pale yellow amorphous (59-63° C.) |
| 124 | [Structure: 5-amino-3-methylpyridin-2-yloxy-acetyl-N-methyl-N-(1-benzylpiperidin-4-yl)amide, HCl salt] | Pale yellow crystal (Hydrochloride) (Water/isopropanol) (190-193° C.) |
| 125 | [Structure: 5-chloropyridin-3-yloxy-acetyl-N-methyl-N-(1-benzylpiperidin-4-yl)amide, HCl salt] | White solid (185-188° C.) |

TABLE 21-continued

| 126 | 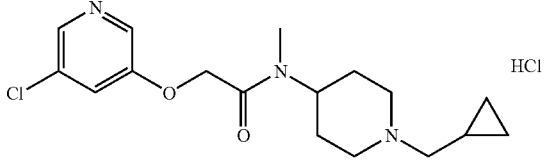 [SMILES: CN(C(=O)COc1cncc(Cl)c1)C1CCN(CC2CC2)CC1 ; Cl] | White solid |

| Compd. No | MS(+) | 1H-NMR (CDCl₃) |
|---|---|---|
| 121 | 384(M + H) | (DMSO) 1.07 (3H, t), 1.61-2.15 (4H, m), 2.20 (6H, s), 2.40 (2H, q), 2.67 & 2.85 (3H, each s), 3.01-3.18 (2H, m), 3.29-3.52 (2H, m), 3.95 & 4.42 (1H, each m), 4.29 (2H, m), 4.50 (2H, brs), 4.82 & 4.93 (2H, each s), 7.49 (5H, m), 9.26-9.79 (1H, m) |
| 122 | 384(M + H) | (DMSO) 1.60-2.11 (4H, m), 2.21 (6H, s), 2.66 & 2.83 (3H, each s), 3.01-3.19 (2H, m), 3.28-3.51 (2H, m), 3.94 & 4.42 (1H, each m), 4.30 (2H, m), 4.50 (2H, brs), 4.82 & 4.93 (2H, each s), 7.27-7.37 (3H, m), 7.49 (5H, brs), 7.57-7.65 (2H, m), 9.15-9.76 (1H, m) |
| 123 | 398(M + H) | 1.52-2.20 (6H, m), 2.24 (3H, s), 2.90-3.07 (2H, m), 2.94 & 2.95 (3H, each s), 3.49-3.62 & 4.49 (1H, each m), 3.52 & 3.56 (2H, each s), 4.27 & 4.30 (2H, each d), 6.40 & 6.48 (1H, each brs), 7.22-7.41 (5H, m), 8.03 (1H, brs), 8.94 & 8.96 (1H, each d) |
| 124 | 369(M + H) | (DMSO) 1.55-1.90 (2H, m), 2.01-2.36 (2H, m), 2.07 (3H, s), 2.67 & 2.83 (3H, each s), 2.99 (2H, m), 3.21-3.44 (2H, m), 3.90-4.02 & 4.43 (1H, each m), 4.22 (2H, m), 4.67-5.18 (2H, brs), 4.88 & 4.94 (2H, each s), 6.87 (1H, s), 7.25 (1H, s), 7.38-7.50 (3H, m), 7.53-7.69 (2H, m) |
| 125 | 374(M + H) | (CD₃OD) 1.85-2.20 (4H, m), 2.86 & 2.95 (3H, each s), 3.12 (2H, m), 3.46-3.60 (2H, m), 3.98 & 4.52 (1H, each m), 4.29 (2H, brs), 4.97 & 5.05 (2H, each s), 7.50 (6H, m), 8.16 (1H, m), 8.21 (1H, m) |
| 126 | 338(M + H) | (CD₃OD) 0.26-0.35 (2H, m), 0.64-0.73 (2H, m), 1.03 (1H, m), 1.78-2.12 (4H, m), 2.56-2.78 (4H, m), 2.89 & 2.97 (3H, each s), 3.40-3.55 (2H, m), 3.82 & 4.48 (1H, each m), 4.98 & 5.03 (2H, each s), 7.51-7.58 (1H, m), 8.15-8.20 (1H, m), 8.22-8.26 (1H, m) |

TABLE 22

| Compd. No. | Chemical Structure | Properties (mp) |
|---|---|---|
| 127 | 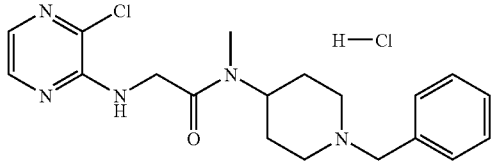 | White amorphous (78-83° C.) |
| 128 | 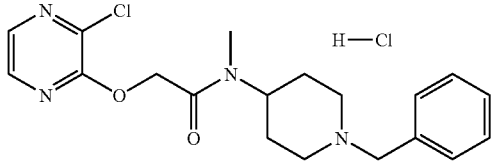 | White solid (85-86° C.) |
| 129 | 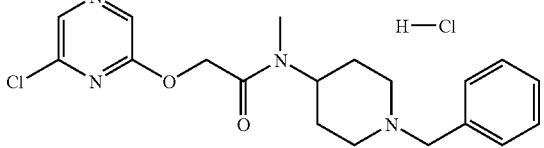 | White solid (90-91° C.) |

TABLE 22-continued

| | | | |
|---|---|---|---|
| 130 | (structure) | H—Cl | White solid (79-81° C.) |
| 131 | (structure) | H—Cl | White solid (96-98° C.) |
| 132 | (structure) | CO₂H / CO₂H | White solid |

| Compd. No. | MS(⁺) | 1H-NMR (CDCl₃) |
|---|---|---|
| 127 | 374(M + H) | (CD$_3$OD) 1.79-2.10 (4H, m), 2.68-2.98 (5H, m), 3.20-3.40 (2H, m), 3.90-4.49 (5H, m), 7.38-7.57 (6H, m), 7.92-7.94 (1H, m) |
| 128 | 375(M + H) | (CD$_3$OD) 1.81-2.12 (4H, m), 2.83-2.98 (5H, m), 3.34-3.47 (2H, m), 3.90-3.93 & 4.40-4.44 (1H, each m), 4.08-4.15 (2H, m), 5.20 & 5.27 (2H, each s), 7.46-7.63 (5H, m), 7.97-8.03 (2H, m) |
| 129 | 375(M + H) | (CD$_3$OD) 1.83-2.13 (4H, m), 2.85-3.00 (5H, m), 3.44-3.47 (2H, m), 3.92-3.98 & 4.45-4.53 (1H, each m), 4.15 & 4.19 (2H, each s), 5.13 & 5.22 (2H, each s), 7.45-7.50 (5H, m), 8.22 (1H, s), 8.28 (1H, s) |
| 130 | 370(M + H) | (CD$_3$OD) 1.84-2.10 (4H, m), 2.85-3.03 (8H, m), 3.46-3.49 (2H, m), 3.95-4.00 & 4.48-4.58 (1H, each m), 4.18 & 4.22 (2H, each s), 5.08 & 5.17 (2H, each s), 7.14 (1H, d), 7.48-7.49 (6H, m) |
| 131 | 370(M + H) | (CD$_3$OD) 1.87-2.14 (4H, m), 2.83-3.00 (6H, m), 3.12-3.20 (2H, m), 3.54-3.58 (2H, m), 4.05-4.12 & 4.48-4.55 (1H, each m), 4.32 & 4.34 (2H, each s), 5.05 & 5.14 (2H, each s), 7.34 (1H, s), 7.39 (1H, s), 7.50-7.53 (5H, m) |
| 132 | 384(M + H) | (CD$_3$OD) 1.77-2.10 (4H, m), 2.69-2.98 (5H, m), 3.11 (6H, s), 3.29-3.41 (2H, m), 3.85-3.90 & 4.40-4.47 (1H, each m), 3.96 & 4.06 (2H, each s), 5.10 & 5.19 (2H, each s), 6.70 (2H, s), 7.32 (1H, d,), 7.43-7.49 (5H, m), 7.62 (1H, d) |

TABLE 23

| Compd. No | Chemical Structure | Properties (mp) |
|---|---|---|
| 133 | (structure) H—Cl | White solid |
| 134 | (structure) H—Cl | White solid (97-98° C.) |

TABLE 23-continued

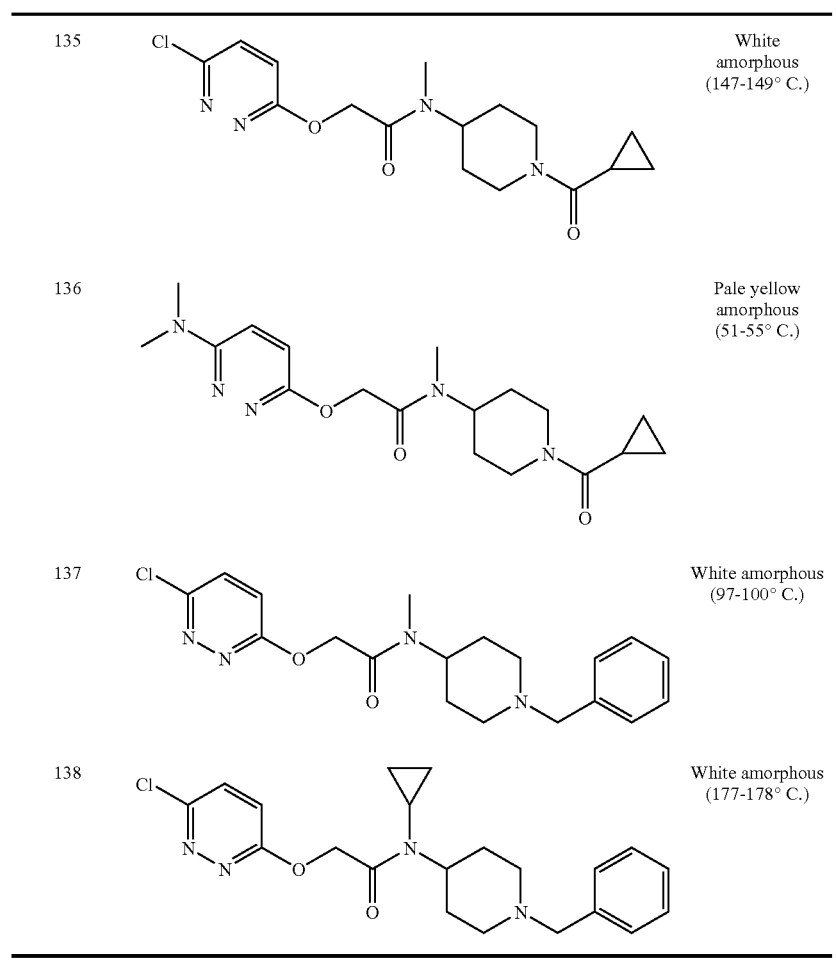

| | | | |
|---|---|---|---|
| 135 | | | White amorphous (147-149° C.) |
| 136 | | | Pale yellow amorphous (51-55° C.) |
| 137 | | | White amorphous (97-100° C.) |
| 138 | | | White amorphous (177-178° C.) |

| Compd. No | MS(+) | 1H-NMR (CDCl$_3$) |
|---|---|---|
| 133 | 384(M + H) | (CD$_3$OD) 1.85-2.16 (4H, m), 2.82-2.97 (3H, m), 3.09-3.18 (8H, m), 3.55-3.62 (2H, m), 4.05-4.15 & 4.49-4.60 (1H, each m), 4.23-4.38 (2H, m), 5.13 & 5.23 (2H, each s), 7.49-7.63 (7H, m) |
| 134 | 356(M + H) | (CD$_3$OD) 1.92-2.21 (4H, m), 2.86 & 2.98 (3H, each s), 3.12-3.25 (2H, m), 3.54-3.57 (2H, m), 4.02-4.12 & 4.51-4.59 (1H, each m), 4.31 (2H, s), 5.10 & 5.20 (2H, each s), 7.24 (1H, d), 7.44 (1H, d), 7.50-7.52 (5H, m) |
| 135 | 353(M + H) | 0.71-0.84 (2H, m), 0.92-1.05 (2H, m), 1.50-2.00 (5H, m), 2.62 (1H, m), 2.85 & 2.90 (3H, each s), 3.16 (1H, m), 3.68-3.81 & 4.67 (1H, each m), 4.25-4.42 (1H, m), 4.62-4.85 (1H, m), 5.14 & 5.23 (2H, each s), 7.16 (1H, d), 7.42 (1H, d) |
| 136 | 362(M + H) | 0.72-0.83 (2H, m), 0.93-1.03 (2H, m), 1.51-1.89 (5H, m), 2.50-2.69 (1H, m), 2.86 (3H, s), 3.07-3.25 (1H, m), 3.10 & 3.11 (6H, each s), 3.68-3.80 & 4.66-4.82 (2H, m), 4.24-4.40 (1H, m), 5.03-5.21 (2H, m), 6.94 (1H, d), 7.02 (1H, d) |
| 137 | 375(M + H) | 1.55-1.82 (4H, m), 1.89-2.12 (2H, m), 2.85-3.06 (2H, m), 2.87 & 2.91 (3H, each s), 3.44 & 4.43 (1H, each m), 3.49 & 3.53 (2H, each s), 5.17 & 5.22 (2H, each s), 7.14 (1H, d), 7.21-7.38 (5H, m), 7.40 (1H, d) |
| 138 | 401(M + H) | 0.95 (4H, m), 1.71 (2H, m), 2.03 (4H, m), 2.63 (1H, m), 2.92 (2H, m), 3.49 (2H, s), 4.04 (1H, m), 5.34 (2H, s), 7.12 (1H, d,), 7.21-7.35 (5H, m), 7.39 (1H, d) |

TABLE 24

| Compd. No | Chemical Structure | Properties (mp) |
|---|---|---|
| 139 | 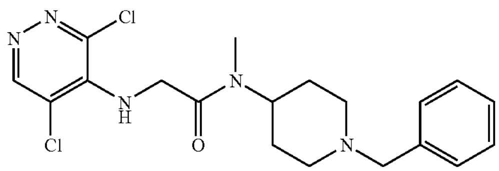 [SMILES: CN(C(=O)CNc1c(Cl)cnnc1Cl)C1CCN(Cc2ccccc2)CC1] | White amorphous |
| 140 | 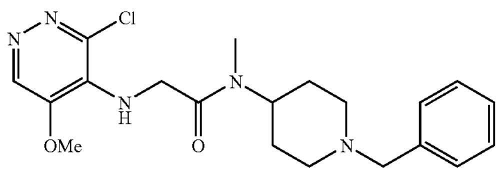 [SMILES: COc1cnnc(Cl)c1NCC(=O)N(C)C1CCN(Cc2ccccc2)CC1] | White amorphous |
| 141 | 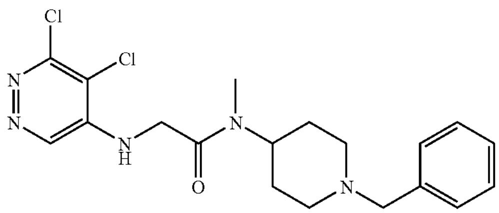 [SMILES: CN(C(=O)CNc1cnnc(Cl)c1Cl)C1CCN(Cc2ccccc2)CC1] | White amorphous (179-183° C.) |

| Compd. No | MS(+) | 1H-NMR (CDCl$_3$) |
|---|---|---|
| 139 | 408(M + H) | 1.54-2.18 (6H, m), 2.88 & 2.95 (3H, each s), 2.92-3.06 (2H, m), 3.34 & 4.45-4.55 (1H, each m), 3.51 & 3.54 (2H, each s), 4.47 & 4.50 (2H, each d), 6.80-6.90 (1H, m), 7.22-7.38 (5H, m), 8.63 & 8.64 (1H, each s) |
| 140 | 404(M + H) | 1.56-2.18 (6H, m), 2.87 & 2.93 (3H, each s), 2.91-3.08 (2H, m), 3.35 & 4.43-4.55 (1H, each m), 3.52 (2H, m), 4.13 & 4.14 (3H, each s), 4.42 & 4.47 (2H, each d), 6.26-6.34 (1H, m), 7.22-7.39 (5H, m), 8.41 & 8.42 (1H, each s) |
| 141 | 408(M + H) | 1.55-2.18 (6H, m), 2.93 & 2.97 (3H, each s), 2.95-3.09 (2H, m), 3.38 & 4.50 (1H, each m), 3.52 & 3.57 (2H, each s), 4.01 & 4.05 (2H, each d), 6.46-6.56 (1H, m), 7.25-7.38 (5H, m), 8.47 & 8.48 (1H, each s) |

The nitrogen-containing six-membered aromatic ring derivatives of the present invention represented by the formula (I) were evaluated for different activities in the following tests 1 to 7:

Test 1: Ability to promote axonal outgrowth
Test 2: Ability to promote angiogenesis
Test 3: Ability to promote the neurite outgrowth of spinal cord neurons
Test 4: Evaluation of angiogenesis in an ischemic lower limb model in mice (critical limb ischemia)
Test 5: Ability to improve cardiac functions in a myocardial infarction model in rats
Test 6: Ability to improve functions in a rat microsphere (micro-embolism) model
Test 7: Ability to improve functions in a spinal cord injury model in rats Specific methods for evaluation are described below.

Test Example 1

Ability to Promote Axonal Outgrowth

According to the method of M. P. Mattson [M. P. Mattson, Brain Res. Rev., 13, 179, (1988)], the hippocampal region was isolated from 18-day embryos of female Wistar rats and the neurons were dispersed using the papain dissociation system. Hippocampal neuron were suspended in 5% Nu-serum+B27 supplement+Neurobasal medium at $5 \times 10^4$ cells/well/2 mL. 2 mL of the cell suspension were inoculated on a poly-D-lysine-coated 36φ dish and the neuron were incubated at 37° C. in a 5% $CO_2$ incubator.

On day 3 of the incubation period, 1 mL of the culture medium was replaced with 1 mL of 5% Nu-serum+B27 supplement+Neurobasal medium containing 2 mM AraC. Each test compound was added to the culture on day 3 and day 7 of the incubation period. On day 9, cells were fixed in a 4% paraformaldehyde solution. The nerve axons of the fixed cells were stained with the Rabbit anti-growth-associated protein-43 polyclonal antibody and the stained cells were quantified using Kurabo neuron outgrowth-quantication software.

The ability (%) of each test compound to promote axonal outgrowth was calculated from the following equation:

The ability to promote axonal outgrowth (%)= [(measurement with a compound of interest)/ (measurement of control)]×100

Example Compounds shown in Table 25 were used as test compounds and were each added at concentrations of 3 μM and 0.3 μM.

The results are shown in Table 25. Although the measurements shown in Table 25 are mostly shown for the concentration of 3 μM, the measurements obtained for the concentration of 0.3 μM are shown for compounds that gave 120 (a value indicating a significant effect) or a higher measurement only at the concentration of 0.3 μM or compounds that gave a significantly higher measurement at 0.3 μM than at 3 μM.

Since bFGF gives a measurement of about 120 in this test, 120 is used as the threshold to determine whether a given compound has the ability to promote axonal outgrowth

TABLE 25

| Compound No. | Promotion of axonal outgrowth (%)<br>(Compound Conc. = 3 μM) |
|---|---|
| 63 | 186 |
| 64 | 120 (Compound Conc. = 0.3 μM) |
| 65 | 134 |
| 69 | 172 (Compound Conc. = 0.3 μM) |
| 71 | 140 |
| 72 | 141 |
| 73 | 131 |
| 74 | 159 |
| 75 | 125 |
| 76 | 123 |
| 77 | 135 |
| 78 | 130 |
| 79 | 123 |
| 80 | 129 |
| 81 | 115 |
| 82 | 154 |
| 85 | 140 |
| 88 | 142 (Compound Conc. = 0.3 μM) |
| 91 | 150 |
| 92 | 127 |
| 93 | 143 |
| 94 | 122 |
| 95 | 201 |
| 97 | 127 |
| 98 | 130 |
| 100 | 128 |
| 101 | 193 |
| 102 | 233 |
| 104 | 134 (Compound Conc. = 0.3 μM) |
| 108 | 122 |
| 109 | 159 |
| 111 | 118 (Compound Conc. = 0.3 μM) |
| 112 | 126 |
| 113 | 144 |
| 114 | 183 |
| 123 | 131 |
| 125 | 173 (Compound Conc. = 0.3 μM) |
| 126 | 167 |
| 128 | 156 |
| 129 | 147 |
| 130 | 143 |
| 135 | 131 |
| 136 | 133 |
| 138 | 151 |
| 139 | 143 |
| 140 | 128 (Compound Conc. = 0.3 μM) |

As can be seen from Table 25, each of Example Compounds of the present invention showed about 120 (a value indicating a significant effect) or a higher measurement, indicating a significant ability to promote axonal outgrowth.

Test Example 2

Ability to Promote Angiogenesis

Using an angiogenesis test kit containing a mixture of human vascular endothelial cells and fibroblasts [KZ-1000; Kurabo], the ability of test compounds to promote angiogenesis was evaluated. Each test compound was added on days 1, 4, and 7 of the incubation period. On day 9, cells were immunostained with CD31 and photographed. Control cells were cultured under the same conditions, only without the addition of a test compound, and photographed.

The lumen length of the blood vessel was quantified from the obtained images using an angiogenesis-quantification software. The ability (%) of each test compound to promote angiogenesis was calculated from the following equation:

The ability to promote angiogenesis (%)=
[(measurement with a compound of interest)/
(measurement of control)]×100

Example Compounds shown in Table 26 were used as test compounds.

The results are shown in Table 26. Although the measurements shown in Table 26 are mostly shown for the concentration of 3 μM, the measurements obtained for the concentration of 0.3 μM are shown for compounds that gave 120 (a value indicating a significant effect) or a higher measurement only at the concentration of 0.3 μM or compounds that gave a significantly higher measurement at 0.3 μM than at 3 μM.

Since bFGF gives a measurement of about 120 in this test, 120 is used as the threshold to determine whether a given compound has the ability to promote angiogenesis.

TABLE 26

| Compound No. | Promotion of angiogenesis (%)<br>(Compound Conc. = 3 μM) |
|---|---|
| 64 | 177 |
| 65 | 170 |
| 69 | 161 (Compound Conc. = 0.3 μM) |
| 71 | 126 |
| 72 | 142 |
| 73 | 139 |
| 74 | 136 |
| 75 | 150 |
| 76 | 149 |
| 77 | 149 |
| 78 | 144 |
| 79 | 133 |
| 80 | 116 (Compound Conc. = 0.3 μM) |
| 81 | 126 |
| 82 | 130 |
| 85 | 123 |
| 88 | 122 |
| 91 | 124 |
| 92 | 153 |
| 93 | 138 |
| 95 | 133 |
| 97 | 134 |
| 98 | 129 (Compound Conc. = 0.3 μM) |
| 100 | 116 (Compound Conc. = 0.3 μM) |
| 108 | 114 (Compound Conc. = 0.3 μM) |
| 109 | 124 |
| 111 | 121 |
| 114 | 125 |
| 123 | 132 |
| 128 | 115 (Compound Conc. = 0.3 μM) |
| 130 | 118 (Compound Conc. = 0.3 μM) |
| 135 | 140 |
| 136 | 110 (Compound Conc. = 0.3 μM) |

As can be seen from Table 26, each of Example Compounds of the present invention showed about 120 (a value indicating a significant effect) or a higher measurement, indicating a significant ability to promote angiogenesis.

Test Example 3

Ability to Promote the Neurite Outgrowth of Spinal Cord Neurons

According to the method of Martin G. Hanson Jr. [J. Neurosci., 1998 Sep. 15; 18(18): 7361-71], the spinal cord region was isolated from 15-day embryos of female Wistar rats and the cells were dispersed using the papain dissociation system. Neurons were collected using 6.8% Metrizamide density gradient and were suspended in 2% FBS+Leibovitz's −15 medium so that the density of the cells will be $2\times10^3$ cells/well/200 µL. 200 µL of the cell suspension was inoculated on a poly-D-lysine/laminin-coated 96 well plate and the plate was incubated in an incubator at 37° C. Test compounds were added 1 hour after seeding of cells.

On day 3 of the incubation period, neurons were stained with Calcein-AM and the lengths of neurites were determined using IN Cell Analyzer (GE Healthcare Bioscience).

The ability (%) of each test compound to promote neurite outgrowth was calculated from the following equation:

The ability to promote neurite outgrowth (%)=
[(measurement with a compound of interest)/
(measurement of control)]×100

Example Compounds 65, 71, 74, 92, 130 and 135 were used as test compounds and were each added at a concentration of 0.1 µM.

The results are shown in Table 27. bFGF gives a measurement of about 130 in this test. In Table 18, a value of 120 is used as the threshold to indicate that a given compound exhibits a significant effect.

TABLE 27

| Compound No. | Promotion of spinal cord neurite outgrowth (%) (Compound Conc. = 0.1 µM) |
|---|---|
| 65 | 135 |
| 71 | 139 |
| 74 | 125 |
| 92 | 120 |
| 130 | 128 |
| 135 | 121 |

As can be seen from Table 27, each of Example Compounds of the present invention showed about 120 (a value indicating a significant effect) or a higher measurement, indicating a significant ability to promote the neurite outgrowth of spinal cord neurons.

Test Example 4

Evaluation of Angiogenesis in a Lower Limb Ischemia (Critical Limb Ischemia) Model in Mice
(In Vivo Test)

According to the method of Ichiro Masaki [Circ Res. 90; 966-973 (2002)], the left femoral artery of Balb/c mice was excised to establish a model of critical limb ischemia (n=29 to 30).

Test compounds used were Example Compounds 65, 92, 114, 130, 135 and 136, each of which was orally administered once daily at a dose of 0.1 mg/kg or 1.0 mg/kg for 10 days starting from the day of femoral artery excision. Once necrosis was observed in the lower limb of an animal, the observation of the individual was stopped and the survival rate of lower limb was monitored with time.

The results are shown in FIGS. 1 to 6 in which FIGS. 1, 2, 3, 4, 5 and 6 show the results of Example Compounds 65, 92, 114, 130, 135 and 136, respectively.

In the figures, a thick solid line indicates a Vehicle group, a thin dotted line indicates a group administered 0.1 mg/kg/day of each compound, and a thin solid line indicates a group administered 1.0 mg/kg/day of each compound.
*: $P<0.05$, : $P<0.01$, *: $P<0.001$ vs Vehicle by Wilcoxon's test.

The results indicate that each of Example Compounds 65, 92, 114, 130, 135 and 136 of the present invention resulted in an increased survival rate of the femoral artery/vein in lower limb and is therefore highly effective in ameliorating critical limb ischemia.

Test Example 5

Ability to Improve Cardiac Functions in a Myocardial Infarction Model in Rats

According to the method of Masakatsu Wakeno et al. [Circulation 114: 1923-1932 (2006)], 10-week-old male Slc:SD rats were anesthetized with pentobarbital and cut open in the chest area. The left anterior descending coronary artery (LAD) was completely occluded to establish a myocardial infarction model. Sham group underwent only thoracic surgical procedure.

The test compound used was Example Compound 65, which was orally administered once daily at a dose of 0.01 mg/kg, 0.1 mg/kg or 1.0 mg/kg for 28 days starting from the day of establishment of myocardial infarction model (after awakening from anesthesia).

4 weeks after establishing myocardial infarction, animals were anesthetized with pentobarbital and monitored for their cardiachemodynamics using a mirror catheter. Subsequently, blood samples were collected from the abdominal aorta, wet lung weight was measured, and plasma BNP levels after arterial blood sampling were measured (RIA).

The results are shown in FIGS. 7 to 10.
FIGS. 7, 8, 9 and 10 show the results of LVEDP, LVdP/dt max, lung weight and plasma BMP levels, respectively.
: $P<0.05$, ##: $P<0.01$ between sham and control by Student's t-test
*: $P<0.05$, **: $P<0.01$: vs control by Dunnett's test Example Compound 65 suppressed the decrease in the maximum left ventricular contraction and the diastolic velocity following myocardial infarction, the increase in the end-diastolic pressure, and the increase in the wet lung weight, an indication of pulmonary congestion. The compound also suppressed the increase in the plasma BNP levels. These results demonstrate that Example Compound 65 of the present invention is highly effective in improving the decreased cardiac functions and heart failure associated with myocardial infarction.

Test Example 6

Ability to Improve Functions in a Rat Microsphere (Micro-Embolism) Model

According to the method of Ichiro Date et al. [Journal of Neuroscience Research 78; 442-453 (2004)], 8-week-old male Crl:CD(SD) rats were used. Animals were anesthetized with halothane and midline incision was made. Right carotid artery was separated and a thread was looped around the common carotid artery and external carotid artery. The pterygopalatine artery was temporarily clipped with an aneurysm clip. The blood flow through the common carotid artery and external carotid artery was temporarily interrupted and 0.1 mL of a microsphere suspension composed of microspheres dispersed in a 30% sucrose solution (1800 microspheres/0.1 mL) was injected into the common carotid artery. After injection of the suspension, the puncture of the injection needle was filled with instant glue while the blood flow was interrupted. The blood flow was then restored and the surgical wound was sutured. Neurological symptoms were observed the day following the surgery. The animals were assigned to each treated group at random with respect to the measurements of neurological symptoms, the decrease in body weight from the previous day, and the body weight on that day.

The test compounds used were Example Compound 65, 108, 130, 135 and 137, each of which was administered at a dose of 1.0 mg/kg. Example Compound 65 was administered also at a dose of 0.1 mg/kg. Each compound was orally administered once daily for 10 days starting from the following day of the surgery. Coordinated motor functions were measured 5 times on an accelerated rota-rod (4 to 40 rpm/5 min) 2 weeks after the surgery.

As a standard parameter, the total time of the 5 measurements on rota-rod was summarized in FIGS. 11 to 15.

Specifically, FIGS. 11 to 15 show the effect of different compounds 2 weeks after the microsphere injection (rota-rod test standard parameter). The figures show the results of rota-rod tests 2 weeks after the ischemic event in which each compound was orally administered at 1.0 mg/kg once daily for 10 days (Example Compound 65 was administered at 0.1 mg/kg or 1.0 mg/kg). What is shown in the figures is the total time of the 5 measurements on rota-rod as a standard parameter.

FIGS. 11, 12, 13, 14 and 15 show the results of Example Compounds 65, 108, 130, 135 and 137, respectively.

***: $p<0.0001$, Dunnett's multiple range test vs. Vehicle.

These results indicate that each of Example Compounds 65, 108, 130, 135 and 137 of the present invention is highly effective in ameliorating ischemic cerebral infarction and after-effects thereof.

According to an article by Kraft et al. (Eur. J. Neurosci. 2005 June; 21(11): 3117-32), the experiment for Test Example 6 using microspheres to treat cerebral infarction caused by embolism serves as a suitable model for microvascular disorders, a sign of cognitive disorder. Thus, the results of Test Example 6 may indicate that the compounds of the present invention are effective in ameliorating dementia.

Test Example 7

Ability to Improve Functions in a Spinal Cord Injury (SCI) Model in Rats

According to the method of Venkata Ramesh Dasari et al. [J Neurotrauma. 2007 February; 24(2):391-410], 9-week-old female Slc: SD rats were used. Animals were anesthetized with pentobarbital and incised along the dorsal midline. After the spinal column was exposed by dorsal midline incision, the 9th thoracic vertebral arch was removed with bone scissors, paying attention not to damage the dura mater. The upper and lower bones were held in place to position the exposed spinal site just under the impactor device (where impact is applied) and then a 200-kdyn force was applied to the site. Tonic extension of the lower limbs by the spinal cord injury was checked.

The test compound used was Example Compound 65, which was administered at a dose of 1 mg/kg. Specifically, the compound was administered through the tail vein once daily for 10 days, starting from 90 min after the surgery. The motor function of lower limb was evaluated by BBB score (Basso D M, Beattie M S, Bresnahan J C: J Neurotrauma. 1995; 12:1-21) once a week until 5 weeks after surgery. The results are shown in FIG. 16.

The results indicate that Example Compound 65 of the present invention is highly effective in ameliorating spinal cord injury.

Industrial Applicability

The compounds of the present invention have the ability to promote axonal outgrowth in combination with the ability to promote angiogenesis and are therefore effective in reducing or treating central nervous system such as head trauma and spinal cord injury, cerebral infarction, ischemic heart diseases such as myocardial infarction and organic angina, peripheral arterial occlusive diseases such as critical limb ischemia or after-effects of these diseases, or other diseases against which the compounds of the present invention are considered effective. The present invention, therefore, is of significant medical importance.

Figure 1:
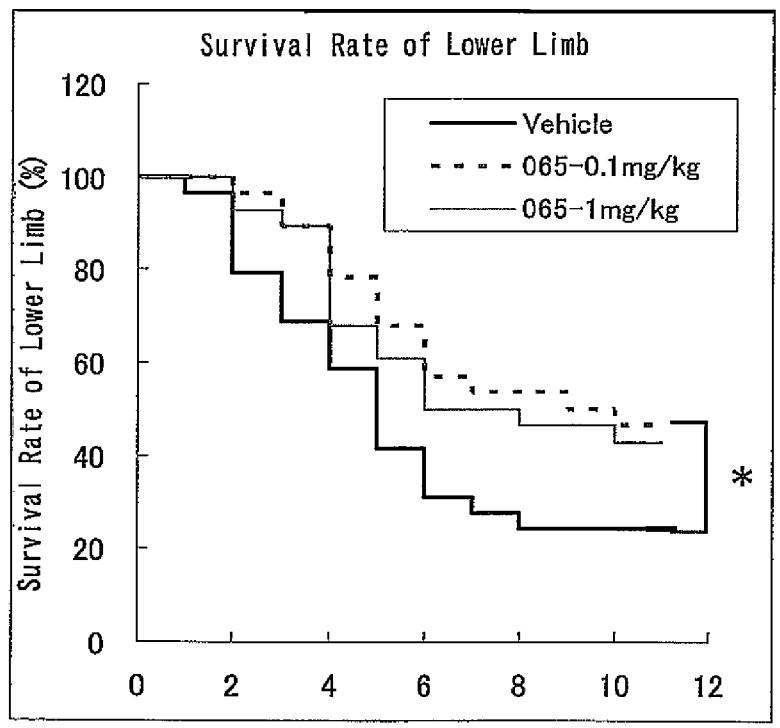
FIG. 1 is a diagram showing the results of Example Compound 65 in Test Example 4.
Figure 2:
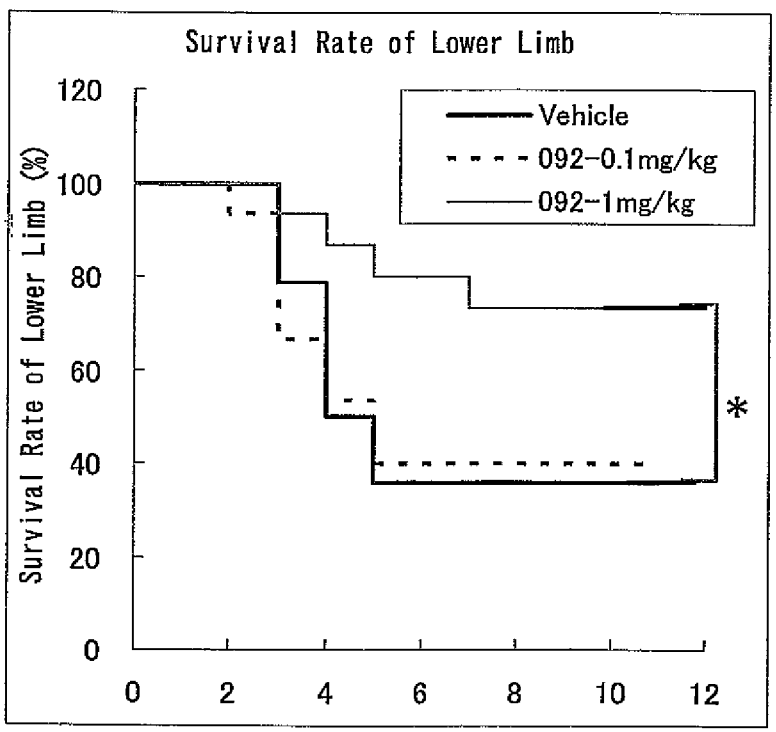
FIG. 2 is a diagram showing the results of Example Compound 92 in Test Example 4.
Figure 3:
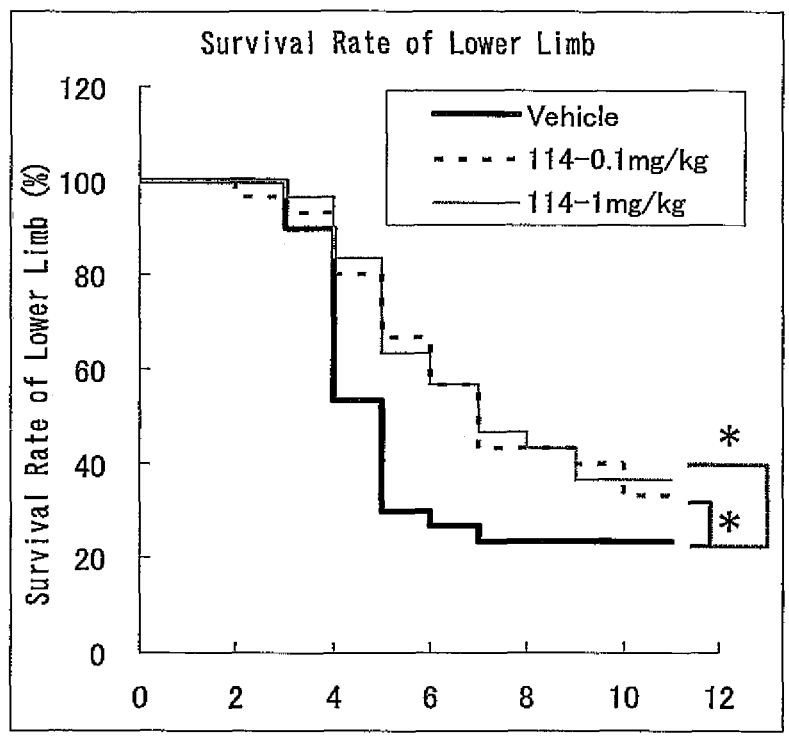
FIG. 3 is a diagram showing the results of Example Compound 114 in Test Example 4.
Figure 4:
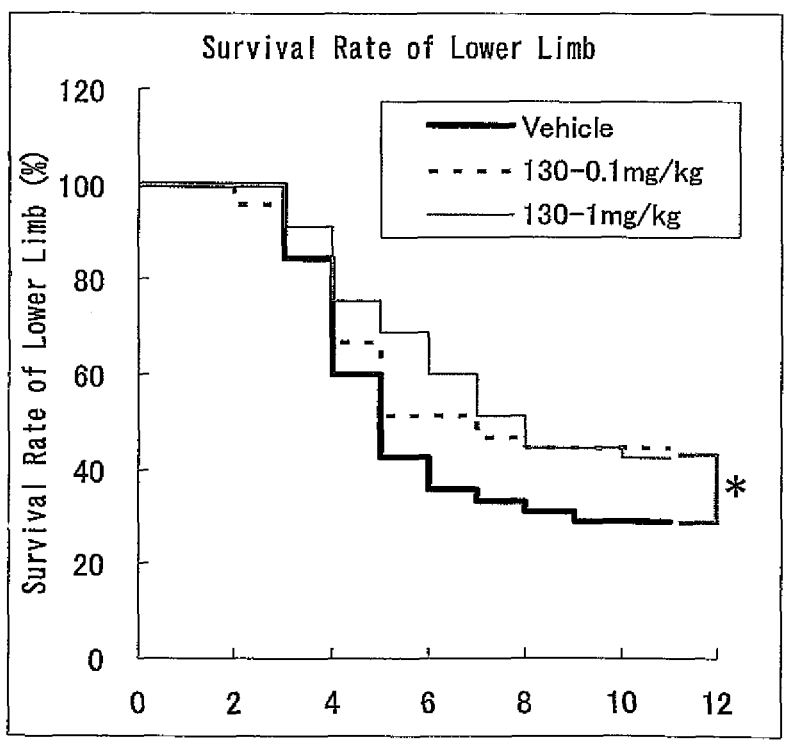
FIG. 4 is a diagram showing the results of Example Compound 130 in Test Example 4.
Figure 5:
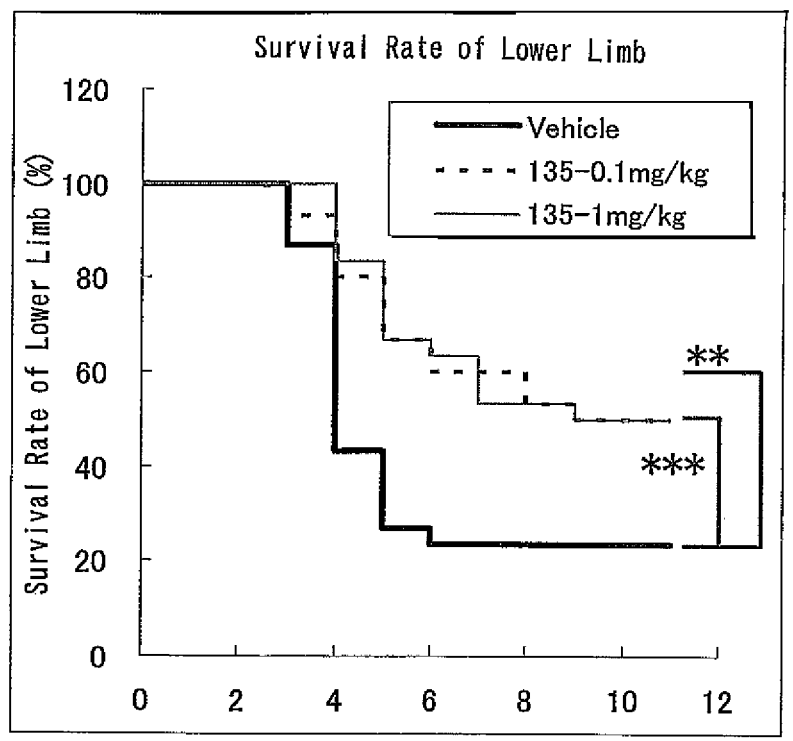
FIG. 5 is a diagram showing the results of Example Compound 135 in Test Example 4.
Figure 6:
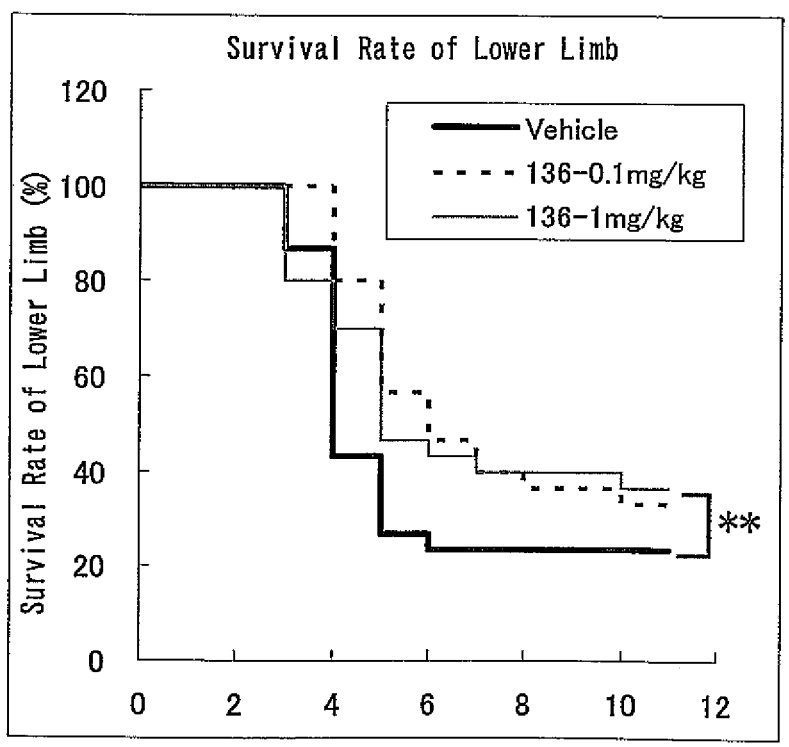
FIG. 6 is a diagram showing the results of Example Compound 136 in Test Example 4.
Figure 7:
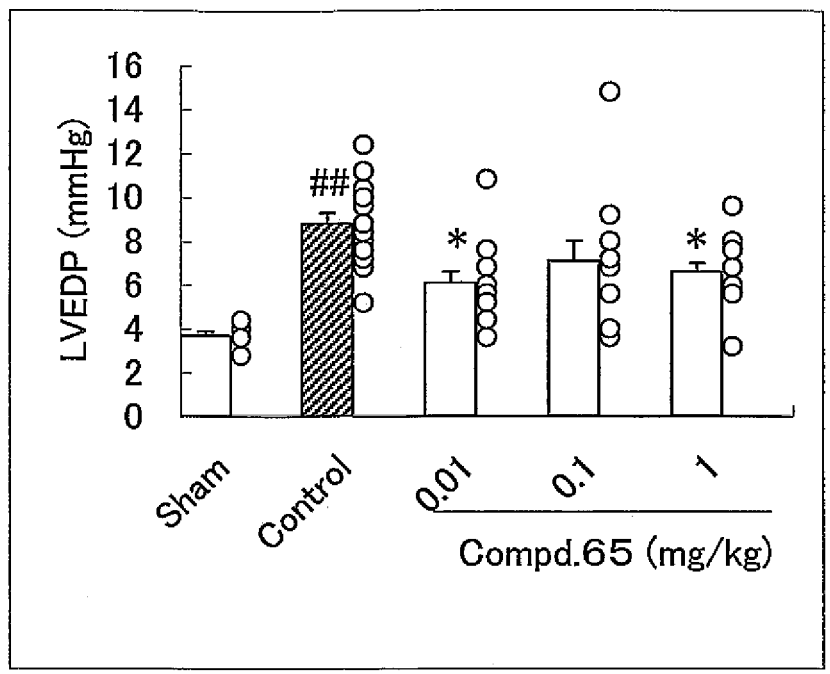
FIG. 7 is a diagram showing the results of LVEDP in Test Example 5.
Figure 8:
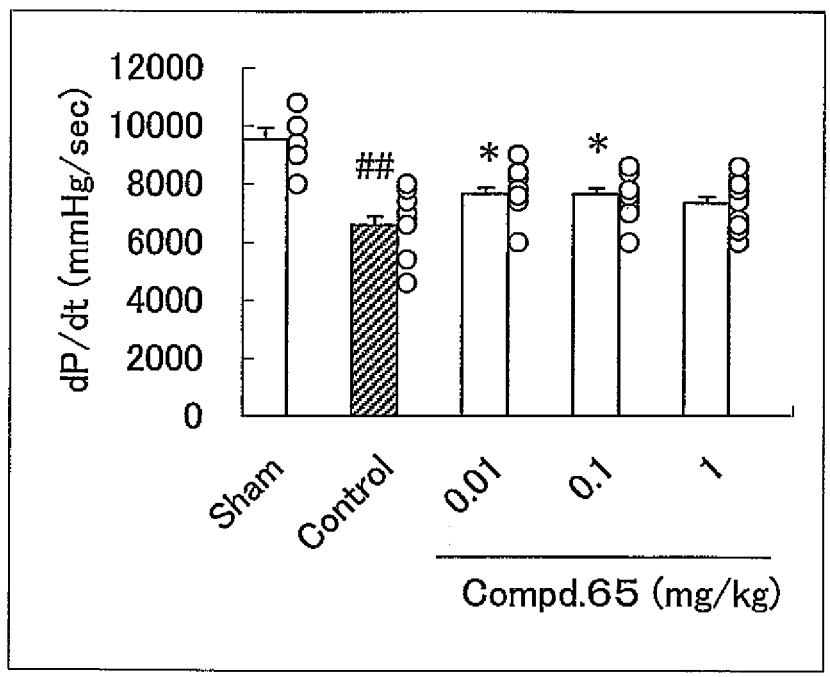
FIG. 8 is a diagram showing the results of LVdP/dt max in Test Example 5.
Figure 9:
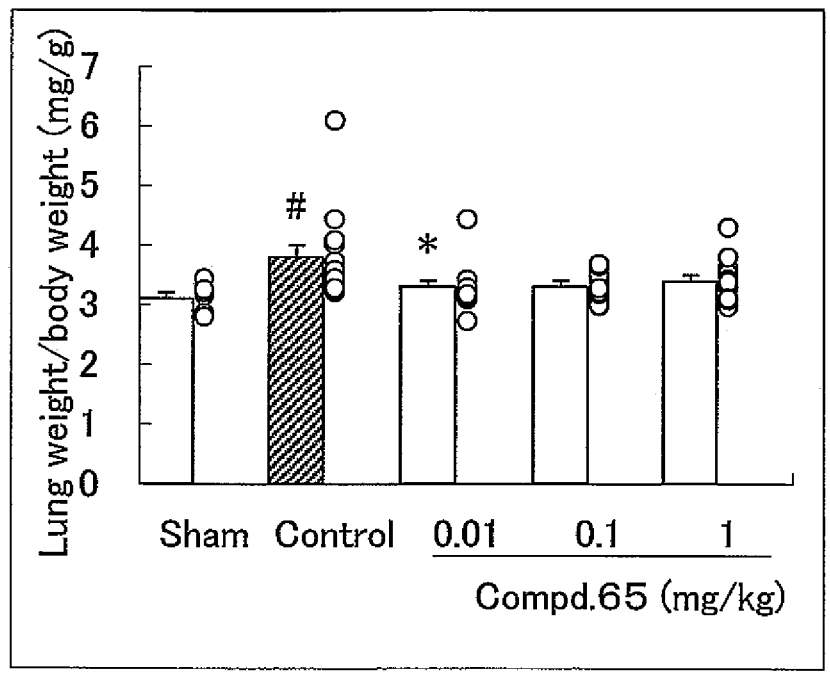
FIG. 9 is a diagram showing the results of lung weight measurement in Test Example 5.
Figure 10:
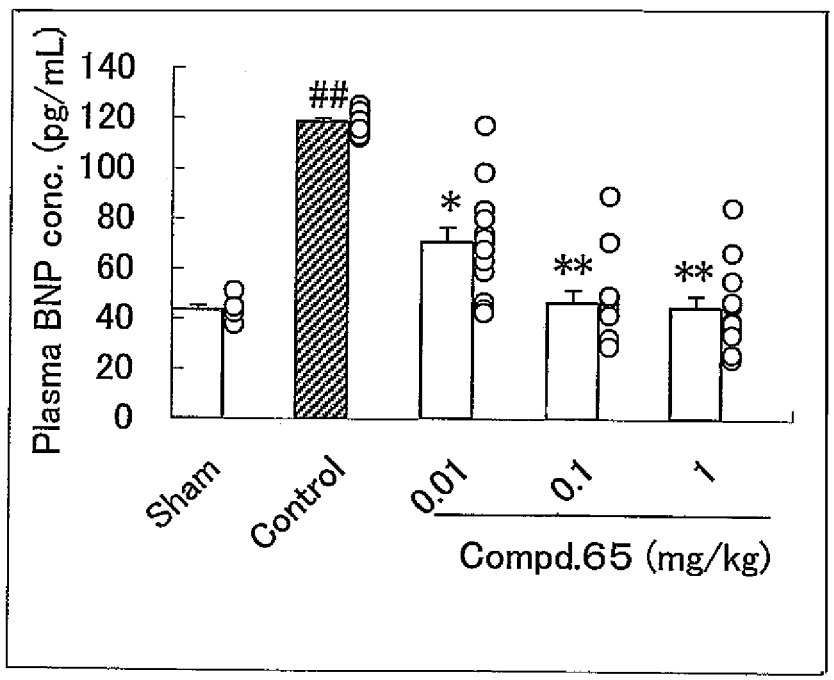
FIG. 10 is a diagram showing the results of plasma BMP levels in Test Example 5.
Figure 11:
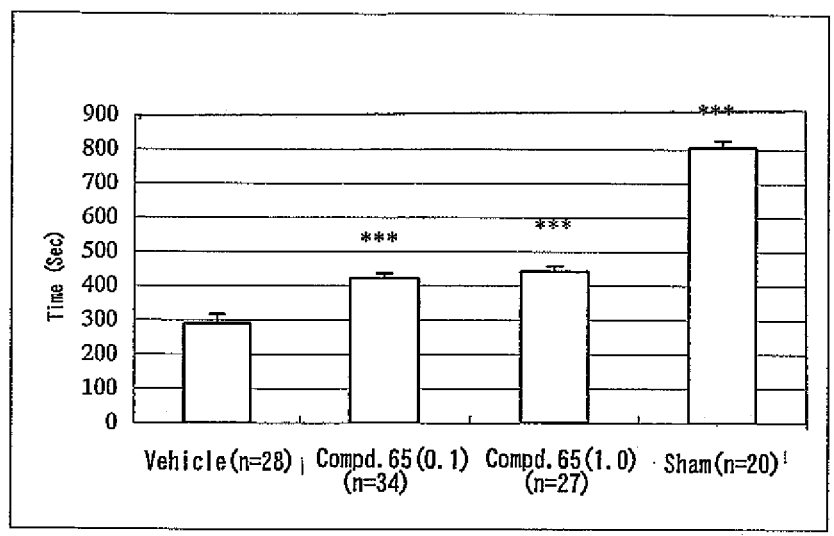
FIG. 11 is a diagram showing the results of Example Compound 65 in Test Example 6.
Figure 12:
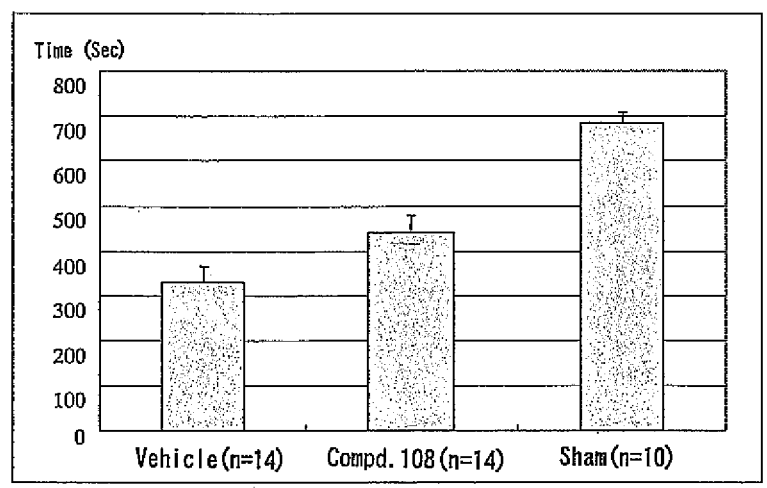
FIG. 12 is a diagram showing the results of Example Compound 108 in Test Example 6.
Figure 13:
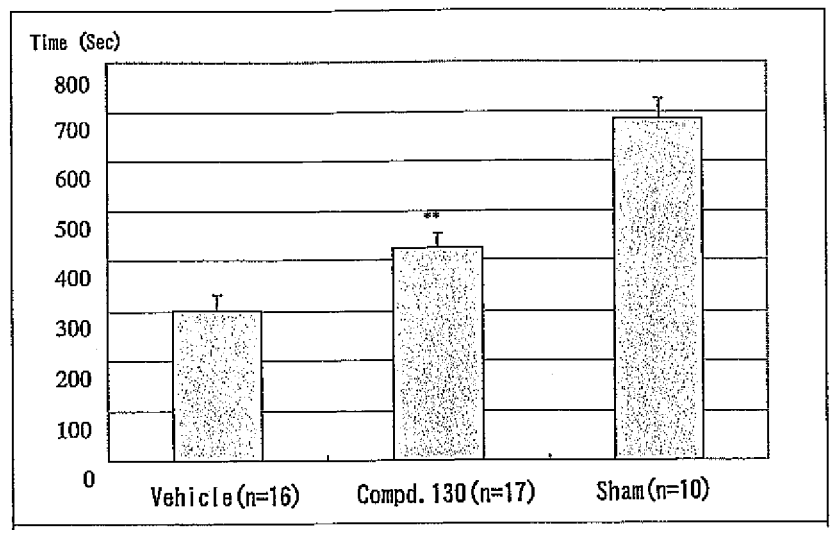
FIG. 13 is a diagram showing the results of Example Compound 130 in Test Example 6.
Figure 14:
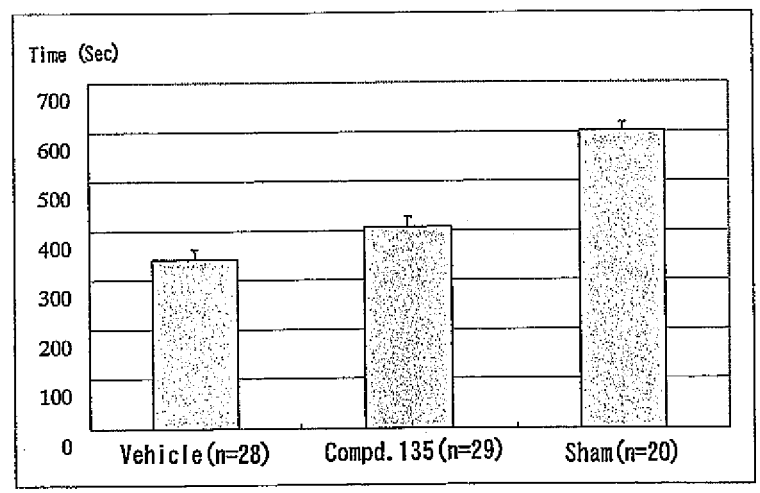
FIG. 14 is a diagram showing the results of Example Compound 135 in Test Example 6.
Figure 15:
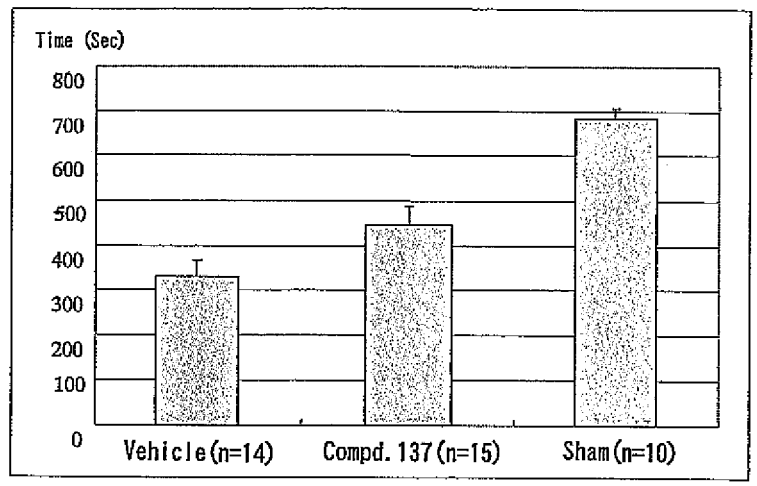
FIG. 15 is a diagram showing the results of Example Compound 137 in Test Example 6.
Figure 16:
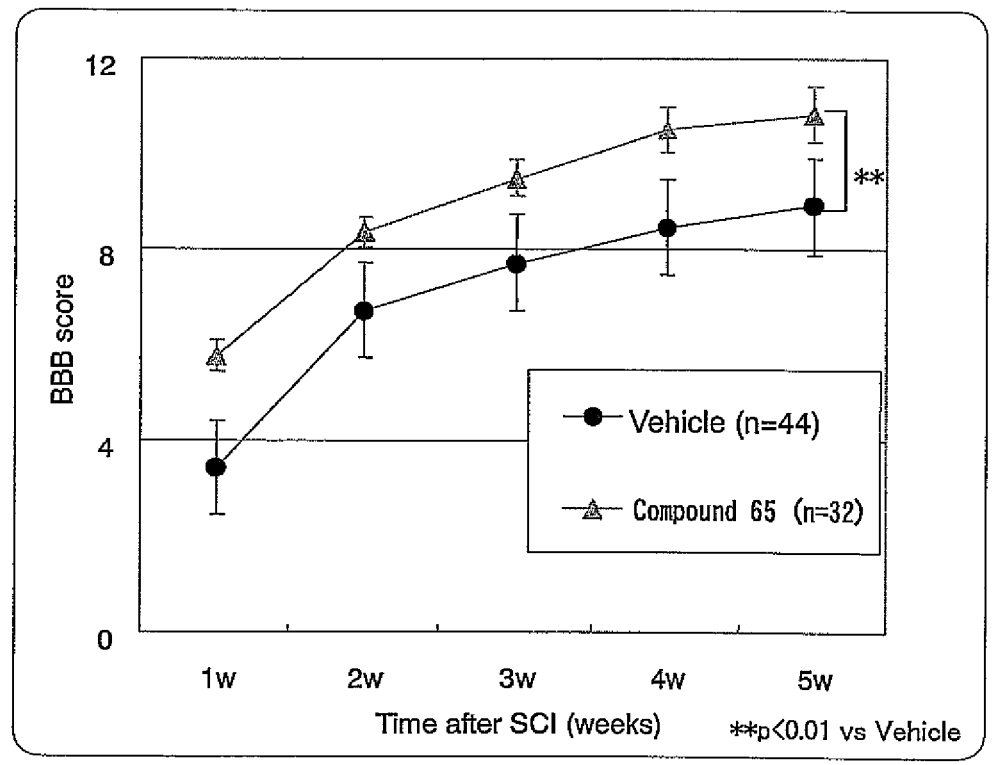
FIG. 16 is a diagram showing the results of Test Example 7.

The invention claimed is:

1. A compound, wherein the compound is:
2-(5-amino-4,6-dimethylpyrimidine-2-yloxy)-N-(1-benzylpiperidine-4-yl)-N-methylacetamide.

2. A pharmaceutical preparation comprising the compound of claim 1 as an active ingredient and a pharmaceutically acceptable excipient.

3. A pharmaceutical preparation comprising the compound of claim 1 and, optionally, a filler, an expander, a binder, a moisturizer, a disintegrating agent, a surfactant, a lubricant, diluentant, excipient, or a mixture thereof.

4. A pharmaceutical preparation comprising the compound of claim 1, wherein the pharmaceutical preparation is in the form of a tablet, a pill, a powder, a liquid, a suspension, an emulsion, a granule, a capsule, a suppository, an injection liquid, an injection suspension, an ointment, a cataplasm, or an inhalant.

5. A method of treating spinal cord injury comprising administering to a patient in need thereof a therapeutically effective amount of the compound of claim 1.

6. The method of claim 5, wherein the compound is administered in the range of from about 0.1 mg/day/patient to about 1000 mg/day/patient.

7. A method for treating cerebral infarction comprising administering to a patient in need thereof a therapeutically effective amount of the compound of claim 1.

8. The method of claim 7, wherein the compound is administered in the range of from about 0.1 mg/day/patient to about 1000 mg/day/patient.

* * * * *

UNITED STATES PATENT AND TRADEMARK OFFICE
CERTIFICATE OF CORRECTION

| | | |
|---|---|---|
| PATENT NO. | : 8,592,435 B2 | Page 1 of 1 |
| APPLICATION NO. | : 12/596054 | |
| DATED | : November 26, 2013 | |
| INVENTOR(S) | : Takemoto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 475 days.

Signed and Sealed this
Eleventh Day of November, 2014

Michelle K. Lee
*Deputy Director of the United States Patent and Trademark Office*